(12) United States Patent
Boudreaux et al.

(10) Patent No.: US 9,492,224 B2
(45) Date of Patent: Nov. 15, 2016

(54) MULTI-FUNCTION BI-POLAR FORCEPS

(71) Applicant: Ethicon Endo-Surgery, Inc., Cincinnati, OH (US)

(72) Inventors: Chad P. Boudreaux, Cincinnati, OH (US); Aaron C. Voegele, Loveland, OH (US); Charles J. Scheib, Loveland, OH (US)

(73) Assignee: EthiconEndo-Surgery, LLC, Guaynabo, PR (US)

( * ) Notice: Subject to any disclaimer, the term of this patent is extended or adjusted under 35 U.S.C. 154(b) by 83 days.

(21) Appl. No.: 14/032,391

(22) Filed: Sep. 20, 2013

(65) Prior Publication Data
US 2014/0094801 A1    Apr. 3, 2014

Related U.S. Application Data

(60) Provisional application No. 61/707,030, filed on Sep. 28, 2012.

(51) Int. Cl.
| | |
|---|---|
| *A61B 18/12* | (2006.01) |
| *A61B 18/14* | (2006.01) |
| *A61B 18/08* | (2006.01) |
| *A61B 18/18* | (2006.01) |
| *A61N 7/02* | (2006.01) |
| *A61B 17/29* | (2006.01) |
| *A61B 18/00* | (2006.01) |

(52) U.S. Cl.
CPC ......... *A61B 18/1445* (2013.01); *A61B 18/085* (2013.01); *A61B 18/1206* (2013.01); *A61B 18/18* (2013.01); *A61N 7/02* (2013.01); *A61B 2017/2945* (2013.01); *A61B 2018/00148* (2013.01); *A61B 2018/1455* (2013.01)

(58) Field of Classification Search
CPC ............ A61B 18/085; A61B 18/1445; A61B 2018/1455; A61B 2017/2945
See application file for complete search history.

(56) References Cited

U.S. PATENT DOCUMENTS

| | | |
|---|---|---|
| 2,366,274 A | 1/1945 | Luth et al. |
| 2,458,152 A | 1/1949 | Eakins |
| 2,510,693 A | 6/1950 | Green |

(Continued)

FOREIGN PATENT DOCUMENTS

| | | |
|---|---|---|
| DE | 29623113 U1 | 10/1997 |
| DE | 20004812 U1 | 9/2000 |

(Continued)

OTHER PUBLICATIONS

International Search Report for PCT/US2013/060838, Mar. 19, 2014 (6 pages).

(Continued)

*Primary Examiner* — Daniel Fowler

(57) ABSTRACT

An end effector is disclosed. The end effector includes a first jaw member. The first jaw member comprises a first electrode. The first jaw member defines a first aperture at a distal end. The end effector includes a second jaw member. The second jaw member comprises a second electrode. The second jaw member defines a second aperture at a distal end. The second jaw member is operatively coupled to the first jaw member. The first and second apertures are configured to define a single aperture when the first and second jaw members are in a closed position. The first and second electrodes are configured to deliver energy.

12 Claims, 33 Drawing Sheets

(56) References Cited

U.S. PATENT DOCUMENTS

| | | | |
|---|---|---|---|
| 3,166,971 A | 1/1965 | Stoecker | |
| 3,580,841 A | 5/1971 | Cadotte et al. | |
| 3,703,651 A | 11/1972 | Blowers | |
| 3,777,760 A | 12/1973 | Essner | |
| 4,005,714 A | 2/1977 | Hiltebrandt | |
| 4,034,762 A | 7/1977 | Cosens et al. | |
| 4,058,126 A | 11/1977 | Leveen | |
| 4,220,154 A | 9/1980 | Semm | |
| 4,237,441 A | 12/1980 | van Konynenburg et al. | |
| 4,281,785 A | 8/1981 | Brooks | |
| 4,304,987 A | 12/1981 | van Konynenburg | |
| 4,463,759 A | 8/1984 | Garito et al. | |
| 4,492,231 A | 1/1985 | Auth | |
| 4,535,773 A | 8/1985 | Yoon | |
| 4,545,926 A | 10/1985 | Fouts, Jr. et al. | |
| 4,550,870 A | 11/1985 | Krumme et al. | |
| 4,582,236 A | 4/1986 | Hirose | |
| 4,617,927 A | 10/1986 | Manes | |
| 4,735,603 A | 4/1988 | Goodson et al. | |
| 4,761,871 A | 8/1988 | O'Connor et al. | |
| 4,830,462 A | 5/1989 | Karny et al. | |
| 4,849,133 A | 7/1989 | Yoshida et al. | |
| 4,860,745 A | 8/1989 | Farin et al. | |
| 4,878,493 A | 11/1989 | Pasternak et al. | |
| 4,910,389 A | 3/1990 | Sherman et al. | |
| 4,920,978 A | 5/1990 | Colvin | |
| 5,061,269 A | 10/1991 | Muller | |
| 5,099,840 A | 3/1992 | Goble et al. | |
| 5,104,025 A | 4/1992 | Main et al. | |
| 5,106,538 A | 4/1992 | Barma et al. | |
| 5,108,383 A | 4/1992 | White | |
| 5,160,334 A | 11/1992 | Billings et al. | |
| 5,190,541 A | 3/1993 | Abele et al. | |
| 5,205,459 A | 4/1993 | Brinkerhoff et al. | |
| 5,217,460 A | 6/1993 | Knoepfler | |
| 5,234,428 A | 8/1993 | Kaufman | |
| 5,258,006 A | 11/1993 | Rydell et al. | |
| 5,285,945 A | 2/1994 | Brinkerhoff et al. | |
| 5,290,286 A | 3/1994 | Parins | |
| 5,309,927 A | 5/1994 | Welch | |
| 5,318,564 A | 6/1994 | Eggers | |
| 5,318,589 A | 6/1994 | Lichtman | |
| 5,330,471 A | 7/1994 | Eggers | |
| 5,339,723 A | 8/1994 | Huitema | |
| 5,342,359 A | 8/1994 | Rydell | |
| 5,361,583 A | 11/1994 | Huitema | |
| 5,383,874 A | 1/1995 | Jackson et al. | |
| 5,387,207 A | 2/1995 | Dyer et al. | |
| 5,389,098 A | 2/1995 | Tsuruta et al. | |
| 5,395,312 A | 3/1995 | Desai | |
| 5,395,364 A | 3/1995 | Anderhub et al. | |
| 5,396,900 A | 3/1995 | Slater et al. | |
| 5,403,312 A | 4/1995 | Yates et al. | |
| 5,417,709 A | 5/1995 | Slater | |
| 5,428,504 A | 6/1995 | Bhatla | |
| 5,429,131 A | 7/1995 | Scheinman et al. | |
| 5,443,463 A * | 8/1995 | Stern et al. | 606/51 |
| 5,445,638 A | 8/1995 | Rydell et al. | |
| 5,451,227 A | 9/1995 | Michaelson | |
| 5,458,598 A | 10/1995 | Feinberg et al. | |
| 5,465,895 A | 11/1995 | Knodel et al. | |
| 5,472,443 A | 12/1995 | Cordis et al. | |
| 5,476,479 A * | 12/1995 | Green et al. | 606/205 |
| 5,480,409 A | 1/1996 | Riza | |
| 5,484,436 A | 1/1996 | Eggers et al. | |
| 5,486,189 A | 1/1996 | Mudry et al. | |
| 5,496,317 A | 3/1996 | Goble et al. | |
| 5,504,650 A | 4/1996 | Katsui et al. | |
| 5,509,922 A | 4/1996 | Aranyi et al. | |
| 5,511,556 A | 4/1996 | DeSantis | |
| 5,520,704 A | 5/1996 | Castro et al. | |
| 5,522,839 A | 6/1996 | Pilling | |
| 5,531,744 A | 7/1996 | Nardella et al. | |
| 5,542,916 A | 8/1996 | Hirsch et al. | |
| 5,558,671 A | 9/1996 | Yates | |
| 5,563,179 A | 10/1996 | Stone et al. | |
| 5,571,121 A | 11/1996 | Heifetz | |
| 5,573,534 A | 11/1996 | Stone | |
| 5,584,830 A | 12/1996 | Ladd et al. | |
| 5,599,350 A | 2/1997 | Schulze et al. | |
| 5,611,813 A | 3/1997 | Lichtman | |
| 5,618,307 A | 4/1997 | Donlon et al. | |
| 5,624,452 A | 4/1997 | Yates | |
| 5,647,871 A | 7/1997 | Levine et al. | |
| 5,658,281 A | 8/1997 | Heard | |
| 5,662,667 A | 9/1997 | Knodel | |
| 5,665,085 A | 9/1997 | Nardella | |
| 5,665,100 A * | 9/1997 | Yoon | 606/170 |
| 5,674,219 A | 10/1997 | Monson et al. | |
| 5,674,220 A | 10/1997 | Fox et al. | |
| 5,688,270 A | 11/1997 | Yates et al. | |
| 5,693,051 A | 12/1997 | Schulze et al. | |
| 5,709,680 A | 1/1998 | Yates et al. | |
| 5,713,896 A | 2/1998 | Nardella | |
| 5,716,366 A | 2/1998 | Yates | |
| 5,735,848 A | 4/1998 | Yates et al. | |
| 5,743,906 A | 4/1998 | Parins et al. | |
| 5,752,973 A | 5/1998 | Kieturakis | |
| 5,755,717 A | 5/1998 | Yates et al. | |
| 5,762,255 A | 6/1998 | Chrisman et al. | |
| 5,779,701 A | 7/1998 | McBrayer et al. | |
| 5,782,834 A | 7/1998 | Lucey et al. | |
| 5,792,138 A | 8/1998 | Shipp | |
| 5,797,941 A | 8/1998 | Schulze et al. | |
| 5,800,432 A | 9/1998 | Swanson | |
| 5,800,449 A | 9/1998 | Wales | |
| 5,807,393 A | 9/1998 | Williamson, IV et al. | |
| 5,810,811 A | 9/1998 | Yates et al. | |
| 5,817,033 A | 10/1998 | DeSantis et al. | |
| 5,817,093 A | 10/1998 | Williamson, IV et al. | |
| 5,836,909 A | 11/1998 | Cosmescu | |
| 5,836,943 A | 11/1998 | Miller, III | |
| 5,853,412 A | 12/1998 | Mayenberger | |
| 5,876,401 A | 3/1999 | Schulze et al. | |
| 5,880,668 A | 3/1999 | Hall | |
| 5,891,142 A | 4/1999 | Eggers et al. | |
| 5,906,625 A | 5/1999 | Bito et al. | |
| 5,984,938 A | 11/1999 | Yoon | |
| 6,003,517 A | 12/1999 | Sheffield et al. | |
| 6,013,052 A | 1/2000 | Durman et al. | |
| 6,024,741 A | 2/2000 | Williamson, IV et al. | |
| 6,024,744 A | 2/2000 | Kese et al. | |
| 6,033,399 A | 3/2000 | Gines | |
| 6,039,734 A | 3/2000 | Goble | |
| 6,050,996 A | 4/2000 | Schmaltz et al. | |
| 6,063,098 A | 5/2000 | Houser et al. | |
| 6,068,629 A | 5/2000 | Haissaguerre et al. | |
| 6,074,389 A | 6/2000 | Levine et al. | |
| 6,091,995 A | 7/2000 | Ingle et al. | |
| 6,099,483 A | 8/2000 | Palmer et al. | |
| 6,099,550 A | 8/2000 | Yoon | |
| H1904 H | 10/2000 | Yates et al. | |
| 6,144,402 A | 11/2000 | Norsworthy et al. | |
| 6,152,923 A * | 11/2000 | Ryan | 606/51 |
| 6,174,309 B1 | 1/2001 | Wrublewski et al. | |
| 6,206,876 B1 | 3/2001 | Levine et al. | |
| 6,228,080 B1 | 5/2001 | Gines | |
| 6,259,230 B1 | 7/2001 | Chou | |
| 6,277,117 B1 | 8/2001 | Tetzlaff et al. | |
| 6,292,700 B1 | 9/2001 | Morrison et al. | |
| 6,325,799 B1 | 12/2001 | Goble | |
| 6,340,878 B1 | 1/2002 | Oglesbee | |
| 6,391,026 B1 | 5/2002 | Hung et al. | |
| 6,398,779 B1 | 6/2002 | Buysse et al. | |
| H2037 H | 7/2002 | Yates et al. | |
| 6,419,675 B1 | 7/2002 | Gallo, Sr. | |
| 6,430,446 B1 | 8/2002 | Knowlton | |
| 6,443,968 B1 | 9/2002 | Holthaus et al. | |
| 6,458,128 B1 | 10/2002 | Schulze | |
| 6,464,702 B2 | 10/2002 | Schulze et al. | |
| 6,500,112 B1 | 12/2002 | Khouri | |
| 6,500,176 B1 | 12/2002 | Truckai et al. | |
| 6,503,248 B1 | 1/2003 | Levine | |
| 6,511,480 B1 | 1/2003 | Tetzlaff et al. | |

(56) References Cited

U.S. PATENT DOCUMENTS

| | | |
|---|---|---|
| 6,514,252 B2 | 2/2003 | Nezhat et al. |
| 6,517,565 B1 | 2/2003 | Whitman et al. |
| 6,531,846 B1 | 3/2003 | Smith |
| 6,533,784 B2 | 3/2003 | Truckai et al. |
| 6,537,272 B2 | 3/2003 | Christopherson et al. |
| 6,554,829 B2 | 4/2003 | Schulze et al. |
| 6,558,376 B2 | 5/2003 | Bishop |
| 6,572,639 B1 | 6/2003 | Ingle et al. |
| 6,575,969 B1 | 6/2003 | Rittman, III et al. |
| 6,584,360 B2 | 6/2003 | Francischelli et al. |
| 6,585,735 B1 | 7/2003 | Lands et al. |
| 6,589,200 B1 | 7/2003 | Schwemberger et al. |
| 6,602,252 B2 | 8/2003 | Mollenauer |
| 6,620,161 B2 | 9/2003 | Schulze et al. |
| 6,622,731 B2 | 9/2003 | Daniel et al. |
| 6,623,482 B2 | 9/2003 | Pendekanti et al. |
| 6,635,057 B2 | 10/2003 | Harano et al. |
| 6,651,669 B1 | 11/2003 | Burnside |
| 6,656,177 B2 | 12/2003 | Truckai et al. |
| 6,656,198 B2 | 12/2003 | Tsonton et al. |
| 6,673,248 B2 | 1/2004 | Chowdhury |
| 6,679,882 B1 | 1/2004 | Kornerup |
| 6,695,840 B2 | 2/2004 | Schulze |
| 6,722,552 B2 | 4/2004 | Fenton, Jr. |
| 6,770,072 B1 | 8/2004 | Truckai et al. |
| 6,773,409 B2 | 8/2004 | Truckai et al. |
| 6,773,435 B2 | 8/2004 | Schulze et al. |
| 6,789,939 B2 | 9/2004 | Schrödinger et al. |
| 6,796,981 B2 | 9/2004 | Wham et al. |
| 6,800,085 B2 | 10/2004 | Selmon et al. |
| 6,802,843 B2 | 10/2004 | Truckai et al. |
| 6,811,842 B1 | 11/2004 | Ehrnsperger et al. |
| 6,821,273 B2 | 11/2004 | Mollenauer |
| 6,835,199 B2 | 12/2004 | McGuckin, Jr. et al. |
| 6,840,938 B1 | 1/2005 | Morley et al. |
| 6,860,880 B2 | 3/2005 | Treat et al. |
| 6,905,497 B2 | 6/2005 | Truckai et al. |
| 6,908,463 B2 | 6/2005 | Treat et al. |
| 6,913,579 B2 | 7/2005 | Truckai et al. |
| 6,926,716 B2 | 8/2005 | Baker et al. |
| 6,929,622 B2 | 8/2005 | Chian |
| 6,929,644 B2 | 8/2005 | Truckai et al. |
| 6,953,461 B2 | 10/2005 | McClurken et al. |
| 7,000,818 B2 | 2/2006 | Shelton, IV et al. |
| 7,011,657 B2 | 3/2006 | Truckai et al. |
| 7,041,102 B2 | 5/2006 | Truckai et al. |
| 7,052,496 B2 | 5/2006 | Yamauchi |
| 7,055,731 B2 | 6/2006 | Shelton, IV et al. |
| 7,063,699 B2 | 6/2006 | Hess et al. |
| 7,066,936 B2 | 6/2006 | Ryan |
| 7,070,597 B2 | 7/2006 | Truckai et al. |
| 7,083,618 B2 | 8/2006 | Couture et al. |
| 7,083,619 B2 | 8/2006 | Truckai et al. |
| 7,087,054 B2 | 8/2006 | Truckai et al. |
| 7,094,235 B2 | 8/2006 | Francischelli et al. |
| 7,101,371 B2 | 9/2006 | Dycus et al. |
| 7,101,372 B2 | 9/2006 | Dycus et al. |
| 7,101,373 B2 | 9/2006 | Dycus et al. |
| 7,112,201 B2 | 9/2006 | Truckai et al. |
| 7,118,570 B2 | 10/2006 | Tetzlaff et al. |
| 7,125,409 B2 | 10/2006 | Truckai et al. |
| 7,131,970 B2 | 11/2006 | Moses et al. |
| 7,137,980 B2 | 11/2006 | Buysse et al. |
| 7,143,925 B2 | 12/2006 | Shelton, IV et al. |
| 7,147,138 B2 | 12/2006 | Shelton, IV |
| 7,156,846 B2 | 1/2007 | Dycus et al. |
| 7,160,296 B2 | 1/2007 | Pearson et al. |
| 7,169,146 B2 | 1/2007 | Truckai et al. |
| 7,169,156 B2 | 1/2007 | Hart |
| 7,186,253 B2 | 3/2007 | Truckai et al. |
| 7,189,233 B2 | 3/2007 | Truckai et al. |
| 7,195,631 B2 | 3/2007 | Dumbauld |
| 7,207,471 B2 | 4/2007 | Heinrich et al. |
| 7,220,951 B2 | 5/2007 | Truckai et al. |
| 7,225,964 B2 | 6/2007 | Mastri et al. |
| 7,226,448 B2 | 6/2007 | Bertolero et al. |
| 7,232,440 B2 | 6/2007 | Dumbauld et al. |
| 7,235,073 B2 | 6/2007 | Levine et al. |
| 7,241,294 B2 | 7/2007 | Reschke |
| 7,251,531 B2 | 7/2007 | Mosher et al. |
| 7,252,667 B2 | 8/2007 | Moses et al. |
| 7,267,677 B2 | 9/2007 | Johnson et al. |
| 7,267,685 B2 | 9/2007 | Butaric et al. |
| 7,287,682 B1 | 10/2007 | Ezzat et al. |
| 7,300,450 B2 | 11/2007 | Vleugels et al. |
| 7,303,557 B2 | 12/2007 | Wham et al. |
| 7,307,313 B2 | 12/2007 | Ohyanagi et al. |
| 7,309,849 B2 | 12/2007 | Truckai et al. |
| 7,311,709 B2 | 12/2007 | Truckai et al. |
| 7,329,257 B2 | 2/2008 | Kanehira et al. |
| 7,354,440 B2 | 4/2008 | Truckai et al. |
| 7,357,287 B2 | 4/2008 | Shelton, IV et al. |
| 7,364,577 B2 | 4/2008 | Wham et al. |
| 7,367,976 B2 | 5/2008 | Lawes et al. |
| 7,371,227 B2 | 5/2008 | Zeiner |
| RE40,388 E | 6/2008 | Gines |
| 7,381,209 B2 | 6/2008 | Truckai et al. |
| 7,396,356 B2 | 7/2008 | Mollenauer |
| 7,403,224 B2 | 7/2008 | Fuller et al. |
| 7,404,508 B2 | 7/2008 | Smith et al. |
| 7,407,077 B2 | 8/2008 | Ortiz et al. |
| 7,422,139 B2 | 9/2008 | Shelton, IV et al. |
| 7,435,582 B2 | 10/2008 | Zimmermann et al. |
| 7,442,193 B2 | 10/2008 | Shields et al. |
| 7,445,621 B2 | 11/2008 | Dumbauld et al. |
| 7,464,846 B2 | 12/2008 | Shelton, IV et al. |
| 7,473,253 B2 | 1/2009 | Dycus et al. |
| 7,488,319 B2 | 2/2009 | Yates |
| 7,491,201 B2 | 2/2009 | Shields et al. |
| 7,494,501 B2 | 2/2009 | Ahlberg et al. |
| 7,498,080 B2 | 3/2009 | Tung et al. |
| 7,510,107 B2 | 3/2009 | Timm et al. |
| 7,513,025 B2 | 4/2009 | Fischer |
| 7,517,349 B2 | 4/2009 | Truckai et al. |
| 7,540,872 B2 | 6/2009 | Schechter et al. |
| 7,550,216 B2 | 6/2009 | Ofer et al. |
| 7,559,452 B2 | 7/2009 | Wales et al. |
| 7,582,086 B2 | 9/2009 | Privitera et al. |
| 7,586,289 B2 | 9/2009 | Andruk et al. |
| 7,588,176 B2 | 9/2009 | Timm et al. |
| 7,594,925 B2 | 9/2009 | Danek et al. |
| 7,597,693 B2 | 10/2009 | Garrison |
| 7,604,150 B2 | 10/2009 | Boudreaux |
| 7,628,791 B2 | 12/2009 | Garrison et al. |
| 7,628,792 B2 | 12/2009 | Guerra |
| 7,632,267 B2 | 12/2009 | Dahla |
| 7,632,269 B2 | 12/2009 | Truckai et al. |
| 7,641,653 B2 | 1/2010 | Dalla Betta et al. |
| 7,641,671 B2 | 1/2010 | Crainich |
| 7,644,848 B2 | 1/2010 | Swayze et al. |
| 7,645,277 B2 | 1/2010 | McClurken et al. |
| 7,648,499 B2 | 1/2010 | Orszulak et al. |
| 7,658,311 B2 | 2/2010 | Boudreaux |
| 7,665,647 B2 | 2/2010 | Shelton, IV et al. |
| 7,666,206 B2 | 2/2010 | Taniguchi et al. |
| 7,703,459 B2 | 4/2010 | Saadat et al. |
| 7,708,751 B2 | 5/2010 | Hughes et al. |
| 7,722,607 B2 | 5/2010 | Dumbauld et al. |
| 7,753,904 B2 | 7/2010 | Shelton, IV et al. |
| 7,753,908 B2 | 7/2010 | Swanson |
| 7,762,445 B2 | 7/2010 | Heinrich et al. |
| 7,766,910 B2 | 8/2010 | Hixson et al. |
| 7,776,037 B2 | 8/2010 | Odom |
| 7,780,663 B2 | 8/2010 | Yates et al. |
| 7,784,663 B2 | 8/2010 | Shelton, IV |
| 7,803,156 B2 | 9/2010 | Eder et al. |
| 7,815,641 B2 | 10/2010 | Dodde et al. |
| 7,819,298 B2 | 10/2010 | Hall et al. |
| 7,819,299 B2 | 10/2010 | Sheltoin, IV et al. |
| 7,832,408 B2 | 11/2010 | Shelton, IV et al. |
| 7,832,612 B2 | 11/2010 | Baxter, III et al. |
| 7,846,159 B2 | 12/2010 | Morrison et al. |
| 7,846,160 B2 | 12/2010 | Payne et al. |
| 7,879,035 B2 | 2/2011 | Garrison et al. |

(56) References Cited

U.S. PATENT DOCUMENTS

| | | |
|---|---|---|
| 7,879,070 B2 | 2/2011 | Ortiz et al. |
| 7,901,400 B2 | 3/2011 | Wham et al. |
| 7,931,649 B2 | 4/2011 | Couture et al. |
| 7,935,114 B2 | 5/2011 | Takashino et al. |
| 7,955,331 B2 | 6/2011 | Truckai et al. |
| 7,963,963 B2 | 6/2011 | Francischelli et al. |
| 7,967,602 B2 | 6/2011 | Lindquist |
| 7,981,113 B2 | 7/2011 | Truckai et al. |
| 7,997,278 B2 | 8/2011 | Utley et al. |
| 8,020,743 B2 | 9/2011 | Shelton, IV |
| 8,058,771 B2 | 11/2011 | Giordano et al. |
| 8,070,036 B1 | 12/2011 | Knodel et al. |
| 8,105,323 B2 | 1/2012 | Buysse et al. |
| 8,128,624 B2 | 3/2012 | Couture et al. |
| 8,136,712 B2 | 3/2012 | Zingman |
| 8,141,762 B2 | 3/2012 | Bedi et al. |
| 8,157,145 B2 | 4/2012 | Shelton, IV et al. |
| 8,197,472 B2 | 6/2012 | Lau et al. |
| 8,197,479 B2 | 6/2012 | Olson et al. |
| 8,221,415 B2 | 7/2012 | Francischelli |
| 8,246,615 B2 | 8/2012 | Behnke |
| 8,246,618 B2 | 8/2012 | Bucciaglia et al. |
| 8,251,994 B2 | 8/2012 | McKenna et al. |
| 8,262,563 B2 | 9/2012 | Bakos et al. |
| 8,277,446 B2 * | 10/2012 | Heard ............ 606/51 |
| 8,277,447 B2 | 10/2012 | Garrison et al. |
| 8,282,669 B2 | 10/2012 | Gerber et al. |
| 8,287,528 B2 | 10/2012 | Wham et al. |
| 8,292,886 B2 | 10/2012 | Kerr et al. |
| 8,298,232 B2 | 10/2012 | Unger |
| 8,303,583 B2 | 11/2012 | Hosier et al. |
| 8,323,310 B2 | 12/2012 | Kingsley |
| 8,377,059 B2 | 2/2013 | Deville et al. |
| 8,397,971 B2 | 3/2013 | Yates et al. |
| 8,414,577 B2 | 4/2013 | Boudreaux et al. |
| 8,430,876 B2 | 4/2013 | Kappus et al. |
| 8,453,906 B2 | 6/2013 | Huang et al. |
| 8,460,288 B2 | 6/2013 | Tamai et al. |
| 8,460,292 B2 | 6/2013 | Truckai et al. |
| 8,486,057 B2 | 7/2013 | Behnke, II |
| 8,496,682 B2 | 7/2013 | Guerra et al. |
| 8,535,311 B2 | 9/2013 | Schall |
| 8,562,598 B2 | 10/2013 | Falkenstein et al. |
| 8,562,604 B2 | 10/2013 | Nishimura |
| 8,568,412 B2 | 10/2013 | Brandt et al. |
| 8,569,997 B2 | 10/2013 | Lee |
| 8,574,231 B2 | 11/2013 | Boudreaux et al. |
| 8,591,506 B2 | 11/2013 | Wham et al. |
| 8,613,383 B2 | 12/2013 | Beckman et al. |
| 8,623,044 B2 | 1/2014 | Timm et al. |
| 8,628,529 B2 | 1/2014 | Aldridge et al. |
| 8,632,461 B2 | 1/2014 | Glossop |
| 8,647,350 B2 | 2/2014 | Mohan et al. |
| 8,663,222 B2 | 3/2014 | Anderson et al. |
| 8,685,020 B2 | 4/2014 | Weizman et al. |
| 8,696,665 B2 | 4/2014 | Hunt et al. |
| 8,702,609 B2 | 4/2014 | Hadjicostis |
| 8,702,704 B2 | 4/2014 | Shelton, IV et al. |
| 8,709,035 B2 | 4/2014 | Johnson et al. |
| 8,715,270 B2 | 5/2014 | Weitzner et al. |
| 8,715,277 B2 | 5/2014 | Weizman |
| 8,734,443 B2 | 5/2014 | Hixson et al. |
| 8,747,404 B2 | 6/2014 | Boudreaux et al. |
| 8,753,338 B2 | 6/2014 | Widenhouse et al. |
| 8,764,747 B2 | 7/2014 | Cummings et al. |
| 8,790,342 B2 | 7/2014 | Stulen et al. |
| 8,795,276 B2 | 8/2014 | Dietz et al. |
| 8,795,327 B2 | 8/2014 | Dietz et al. |
| 8,834,466 B2 | 9/2014 | Cummings et al. |
| 8,834,518 B2 | 9/2014 | Faller et al. |
| 8,888,776 B2 | 11/2014 | Dietz et al. |
| 8,906,016 B2 | 12/2014 | Boudreaux et al. |
| 8,926,608 B2 | 1/2015 | Bacher et al. |
| 8,939,974 B2 | 1/2015 | Boudreaux et al. |
| 8,951,248 B2 | 2/2015 | Messerly et al. |
| 8,956,349 B2 | 2/2015 | Aldridge et al. |
| 8,979,843 B2 | 3/2015 | Timm et al. |
| 8,979,844 B2 | 3/2015 | White et al. |
| 8,986,302 B2 | 3/2015 | Aldridge et al. |
| 9,005,199 B2 | 4/2015 | Beckman et al. |
| 9,011,437 B2 | 4/2015 | Woodruff et al. |
| 9,044,243 B2 | 6/2015 | Johnson et al. |
| 2002/0022836 A1 | 2/2002 | Goble et al. |
| 2002/0165541 A1 | 11/2002 | Whitman |
| 2002/0183734 A1* | 12/2002 | Bommannan et al. ......... 606/32 |
| 2003/0014053 A1 | 1/2003 | Nguyen et al. |
| 2003/0105474 A1 | 6/2003 | Bonutti |
| 2003/0114851 A1 | 6/2003 | Truckai et al. |
| 2003/0130693 A1 | 7/2003 | Levin et al. |
| 2003/0139741 A1* | 7/2003 | Goble ............... A61B 18/1445 606/48 |
| 2003/0158548 A1 | 8/2003 | Phan et al. |
| 2003/0216722 A1 | 11/2003 | Swanson |
| 2003/0229344 A1 | 12/2003 | Dycus et al. |
| 2004/0019350 A1 | 1/2004 | O'Brien et al. |
| 2004/0092992 A1 | 5/2004 | Adams et al. |
| 2004/0138621 A1 | 7/2004 | Jahns et al. |
| 2004/0167508 A1 | 8/2004 | Wham et al. |
| 2004/0193150 A1 | 9/2004 | Sharkey et al. |
| 2004/0232196 A1 | 11/2004 | Shelton, IV et al. |
| 2004/0249374 A1 | 12/2004 | Tetzlaff et al. |
| 2004/0260273 A1 | 12/2004 | Wan |
| 2005/0015125 A1 | 1/2005 | Mioduski et al. |
| 2005/0033278 A1 | 2/2005 | McClurken et al. |
| 2005/0085809 A1 | 4/2005 | Mucko et al. |
| 2005/0090817 A1 | 4/2005 | Phan |
| 2005/0131390 A1* | 6/2005 | Heinrich ............ A61B 17/0469 606/1 |
| 2005/0165429 A1 | 7/2005 | Douglas et al. |
| 2005/0171522 A1 | 8/2005 | Christopherson |
| 2005/0203507 A1 | 9/2005 | Truckai et al. |
| 2005/0261581 A1 | 11/2005 | Hughes et al. |
| 2005/0267464 A1 | 12/2005 | Truckai et al. |
| 2006/0052778 A1 | 3/2006 | Chapman et al. |
| 2006/0064086 A1 | 3/2006 | Odom |
| 2006/0069388 A1 | 3/2006 | Truckai et al. |
| 2006/0159731 A1 | 7/2006 | Shoshan |
| 2006/0270916 A1 | 11/2006 | Skwarek et al. |
| 2006/0293656 A1 | 12/2006 | Shadduck et al. |
| 2007/0027469 A1 | 2/2007 | Smith et al. |
| 2007/0073185 A1 | 3/2007 | Nakao |
| 2007/0073341 A1 | 3/2007 | Smith et al. |
| 2007/0106158 A1 | 5/2007 | Madan et al. |
| 2007/0146113 A1 | 6/2007 | Truckai et al. |
| 2007/0173803 A1 | 7/2007 | Wham et al. |
| 2007/0173813 A1 | 7/2007 | Odom |
| 2007/0185474 A1 | 8/2007 | Nahen |
| 2007/0191713 A1 | 8/2007 | Eichmann et al. |
| 2007/0191830 A1 | 8/2007 | Cromton, Jr. et al. |
| 2007/0203483 A1 | 8/2007 | Kim et al. |
| 2007/0208312 A1 | 9/2007 | Norton et al. |
| 2007/0232920 A1 | 10/2007 | Kowalski et al. |
| 2007/0232926 A1 | 10/2007 | Stulen et al. |
| 2007/0232927 A1 | 10/2007 | Madan et al. |
| 2007/0232928 A1 | 10/2007 | Wiener et al. |
| 2007/0236213 A1 | 10/2007 | Paden et al. |
| 2007/0239025 A1 | 10/2007 | Wiener et al. |
| 2007/0260242 A1 | 11/2007 | Dycus et al. |
| 2007/0265613 A1 | 11/2007 | Edelstein et al. |
| 2008/0015575 A1 | 1/2008 | Odom et al. |
| 2008/0071269 A1 | 3/2008 | Hilario et al. |
| 2008/0114355 A1 | 5/2008 | Whayne et al. |
| 2008/0147058 A1 | 6/2008 | Horrell et al. |
| 2008/0147062 A1 | 6/2008 | Truckai et al. |
| 2008/0167522 A1 | 7/2008 | Giordano et al. |
| 2008/0188755 A1 | 8/2008 | Hart |
| 2008/0188851 A1 | 8/2008 | Truckai et al. |
| 2008/0188912 A1 | 8/2008 | Stone et al. |
| 2008/0221565 A1 | 9/2008 | Eder et al. |
| 2008/0262491 A1 | 10/2008 | Swoyer et al. |
| 2008/0269862 A1 | 10/2008 | Elmouelhi et al. |
| 2008/0281315 A1 | 11/2008 | Gines |
| 2008/0294158 A1 | 11/2008 | Pappone et al. |
| 2009/0012516 A1 | 1/2009 | Curtis et al. |

(56) References Cited

U.S. PATENT DOCUMENTS

| | | |
|---|---|---|
| 2009/0048589 A1 | 2/2009 | Takashino et al. |
| 2009/0076506 A1 | 3/2009 | Baker |
| 2009/0076534 A1 | 3/2009 | Shelton, IV et al. |
| 2009/0099582 A1 | 4/2009 | Isaacs et al. |
| 2009/0125026 A1 | 5/2009 | Rioux et al. |
| 2009/0125027 A1 | 5/2009 | Fischer |
| 2009/0138003 A1 | 5/2009 | Deville et al. |
| 2009/0138006 A1 | 5/2009 | Bales et al. |
| 2009/0182332 A1 | 7/2009 | Long et al. |
| 2009/0206140 A1 | 8/2009 | Scheib et al. |
| 2009/0209979 A1* | 8/2009 | Yates et al. ............ 606/143 |
| 2009/0248002 A1 | 10/2009 | Takashino et al. |
| 2009/0248021 A1* | 10/2009 | McKenna ............... 606/51 |
| 2009/0320268 A1 | 12/2009 | Cunningham et al. |
| 2009/0326530 A1 | 12/2009 | Orban, III et al. |
| 2010/0032470 A1 | 2/2010 | Hess et al. |
| 2010/0036370 A1 | 2/2010 | Mirel et al. |
| 2010/0036380 A1 | 2/2010 | Taylor et al. |
| 2010/0076433 A1 | 3/2010 | Taylor et al. |
| 2010/0081863 A1 | 4/2010 | Hess et al. |
| 2010/0081864 A1 | 4/2010 | Hess et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |
| 2010/0094323 A1 | 4/2010 | Isaacs et al. |
| 2010/0168620 A1 | 7/2010 | Klimovitch et al. |
| 2010/0222752 A1 | 9/2010 | Collins, Jr. et al. |
| 2010/0237132 A1 | 9/2010 | Measamer et al. |
| 2010/0264194 A1 | 10/2010 | Huang et al. |
| 2010/0274278 A1 | 10/2010 | Fleenor et al. |
| 2011/0015627 A1 | 1/2011 | DiNardo et al. |
| 2011/0082486 A1 | 4/2011 | Messerly et al. |
| 2011/0087214 A1 | 4/2011 | Giordano et al. |
| 2011/0087215 A1 | 4/2011 | Aldridge et al. |
| 2011/0087216 A1 | 4/2011 | Aldridge et al. |
| 2011/0087217 A1 | 4/2011 | Yates et al. |
| 2011/0087220 A1 | 4/2011 | Felder et al. |
| 2011/0155781 A1 | 6/2011 | Swensgard et al. |
| 2011/0224668 A1 | 9/2011 | Johnson et al. |
| 2011/0276049 A1 | 11/2011 | Gerhardt |
| 2011/0276057 A1 | 11/2011 | Conlon et al. |
| 2011/0301605 A1 | 12/2011 | Horner |
| 2011/0306965 A1 | 12/2011 | Norvell et al. |
| 2011/0306967 A1 | 12/2011 | Payne et al. |
| 2012/0010616 A1 | 1/2012 | Huang et al. |
| 2012/0016413 A1 | 1/2012 | Timm et al. |
| 2012/0022519 A1 | 1/2012 | Huang et al. |
| 2012/0022526 A1 | 1/2012 | Aldridge et al. |
| 2012/0022527 A1 | 1/2012 | Woodruff et al. |
| 2012/0078248 A1 | 3/2012 | Worrell et al. |
| 2012/0083783 A1 | 4/2012 | Davison et al. |
| 2012/0109186 A1 | 5/2012 | Parrott et al. |
| 2012/0116379 A1 | 5/2012 | Yates et al. |
| 2012/0116391 A1 | 5/2012 | Houser et al. |
| 2012/0130256 A1 | 5/2012 | Buysse et al. |
| 2012/0136353 A1 | 5/2012 | Romero |
| 2012/0150170 A1 | 6/2012 | Buysse et al. |
| 2012/0172859 A1 | 7/2012 | Condie et al. |
| 2012/0265196 A1 | 10/2012 | Turner et al. |
| 2013/0023875 A1 | 1/2013 | Harris et al. |
| 2013/0030433 A1 | 1/2013 | Heard |
| 2013/0079762 A1 | 3/2013 | Twomey et al. |
| 2013/0085496 A1 | 4/2013 | Unger et al. |
| 2013/0103023 A1 | 4/2013 | Monson et al. |
| 2013/0103024 A1 | 4/2013 | Monson et al. |
| 2013/0123776 A1 | 5/2013 | Monson et al. |
| 2013/0123777 A1 | 5/2013 | Monson et al. |
| 2013/0123782 A1 | 5/2013 | Trees et al. |
| 2013/0131660 A1 | 5/2013 | Monson et al. |
| 2013/0253502 A1 | 9/2013 | Aronow et al. |
| 2013/0338661 A1 | 12/2013 | Behnke, II |
| 2014/0005680 A1 | 1/2014 | Shelton, IV et al. |
| 2014/0148806 A1 | 5/2014 | Witt et al. |
| 2014/0194914 A1 | 7/2014 | Hunt et al. |
| 2014/0194915 A1 | 7/2014 | Johnson et al. |
| 2014/0257284 A1 | 9/2014 | Artale |
| 2014/0330271 A1 | 11/2014 | Dietz et al. |
| 2014/0343550 A1 | 11/2014 | Faller et al. |
| 2015/0018826 A1 | 1/2015 | Boudreaux |
| 2015/0066022 A1 | 3/2015 | Shelton, IV et al. |
| 2015/0080876 A1 | 3/2015 | Worrell et al. |
| 2015/0080879 A1 | 3/2015 | Trees et al. |
| 2015/0080891 A1 | 3/2015 | Shelton, IV et al. |
| 2015/0133915 A1 | 5/2015 | Strobl et al. |
| 2015/0133921 A1 | 5/2015 | Strobl et al. |
| 2015/0190189 A1 | 7/2015 | Yates et al. |
| 2015/0196352 A1 | 7/2015 | Beckman et al. |
| 2015/0201953 A1 | 7/2015 | Strobl et al. |
| 2015/0230853 A1 | 8/2015 | Johnson et al. |

FOREIGN PATENT DOCUMENTS

| | | |
|---|---|---|
| DE | 10201569 A1 | 7/2003 |
| EP | 0340803 B1 | 8/1993 |
| EP | 0630612 A1 | 12/1994 |
| EP | 0705571 A1 | 4/1996 |
| EP | 0640317 B1 | 9/1999 |
| EP | 0722696 B1 | 12/2002 |
| EP | 1293172 B1 | 4/2006 |
| EP | 1749479 A1 | 2/2007 |
| EP | 1767157 A1 | 3/2007 |
| EP | 1878399 A1 | 1/2008 |
| EP | 1915953 A1 | 4/2008 |
| EP | 1532933 B1 | 5/2008 |
| EP | 1707143 B1 | 6/2008 |
| EP | 1943957 A2 | 7/2008 |
| EP | 1849424 B1 | 4/2009 |
| EP | 2042117 A1 | 4/2009 |
| EP | 2060238 A1 | 5/2009 |
| EP | 1810625 B1 | 8/2009 |
| EP | 2090238 A1 | 8/2009 |
| EP | 2090256 A2 | 8/2009 |
| EP | 2092905 A1 | 8/2009 |
| EP | 2105104 A2 | 9/2009 |
| EP | 1747761 B1 | 10/2009 |
| EP | 1769766 B1 | 2/2010 |
| EP | 2151204 A1 | 2/2010 |
| EP | 2153791 A1 | 2/2010 |
| EP | 2243439 A1 | 10/2010 |
| EP | 1728475 B1 | 8/2011 |
| EP | 2353518 A1 | 8/2011 |
| EP | 2508143 B1 | 2/2014 |
| GB | 2472216 A | 2/2011 |
| JP | H 08-229050 A | 9/1996 |
| JP | 2008-018226 A | 1/2008 |
| WO | WO 81/03272 A1 | 11/1981 |
| WO | WO 93/07817 | 4/1993 |
| WO | WO 93/22973 A1 | 11/1993 |
| WO | WO 95/10978 A1 | 4/1995 |
| WO | WO 96/35382 A1 | 11/1996 |
| WO | WO 97/10764 A1 | 3/1997 |
| WO | WO 98/00069 A1 | 1/1998 |
| WO | WO 98/40020 A1 | 9/1998 |
| WO | WO 98/57588 A1 | 12/1998 |
| WO | WO 99/23960 A1 | 5/1999 |
| WO | WO 99/40861 A1 | 8/1999 |
| WO | WO 00/24330 A1 | 5/2000 |
| WO | WO 00/24331 A1 | 5/2000 |
| WO | WO 00/25691 A1 | 5/2000 |
| WO | WO 01/28444 A1 | 4/2001 |
| WO | WO 02/080797 A1 | 10/2002 |
| WO | WO 03/001986 A2 | 1/2003 |
| WO | WO 03/013374 A1 | 2/2003 |
| WO | WO 03/020339 A2 | 3/2003 |
| WO | WO 03/028541 A2 | 4/2003 |
| WO | WO 03/030708 A2 | 4/2003 |
| WO | WO 03/068046 A2 | 8/2003 |
| WO | WO 2004/011037 A2 | 2/2004 |
| WO | WO 2004/078051 A2 | 9/2004 |
| WO | WO 2005/052959 A2 | 6/2005 |
| WO | WO 2006/021269 A1 | 3/2006 |
| WO | WO 2006/036706 A1 | 4/2006 |

(56) References Cited

FOREIGN PATENT DOCUMENTS

| WO | WO 2006/055166 A2 | 5/2006 |
|---|---|---|
| WO | WO 2008/020964 A2 | 2/2008 |
| WO | WO 2008/045348 A2 | 4/2008 |
| WO | WO 2008/099529 A1 | 8/2008 |
| WO | WO 2008/101356 A1 | 8/2008 |
| WO | WO 2009/022614 A1 | 2/2009 |
| WO | WO 2009/036818 A1 | 3/2009 |
| WO | WO 2009/039179 A1 | 3/2009 |
| WO | WO 2009/059741 A1 | 5/2009 |
| WO | WO 2009/082477 A2 | 7/2009 |
| WO | WO 2009/149234 A1 | 12/2009 |
| WO | WO 2010/017266 A1 | 2/2010 |
| WO | WO 2010/104755 A1 | 9/2010 |
| WO | WO 2011/084768 A1 | 7/2011 |
| WO | WO 2011/089717 A1 | 7/2011 |
| WO | WO 2011/144911 A1 | 11/2011 |
| WO | WO 2013/034629 A1 | 3/2013 |
| WO | WO 2013/062978 A2 | 5/2013 |

OTHER PUBLICATIONS

Arnoczky et al., "Thermal Modification of Conective Tissues: Basic Science Considerations and Clinical Implications," J. Am Acad Orthop Surg, vol. 8, No. 5, pp. 305-313 (Sep./Oct. 2000).
Chen et al., "Heat-Induced Changes in the Mechanics of a Collagenous Tissue: Isothermal Free Shrinkage," Transactions of the ASME, vol. 119, pp. 372-378 (Nov. 1997).
Chen et al., "Heat-Induced Changes in the Mechanics of a Collagenous Tissue: Isothermal, Isotonic Shrinkage," Transactions of the ASME, vol. 120, pp. 382-388 (Jun. 1998).
Chen et al., "Heat-induced changes in the mechanics of a collagenous tissue: pseudoelastic behavior at 37° C," Journal of Biomechanics, 31, pp. 211-216 (1998).
Chen et al., "Phenomenological Evolution Equations for Heat-Induced Shrinkage of a Collagenous Tissue," IEEE Transactions on Biomedical Engineering, vol. 45, No. 10, pp. 1234-1240 (Oct. 1998).
Covidien Brochure, [Value Analysis Brief], LigaSure Advance™ Pistol Grip, dated Rev. Apr. 2010 (7 pages).
Covidien Brochure, LigaSure Atlas™ Hand Switching Instruments, dated Dec. 2008 (2 pages).
Covidien Brochure, LigaSure Impact™ Instrument LF4318, dated Feb. 2013 (3 pages).
Covidien Brochure, The LigaSure Precise™ Instrument, dated Mar. 2011 (2 pages).
Covidien Brochure, The LigaSure™ 5 mm Blunt Tip Sealer/Divider Family, dated Apr. 2013 (2 pages).
Douglas, S.C. "Introduction to Adaptive Filter". Digital Signal Processing Handbook. Ed. Vijay K. Madisetti and Douglas B. Williams. Boca Raton: CRC Press LLC, 1999.
Erbe Electrosurgery VIO® 200 S, (2012), p. 7, 12 pages, accessed Mar. 31, 2014 at http://www.erbe-med.com/erbe/media/Marketingmaterialien/85140-170_ERBE_EN_VIO_200_S D027541.
Gibson, "Magnetic Refrigerator Successfully Tested," U.S. Department of Energy Research News, accessed online on Aug. 6, 2010 at http://www.eurekalert.org/features/doe/2001-11/dl-mrs062802.php (Nov. 1, 2001).
Glaser and Subak-Sharpe, Integrated Circuit Engineering, Addison-Wesley Publishing, Reading, MA (1979).
Harris et al., "Altered Mechanical Behavior of Epicardium Due to Isothermal Heating Under Biaxial Isotonic Loads," Journal of Biomechanical Engineering, vol. 125, pp. 381-388 (Jun. 2003).
Harris et al., "Kinetics of Thermal Damage to a Collagenous Membrane Under Biaxial Isotonic Loading," IEEE Transactions on Biomedical Engineering, vol. 51, No. 2, pp. 371-379 (Feb. 2004).
Hayashi et al., "The Effect of Thermal Heating on the Length and Histologic Properties of the Glenohumeral Joint Capsule," American Journal of Sports Medicine, vol. 25, Issue 1, 11 pages (Jan. 1997), URL: http://www.mdconsult.com/das/article/body/156183648-2/jorg=journal&source=MI&sp=1 . . . , accessed Aug. 25, 2009.
Henriques. F.C., "Studies in thermal injury V. The predictability and the significance of thermally induced rate processes leading to irreversible epidermal injury." Archives of Pathology, 434, pp. 489-502 (1947).
Hörmann et al., "Reversible and irreversible denaturation of collagen fibers." Biochemistry, 10, pp. 932-937 (1971).
Humphrey, J.D., "Continuum Thermomechanics and the Clinical Treatment of Disease and Injury," Appl. Mech. Rev., vol. 56, No. 2 pp. 231-260 (Mar. 2003).
Jang, J. et al. "Neuro-fuzzy and Soft Computing." Prentice Hall, 1997, pp. 13-89, 199-293, 335-393,453-496, 535-549.
Kurt Gieck & Reiner Gieck, Engineering Formulas § Z.7 (7th ed. 1997).
Lee et al., "A multi-sample denaturation temperature tester for collagenous biomaterials," Med. Eng. Phy., vol. 17, No. 2, pp. 115-121 (Mar. 1995).
Moran et al., "Thermally Induced Shrinkage of Joint Capsule," Clinical Orthopaedics and Related Research, No. 281, pp. 248-255 (Dec. 2000).
National Semiconductors Temperature Sensor Handbook—http://www.national.com/appinfo/tempsensors/files/temphb.pdf; accessed online: Apr. 1, 2011.
Sullivan, "Cost-Constrained Selection of Strand Diameter and Number in a Litz-Wire Transformer Winding," IEEE Transactions on Power Electronics, vol. 16, No. 2, Mar. 2001, pp. 281-288.
Sullivan, "Optimal Choice for Number of Strands in a Litz-Wire Transformer Winding," IEEE Transactions on Power Electronics, vol. 14, No. 2, Mar. 1999, pp. 283-291.
Wall et al., "Thermal modification of collagen," J Shoulder Elbow Surg, No. 8, pp. 339-344 (Jul./Aug. 1999).
Weir, C.E., "Rate of shrinkage of tendon collagen—heat, entropy and free energy of activation of the shrinkage of untreated tendon. Effect of acid salt, pickle, and tannage on the activation of tendon collagen." Journal of the American Leather Chemists Association, 44, pp. 108-140 (1949).
Wells et al., "Altered Mechanical Behavior of Epicardium Under Isothermal Biaxial Loading," Transactions of the ASME, Journal of Biomechanical Engineering, vol. 126, pp. 492-497 (Aug. 2004).
Wright, et al., "Time-Temperature Equivalence of Heat-Induced Changes in Cells and Proteins," Feb. 1998. ASME Journal of Biomechanical Engineering, vol. 120, pp. 22-26.
U.S. Appl. No. 14/218,558, filed Mar. 18, 2014.
U.S. Appl. No. 14/227,699, filed Mar. 27, 2014.
U.S. Appl. No. 14/227,708, filed Mar. 27, 2014.

* cited by examiner

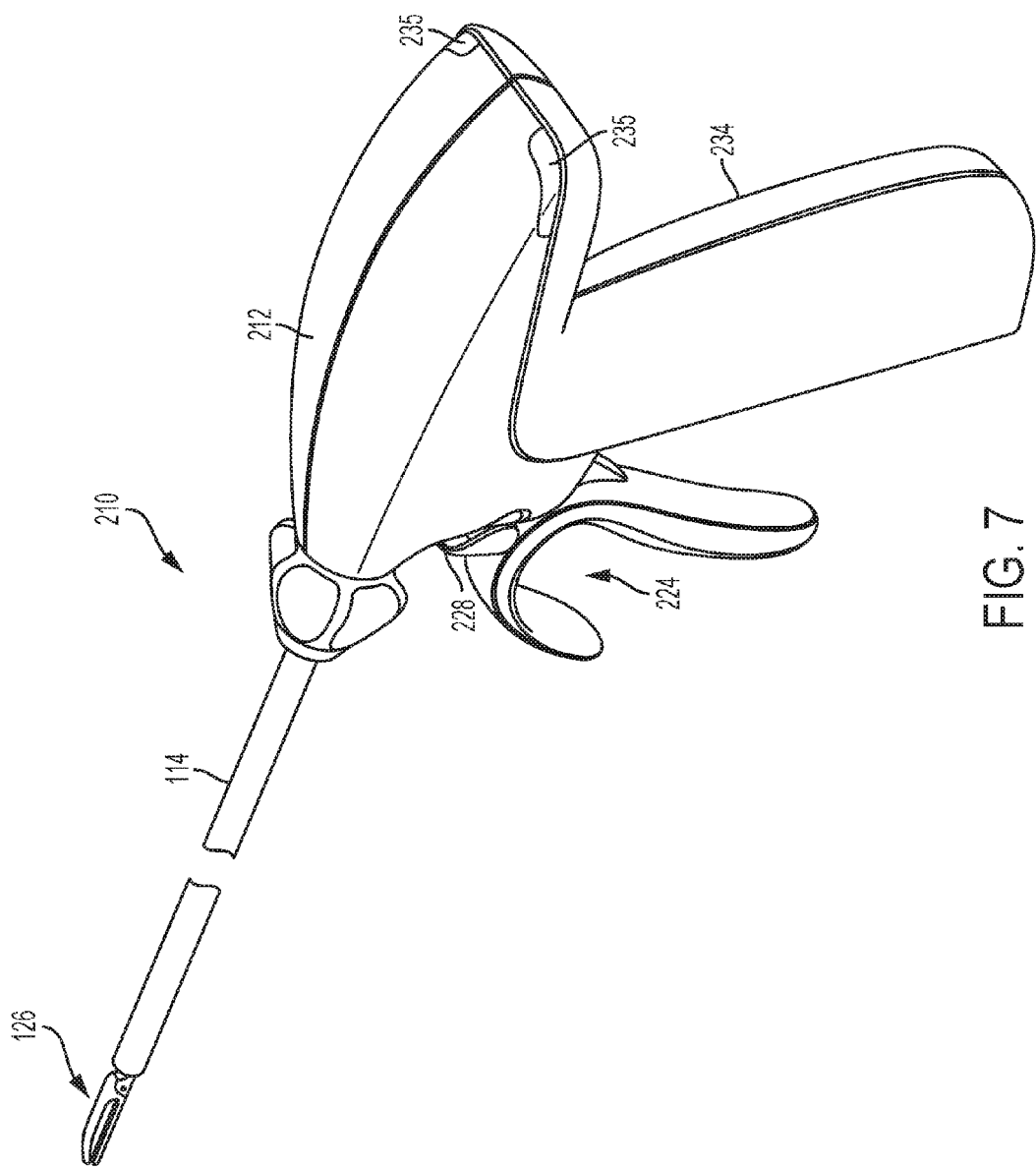

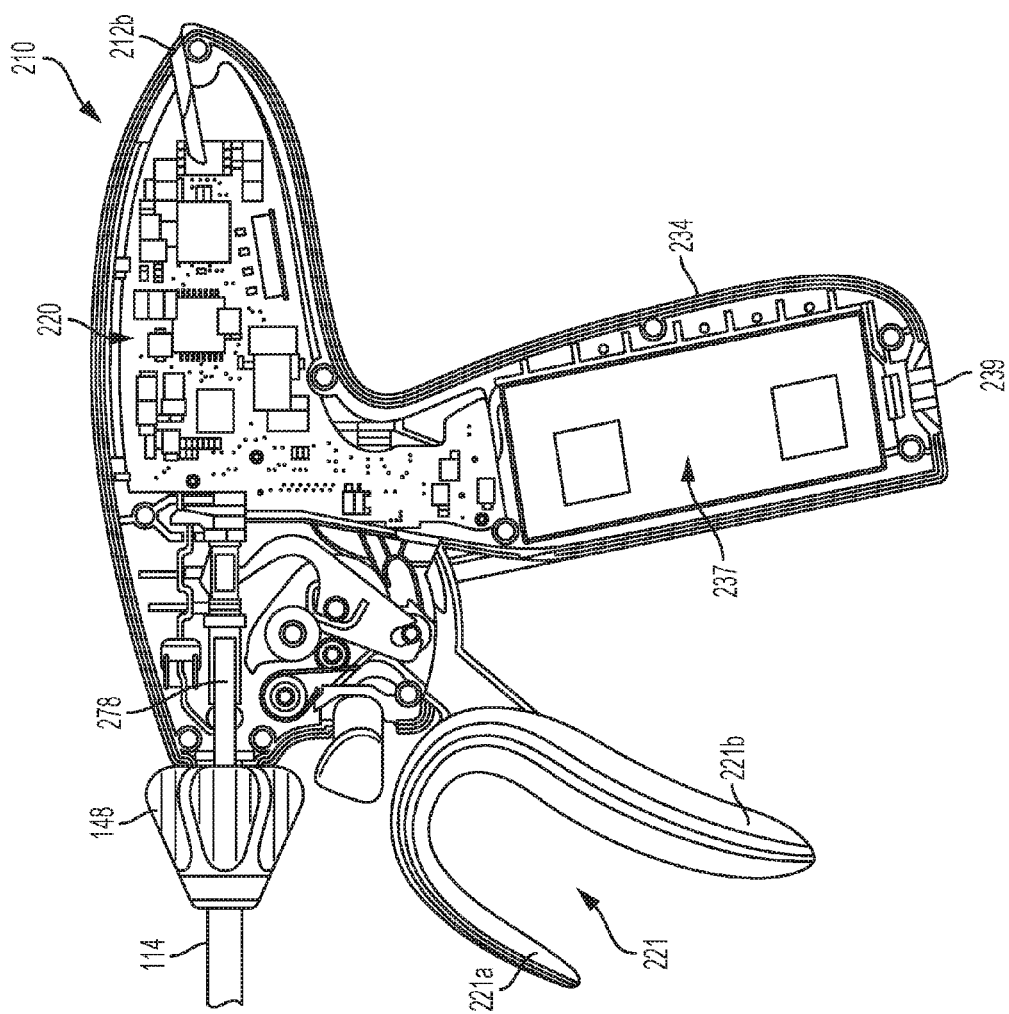

MULTI-FUNCTION BI-POLAR FORCEPS

CROSS-REFERENCE TO RELATED APPLICATIONS

This application claims benefit under 35 U.S.C. §119(e) to U.S. Provisional Patent Application 61/707,030, filed on Sep. 28, 2012, and entitled "MULTI-FUNCTION BI-POLAR FORCEPS," which is hereby incorporated by reference in its entirety.

BACKGROUND

Electrosurgical devices are used in many surgical operations. Electrosurgical devices apply electrical energy to tissue in order to treat tissue. An electrosurgical device may comprise an instrument having a distally-mounted end effector comprising one or more electrodes. The end effector can be positioned against tissue such that electrical current is introduced into the tissue. Electrosurgical devices can be configured for bipolar or monopolar operation. During bipolar operation, current is introduced into and returned from the tissue by active and return electrodes, respectively, of the end effector. During monopolar operation, current is introduced into the tissue by an active (or source) electrode of the end effector and returned through a return electrode (e.g., a grounding pad) separately located on a patient's body. Heat generated by the current flow through the tissue may form hemostatic seals within the tissue and/or between tissues and thus may be particularly useful for sealing blood vessels, for example. The end effector of an electrosurgical device may further comprise a cutting member that is movable relative to the tissue and the electrodes to transect the tissue.

Electrical energy applied by an electrosurgical device can be transmitted to the instrument by a generator. The electrical energy may be in the form of radio frequency ("RF") energy. RF energy is a form of electrical energy that may be in the frequency range of 100 kHz to 1 MHz. During its operation, an electrosurgical device can transmit low frequency RF energy through tissue, which causes ionic agitation, or friction, in effect resistive heating, thereby increasing the temperature of the tissue. Because a sharp boundary may be created between the affected tissue and the surrounding tissue, surgeons can operate with a high level of precision and control, without sacrificing un-targeted adjacent tissue. The low operating temperatures of RF energy may be useful for removing, shrinking, or sculpting soft tissue while simultaneously sealing blood vessels. RF energy may work particularly well on connective tissue, which is primarily comprised of collagen and shrinks when contacted by heat.

SUMMARY

In various embodiments, an end effector is disclosed. The end effector includes a first jaw member. The first jaw member comprises a first electrode. The first jaw member defines a first aperture at a distal end. The end effector includes a second jaw member. The second jaw member comprises a second electrode. The second jaw member defines a second aperture at a distal end. The second jaw member is operatively coupled to the first jaw member. The first and second apertures are configured to define a single aperture when the first and second jaw members are in a closed position. The first and second electrodes are configured to deliver energy.

In various embodiments, an end effector is disclosed. The end effector includes a first jaw member. The first jaw member comprises a first proximal contact surface and a first distal contact surface. The first proximal contact surface and the first distal contact surface define a first opening therebetween. The end effector includes a second jaw member comprising a second proximal contact surface and a second distal contact surface. The second jaw member is operatively coupled to the first jaw member. The second proximal contact surface and the second distal contact surface define a second opening therebetween. When the first and second jaw members are in a closed position, the first and second openings define an aperture. A first proximal electrode is coupled to the first proximal contact surface. The first proximal electrode is configured to deliver energy.

In various embodiments, an end effector is disclosed. The end effector includes a first jaw member operatively coupled to a second jaw member. The first and second jaw members each comprise a proximal contact region defined by a first width and a distal contact region defined by a second width. The first width is greater than the second width. A first electrode is coupled to the first jaw member. The first electrode is configured to deliver energy In various embodiments, an end effector is disclosed. The end effector comprises a first jaw member. The first jaw member comprises a band electrode coupled to an outer surface of the first jaw member. The band electrode is configured to lay flush with the first jaw member in a first position. The band electrode is configured to flex outwardly from the first jaw member in a second position. The band electrode is configured to deliver energy. A second jaw member is operatively coupled to the first jaw member.

FIGURES

The features of the various embodiments are set forth with particularity in the appended claims. The various embodiments, however, both as to organization and methods of operation, together with advantages thereof, may best be understood by reference to the following description, taken in conjunction with the accompanying drawings as follows:

FIG. 7 illustrates a perspective view of one embodiment of a cordless electrical energy surgical instrument.

FIG. 8A illustrates a side view of a handle of one embodiment of the surgical instrument of FIG. 7 with half of the handle body removed to illustrate various components therein.

DESCRIPTION

Reference will now be made in detail to several embodiments, including embodiments showing example implementations of electrosurgical medical instruments for cutting and coagulating tissue. Wherever practicable similar or like reference numbers may be used in the figures and may indicate similar or like functionality. The figures depict example embodiments of the disclosed surgical instruments and/or methods of use for purposes of illustration only. One skilled in the art will readily recognize from the following description that alternative example embodiments of the structures and methods illustrated herein may be employed without departing from the principles described herein.

Figure 1:
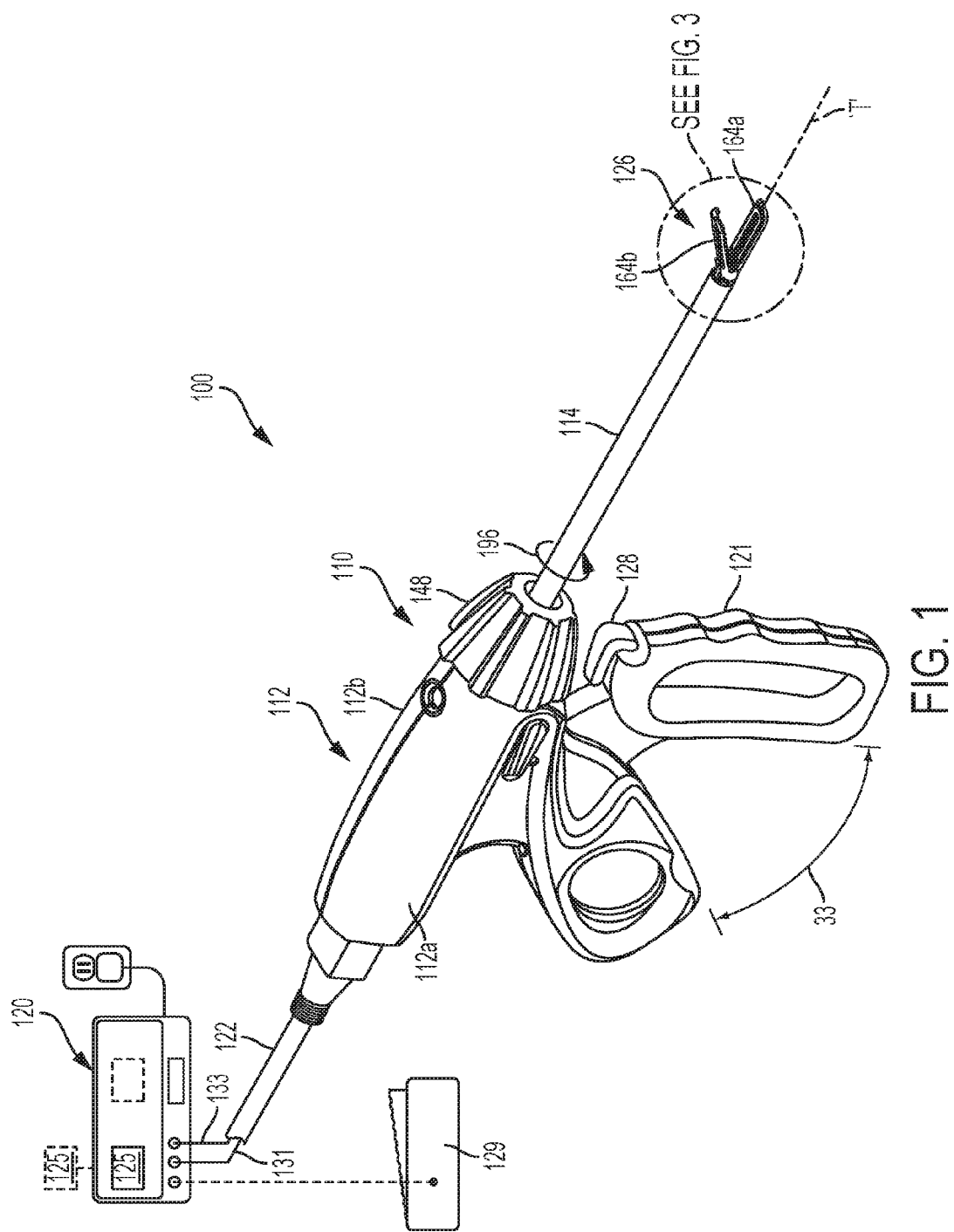
FIG. 1 illustrates a perspective view of one embodiment of an electrical energy surgical instrument.

Various embodiments of surgical instruments that utilize therapeutic and/or subtherapeutic electrical energy to treat tissue or provide feedback to the generators (e.g., electrosurgical instruments) are disclosed. The embodiments are adapted for use in a manual or hand-operated manner, although electrosurgical instruments may be utilized in robotic applications as well. FIG. 1 is a perspective view of one example embodiment of a surgical instrument system 100 comprising an electrical energy surgical instrument 110. The electrosurgical instrument 110 may comprise a proximal handle 112, a distal working end or end effector 126 and an introducer or elongated shaft 114 disposed in-between.

The electrosurgical system 100 can be configured to supply energy, such as electrical energy, ultrasonic energy, heat energy, or any combination thereof, to the tissue of a patient either independently or simultaneously, for example. In one example embodiment, the electrosurgical system 100 includes a generator 120 in electrical communication with the electrosurgical instrument 110. The generator 120 is connected to the electrosurgical instrument 110 via a suitable transmission medium such as a cable 122. In one example embodiment, the generator 120 is coupled to a controller, such as a control unit 125, for example. In various embodiments, the control unit 125 may be formed integrally with the generator 120 or may be provided as a separate circuit module or device electrically coupled to the generator 120 (shown in phantom to illustrate this option). Although in the presently disclosed embodiment, the generator 120 is shown separate from the electrosurgical instrument 110, in one example embodiment, the generator 120 (and/or the control unit 125) may be formed integrally with the electrosurgical instrument 110 to form a unitary electrosurgical system 100, where a battery located within the electrosurgical instrument 110 is the energy source and a circuit coupled to the battery produces the suitable electrical energy, ultrasonic energy, or heat energy. One such example is described herein below in connection with FIGS. 7-8C.

The generator 120 may comprise an input device 135 located on a front panel of the generator 120 console. The input device 135 may comprise any suitable device that generates signals suitable for programming the operation of the generator 120, such as a keyboard, or input port, for example. In one example embodiment, various electrodes in the first jaw 164a and the second jaw 164b may be coupled to the generator 120. The cable 122 may comprise multiple electrical conductors for the application of electrical energy to positive (+) and negative (−) electrodes of the electrosurgical instrument 110. The control unit 125 may be used to activate the generator 120, which may serve as an electrical source. In various embodiments, the generator 120 may comprise an RF source, an ultrasonic source, a direct current source, and/or any other suitable type of electrical energy source, for example, which may be activated independently or simultaneously.

In various embodiments, the electrosurgical system 100 may comprise at least one supply conductor 131 and at least one return conductor 133, wherein current can be supplied to the electrosurgical instrument 100 via the supply conductor 131 and wherein the current can flow back to the generator 120 via the return conductor 133. In various embodiments, the supply conductor 131 and the return conductor 133 may comprise insulated wires and/or any other suitable type of conductor. In certain embodiments, as described below, the supply conductor 131 and the return conductor 133 may be contained within and/or may comprise the cable 122 extending between, or at least partially between, the generator 120 and the end effector 126 of the electrosurgical instrument 110. In any event, the generator 120 can be configured to apply a sufficient voltage differential between the supply conductor 131 and the return conductor 133 such that sufficient current can be supplied to the end effector 126.

Figure 2:
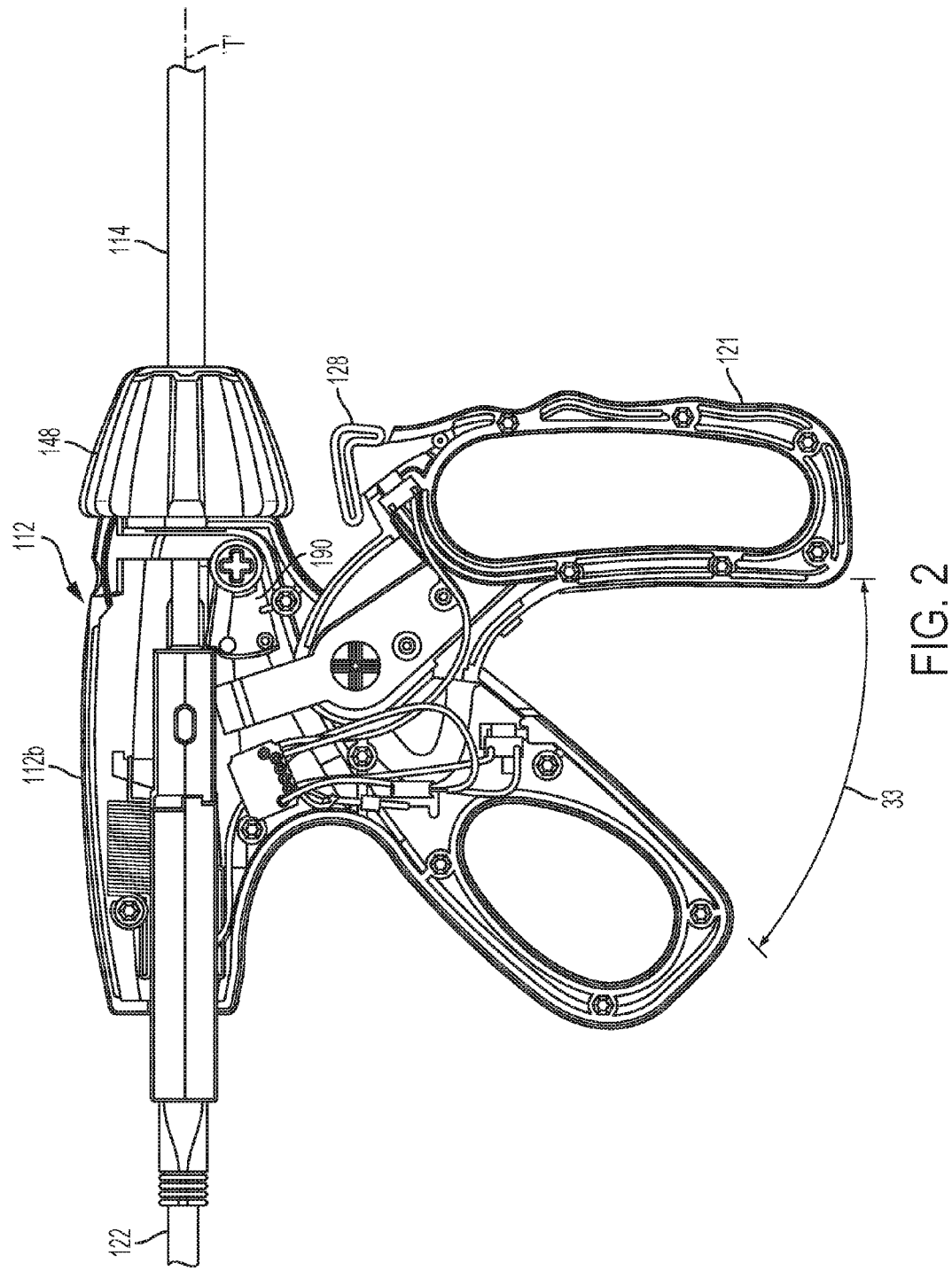
FIG. 2 illustrates a side-view of a handle of one embodiment of the surgical instrument of FIG. 1 with a half of a handle body removed to illustrates some of the components therein.

FIG. 2 is a side view of one example embodiment of the handle 112 of the surgical instrument 110. In FIG. 2, the handle 112 is shown with half of a first handle body 112a (see FIG. 1) removed to illustrate various components within the second handle body 112b. The handle 112 may comprise a lever arm 121 (e.g., a trigger) which may be pulled along a path 33. The lever arm 121 may be coupled to an axially moveable member 178 (FIGS. 3-6) disposed within the elongated shaft 114 by a shuttle 184 operably engaged to an extension 198 of lever arm 121. The shuttle 184 may further be connected to a biasing device, such as a spring 188, which may also be connected to the second handle body 112b, to bias the shuttle 184 and thus the axially moveable member 178 in a proximal direction, thereby urging the jaws 164a and 164b to an open position as seen in FIG. 1. Also, referring to FIGS. 1-2, a locking member 190 (see FIG. 2) may be moved by a locking switch 128 (see FIG. 1) between a locked position, where the shuttle 184 is substantially prevented from moving distally as illustrated, and an unlocked position, where the shuttle 184 may be allowed to freely move in the distal direction, toward the elongated shaft 114. The handle 112 can be any type of pistol-grip or other type of handle known in the art that is configured to carry actuator levers, triggers or sliders for actuating the first jaw 164a and the second jaw 164b. In some embodiments, the handle 112 may comprise a pencil-style handle. The elongated shaft 114 may have a cylindrical or rectangular cross-section, for example, and can comprise a thin-wall tubular sleeve that extends from handle 112. The elongated shaft 114 may include a bore extending therethrough for carrying actuator mechanisms, for example, the axially moveable member 178, for actuating the jaws and for carrying electrical leads for delivery of electrical energy to electrosurgical components of the end effector 126.

The end effector 126 may be adapted for capturing and transecting tissue and for contemporaneously welding the captured tissue with controlled application of energy (e.g., RF energy). The first jaw 164a and the second jaw 164b may close to thereby capture or engage tissue about a longitudinal axis "T" defined by the axially moveable member 178. The first jaw 164a and second jaw 164b may also apply compression to the tissue. In some embodiments, the elongated shaft 114, along with the first jaw 164a and second jaw 164b, can be rotated a full 360° degrees, as shown by the arrow 196 (see FIG. 1), relative to the handle 112. For example, a rotation knob 148 may be rotatable about the longitudinal axis of the shaft 114 and may be coupled to the shaft 114 such that rotation of the knob 148 causes corresponding rotation of the shaft 114. The first jaw 164a and the second jaw 164b can remain openable and/or closeable while rotated.

Figure 3:
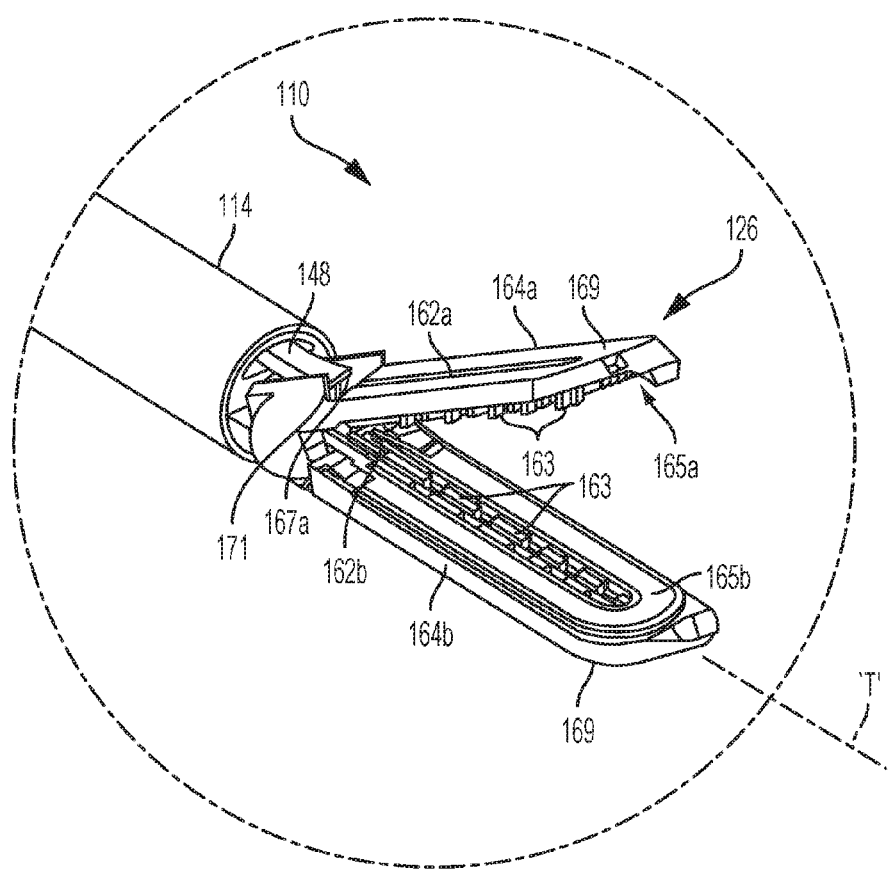
FIG. 3 illustrates a perspective view of one embodiment of the end effector of the surgical instrument of FIG. 1 with the jaws open and the distal end of an axially movable member in a retracted position.
Figure 4:
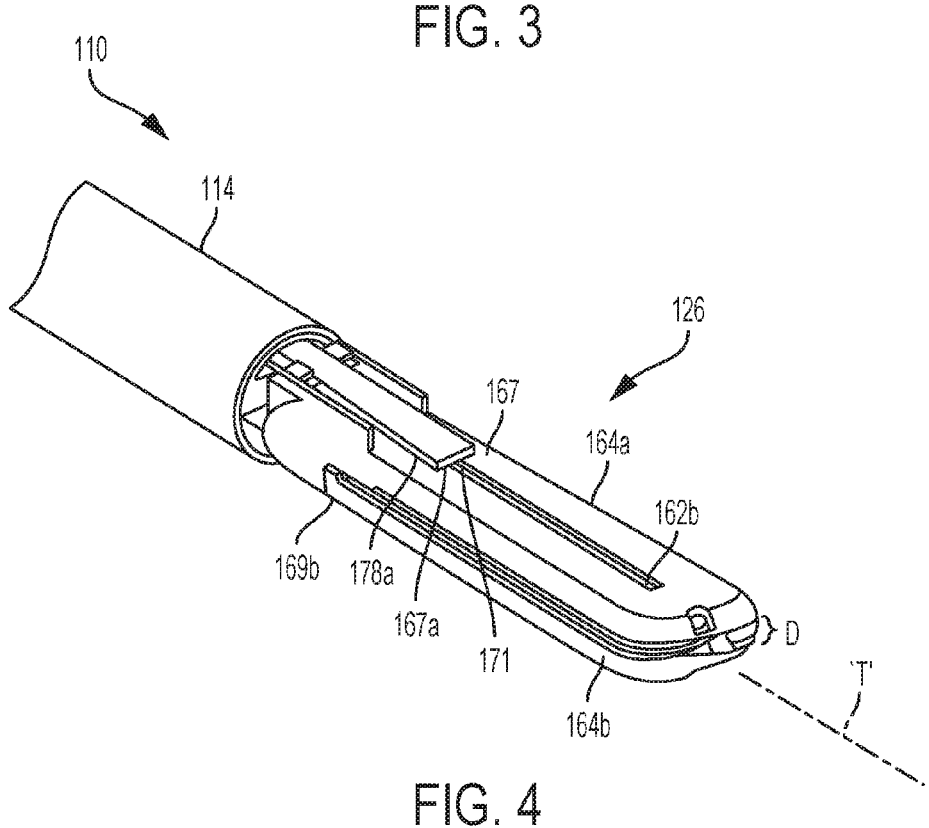
FIG. 4 illustrates a perspective view of one embodiment of the end effector of the surgical instrument of FIG. 1 with the jaws closed and the distal end of an axially moveable member in a partially advanced position.

FIG. 3 shows a perspective view of one example embodiment of the end effector 126 with the jaws 164a, 164b open, while FIG. 4 shows a perspective view of one embodiment of the end effector 126 with the jaws 164a, 164b closed. As noted above, the end effector 126 may comprise the upper first jaw 164a and the lower second jaw 164b, which may be straight or curved. The first jaw 164a and the second jaw 164b may each comprise an elongated slot or channel 162a and 162b, respectively, disposed outwardly along their respective middle portions. Further, the first jaw 164a and the second jaw 164b may each have tissue-gripping elements, such as teeth 163, disposed on the inner portions of the first jaw 164a and the second jaw 164b. The first jaw 164a may comprise an upper first jaw body 162a with an upper first outward-facing surface and an upper first energy delivery surface 165a. The second jaw 164b may comprise a lower second jaw body 162b with a lower second outward-facing surface and a lower second energy delivery surface 165b. The first energy delivery surface 165a and the second energy delivery surface 165b may both extend in a "U" shape about the distal end of the end effector 126.

Figure 5:
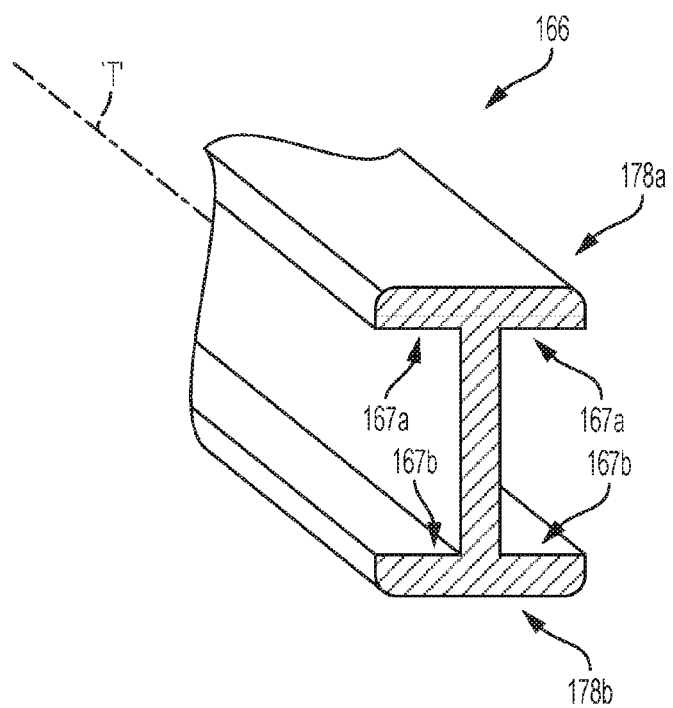
FIG. 5 illustrates a perspective view of one embodiment of the axially moveable member of the surgical instrument of FIG. 1.

The lever arm 121 of the handle 112 (FIG. 2) may be adapted to actuate the axially moveable member 178, which also may function as a jaw-closing mechanism. For example, the axially moveable member 178 may be urged distally as the lever arm 121 is pulled proximally along the path 33 via the shuttle 184, as shown in FIG. 2 and discussed above. FIG. 5 is a perspective view of one example embodiment of the axially moveable member 178 of the surgical instrument 110. The axially moveable member 178 may comprise one or several pieces, but in any event, may be movable or translatable with respect to the elongated shaft 114 and/or the jaws 164a, 164b. Also, in at least one example embodiment, the axially moveable member 178 may be made of 17-4 precipitation hardened stainless steel. The distal end of axially moveable member 178 may comprise a flanged "I"-beam configured to slide within the channels 162a and 162b in jaws 164a and 164b. The axially moveable member 178 may slide within the channels 162a, 162b to open and close the first jaw 164a and the second jaw 164b. The distal end of the axially moveable member 178 may also comprise an upper flange or "c"-shaped portion 178a and a lower flange or "c"-shaped portion 178b. The flanges 178a, 178b respectively define inner cam surfaces 167a and 167b for engaging outward facing surfaces of the first jaw 164a and the second jaw 164b. The opening-closing of jaws 164a and 164b can apply very high compressive forces on tissue using cam mechanisms which may include movable "I-beam" axially moveable member 178 and the outward facing surfaces 169a, 169b of jaws 164a, 164b.

More specifically, referring now to FIGS. 3-5, collectively, the inner cam surfaces 167a and 167b of the distal end of axially moveable member 178 may be adapted to slideably engage the first outward-facing surface 369a and the second outward-facing surface 169b of the first jaw 164a and the second jaw 164b, respectively. The channel 162a within first jaw 164a and the channel 162b within the second jaw 164b may be sized and configured to accommodate the movement of the axially moveable member 178, which may comprise a tissue-cutting element 171, for example, comprising a sharp distal edge. FIG. 4, for example, shows the distal end of the axially moveable member 178 advanced at least partially through channels 162a and 162b (FIG. 3). The advancement of the axially moveable member 178 may close the end effector 126 from the open configuration shown in FIG. 3. In the closed position shown by FIG. 4, the upper first jaw 164a and the lower second jaw 164b define a gap or dimension D between the first energy delivery surface 165a and second energy delivery surface 165b of the first jaw 164a and the second jaw 164b, respectively. In various embodiments, dimension the D can equal from about 0.0005" to about 0.040", for example, and in some embodiments, between about 0.001" to about 0.010", for example. Also, the edges of the first energy delivery surface 165a and the second energy delivery surface 165b may be rounded to prevent the dissection of tissue.

Figure 6:
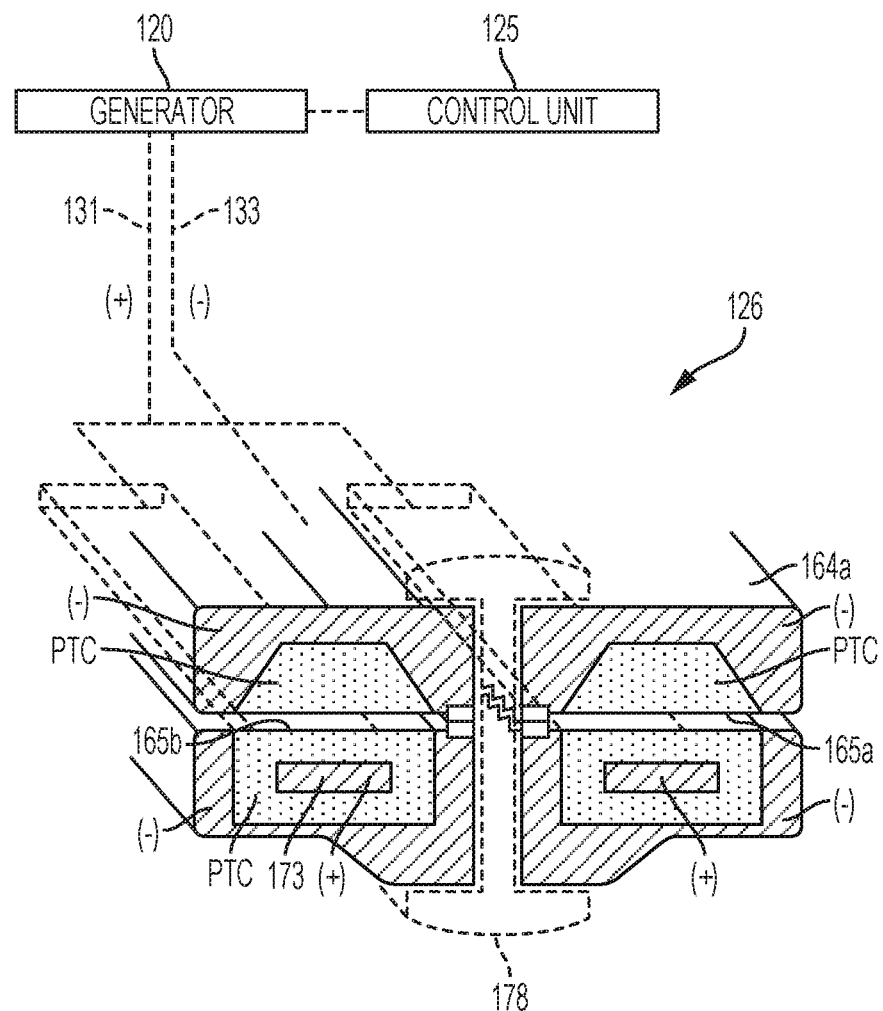
FIG. 6 illustrates a section view of one embodiment of the end effector of the surgical instrument of FIG. 1.

FIG. 6 is a section view of one example embodiment of the end effector 126 of the surgical instrument 110. The engagement, tissue-contacting, surface 165b of the lower jaw 164b is adapted to deliver energy to tissue, at least in part, through a conductive-resistive matrix, such as a variable resistive PTC body, as discussed in more detail below. At least one of the upper and lower jaws 164a, 164b may carry at least one electrode 173 configured to deliver the energy from the generator 120 to the captured tissue. The engagement, tissue-contacting, surface 165a of the upper jaw 164a may carry a similar conductive-resistive matrix (i.e., a PTC material), or in some embodiments the surface may be a conductive electrode or an insulative layer, for example. Alternatively, the engagement surfaces of the jaws can carry any of the energy delivery components disclosed in U.S. Pat. No. 6,773,409, filed Oct. 22, 2001, entitled ELECTROSURGICAL JAW STRUCTURE FOR CONTROLLED ENERGY DELIVERY, the entire disclosure of which is incorporated herein by reference.

The first energy delivery surface 165a and the second energy delivery surface 165b each may be in electrical communication with the generator 120. The first energy delivery surface 165a and the second energy delivery surface 165b may be configured to contact tissue and deliver electrosurgical energy to captured tissue which are adapted to seal or weld the tissue. The control unit 125 regulates the electrical energy delivered by electrical generator 120 which in turn delivers electrosurgical energy to the first energy delivery surface 165a and the second energy delivery surface 165b. The energy delivery may be initiated by an activation button 128 (FIG. 2) operably engaged with the lever arm 121 and in electrical communication with the generator 120 via a cable 122. In one example embodiment, the electrosurgical instrument 110 may be energized by the generator 120 by way of a foot switch 129 (FIG. 1). When actuated, the foot switch 129 triggers the generator 120 to deliver electrical energy to the end effector 126, for example. The control unit 125 may regulate the power generated by the generator 120 during activation. Although the foot switch 129 may be suitable in many circumstances, other suitable types of switches can be used, such as, for example, a thumb switch.

As mentioned above, the electrosurgical energy delivered by electrical generator 120 and regulated, or otherwise controlled, by the control unit 125 may comprise radio frequency (RF) energy, or other suitable forms of electrical energy. Further, the opposing first and second energy delivery surfaces 165a and 165b may carry variable resistive PTC bodies that are in electrical communication with the generator 120 and the control unit 125. Additional details regarding electrosurgical end effectors, jaw closing mechanisms, and electrosurgical energy-delivery surfaces are described in the following U.S. patents and published patent applications: U.S. Pat. Nos. 7,087,054; 7,083,619; 7,070,597; 7,041,102; 7,011,657; 6,929,644; 6,926,716; 6,913,579; 6,905,497; 6,802,843; 6,770,072; 6,656,177; 6,533,784; and 6,500,112; and U.S. Pat. App. Pub. Nos. 2010/0036370 and 2009/0076506, all of which are incorporated herein by reference in their entirety and made part of this specification.

In one example embodiment, the generator 120 may be implemented as an electrosurgery unit (ESU) capable of supplying power sufficient to perform bipolar electrosurgery using radio frequency (RF) energy. In one example embodiment, the ESU can be a bipolar ERBE ICC 150 sold by ERBE USA, Inc. of Marietta, Ga. In some embodiments, such as for bipolar electrosurgery applications, a surgical instrument having an active electrode and a return electrode can be utilized, wherein the active electrode and the return electrode can be positioned against, adjacent to and/or in electrical communication with, the tissue to be treated such that current can flow from the active electrode, through the PTC bodies and to the return electrode through the tissue. Thus, in various embodiments, the electrosurgical system 100 may comprise a supply path and a return path, wherein the captured tissue being treated completes, or closes, the circuit. In one example embodiment, the generator 120 may be a monopolar RF ESU and the electrosurgical instrument 110 may comprise a monopolar end effector 126 in which one or more active electrodes are integrated. For such a system, the generator 120 may require a return pad in intimate contact with the patient at a location remote from the operative site and/or other suitable return path. The return pad may be connected via a cable to the generator 120. In other embodiments, the operator may provide sub-therapeutic RF energy levels for purposes of evaluating tissue conditions and providing feedback in the electrosurgical system 100. Such feed back may be employed to control the therapeutic RF energy output of the electrosurgical instrument 110.

During operation of electrosurgical instrument 100, the user generally grasps tissue, supplies energy to the grasped tissue to form a weld or a seal (e.g., by actuating button 128 and/or pedal 129), and then drives a tissue-cutting element 171 at the distal end of the axially moveable member 178 through the grasped tissue. According to various embodiments, the translation of the axial movement of the axially moveable member 178 may be paced, or otherwise controlled, to aid in driving the axially moveable member 178 at a suitable rate of travel. By controlling the rate of the travel, the likelihood that the captured tissue has been properly and functionally sealed prior to transection with the cutting element 171 is increased.

FIG. 7 is a perspective view of one example embodiment of a surgical instrument system 200 comprising a cordless electrical energy surgical instrument 210. The electrosurgical system 200 is similar to the electrosurgical system 100. The electrosurgical system 200 can be configured to supply energy, such as electrical energy, ultrasonic energy, heat energy, or any combination thereof, to the tissue of a patient either independently or simultaneously as described in connection with FIG. 1, for example. The electrosurgical instrument 210 may utilize the end effector 126 and elongated shaft 114 described here in conjunction with a cordless proximal handle 212. In one example embodiment, the handle 212 includes a generator circuit 220 (see FIG. 8A). The generator circuit 220 performs a function substantially similar to that of generator 120. In one example embodiment, the generator circuit 220 is coupled to a controller, such as a control circuit. In the illustrated embodiment, the control circuit is integrated into the generator circuit 220. In other embodiments, the control circuit may be separate from the generator circuit 220.

In one example embodiment, various electrodes in the end effector 126 (including the first and second jaws 164a, 164b thereof) may be coupled to the generator circuit 220. The control circuit may be used to activate the generator 220, which may serve as an electrical source. In various embodiments, the generator 220 may comprise an RF source, an ultrasonic source, a direct current source, and/or any other suitable type of electrical energy source, for example. In one example embodiment, a button 128 may be provided to activate the generator circuit 220 to provide energy to the end effector 126.

FIG. 8A is a side view of one example embodiment of the handle 212 of the cordless surgical instrument 210. In FIG. 8A, the handle 212 is shown with half of a first handle body removed to illustrate various components within the second handle body 234. The handle 212 may comprise a lever arm 224 (e.g., a trigger) which may be pulled along a path 33 around a pivot point. The lever arm 224 may be coupled to an axially moveable member 278 disposed within the elongated shaft 114 by a shuttle operably engaged to an extension of lever arm 221. In one example embodiment, the lever arm 221 defines a shepherd's hook shape comprising a distal trigger hook 221a and a proximal trigger portion 221b. As illustrated, the distal trigger hook 221a may have a first length while the proximal trigger portion 221b may have a second length with the second length greater than the first length.

In one example embodiment, the cordless electrosurgical instrument comprises a battery 237. The battery 237 provides electrical energy to the generator circuit 220. The battery 237 may be any battery suitable for driving the generator circuit 220 at the desired energy levels. In one example embodiment, the battery 237 is a 1030 mAhr, triple-cell Lithium Ion Polymer battery. The battery may be fully charged prior to use in a surgical procedure, and may hold a voltage of about 12.6V. The battery 237 may have two fuses fitted to the cordless electrosurgical instrument 210, arranged in line with each battery terminal. In one example embodiment, a charging port 239 is provided to connect the battery 237 to a DC current source (not shown).

Figure 8B:
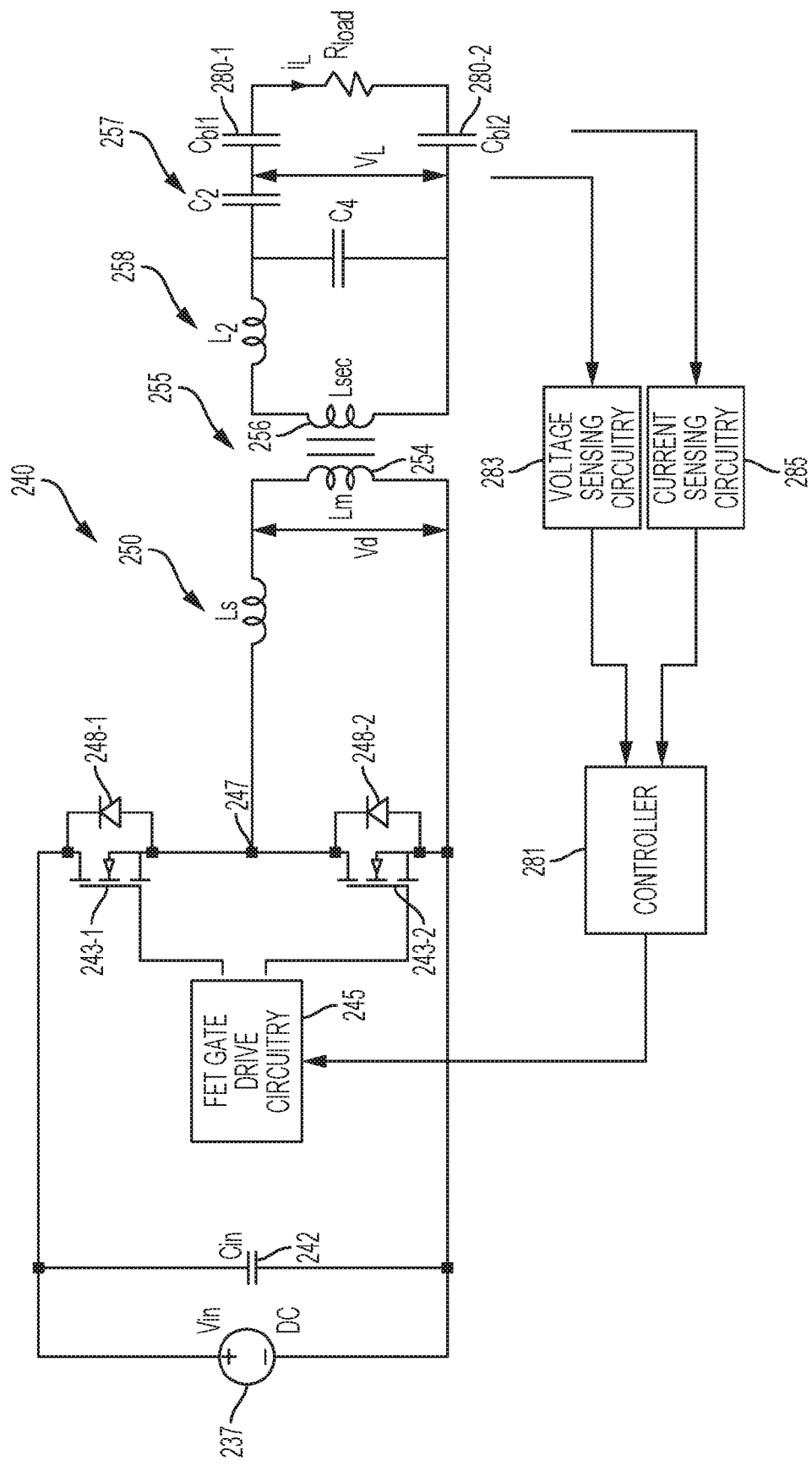
FIG. 8B illustrates one embodiment of an RF drive and control circuit.

The generator circuit 220 may be configured in any suitable manner. In some embodiments, the generator circuit comprises an RF drive and control circuit 240 and a controller circuit 282. FIG. 8B illustrates an RF drive and control circuit 240, according to one embodiment. FIG. 8B is a part schematic part block diagram illustrating the RF drive and control circuitry 240 used in this embodiment to generate and control the RF electrical energy supplied to the end effector 126. As will be explained in more detail below, in this embodiment, the drive circuitry 240 is a resonant mode RF amplifier comprising a parallel resonant network on the RF amplifier output and the control circuitry operates to control the operating frequency of the drive signal so that it is maintained at the resonant frequency of the drive circuit, which in turn controls the amount of power supplied to the end effector 126. The way that this is achieved will become apparent from the following description.

As shown in FIG. 8B, the RF drive and control circuit 240 comprises the above described battery 237 are arranged to supply, in this example, about 0V and about 12V rails. An input capacitor ($C_{in}$) 242 is connected between the 0V and the 12V for providing a low source impedance. A pair of FET switches 243-1 and 243-2 (both of which are N-channel in this embodiment to reduce power losses) is connected in series between the 0V rail and the 12V rail. FET gate drive circuitry 245 is provided that generates two drive signals—one for driving each of the two FETs 243. The FET gate drive circuitry 245 generates drive signals that causes the upper FET (243-1) to be on when the lower FET (243-2) is off and vice versa. This causes the node 247 to be alternately connected to the 12V rail (when the FET 243-1 is switched on) and the 0V rail (when the FET 243-2 is switched on). FIG. 8B also shows the internal parasitic diodes 248-1 and 248-2 of the corresponding FETs 243, which conduct during any periods that the FETs 243 are open.

As shown in FIG. 8B, the node 247 is connected to an inductor-inductor resonant circuit 250 formed by inductor $L_s$ 252 and inductor $L_m$ 254. The FET gate driving circuitry 245 is arranged to generate drive signals at a drive frequency ($f_d$) that opens and crosses the FET switches 243 at the resonant frequency of the parallel resonant circuit 250. As a result of the resonant characteristic of the resonant circuit 250, the square wave voltage at node 247 will cause a substantially sinusoidal current at the drive frequency ($f_d$) to flow within the resonant circuit 250. As illustrated in FIG. 8B, the inductor $L_m$ 254 is the primary of a transformer 255, the secondary of which is formed by inductor $L_{sec}$ 256. The inductor $L_{sec}$ 256 of the transformer 255 secondary is connected to an inductor-capacitor-capacitor parallel resonant circuit 257 formed by inductor $L_2$ 258, capacitor $C_4$ 260, and capacitor $C_2$ 262. The transformer 255 up-converts the drive voltage ($V_d$) across the inductor $L_m$ 254 to the voltage that is applied to the output parallel resonant circuit 257. The load voltage ($V_L$) is output by the parallel resonant circuit 257 and is applied to the load (represented by the load resistance $R_{load}$ 259 in FIG. 8B) corresponding to the impedance of the forceps' jaws and any tissue or vessel gripped by the end effector 126. As shown in FIG. 8B, a pair of DC blocking capacitors $C_{b1}$ 280-1 and 280-2 is provided to prevent any DC signal being applied to the load 259.

In one embodiment, the transformer 255 may be implemented with a Core Diameter (mm), Wire Diameter (mm), and Gap between secondary windings in accordance with the following specifications:

Core Diameter, D (mm)

$D=19.9\times10-3$

Wire diameter, W (mm) for 22 AWG wire $W=7.366\times10-4$

Gap between secondary windings, in gap=0.125

$G=gap/25.4$

In this embodiment, the amount of electrical power supplied to the end effector 126 is controlled by varying the frequency of the switching signals used to switch the FETs 243. This works because the resonant circuit 250 acts as a frequency dependent (loss less) attenuator. The closer the drive signal is to the resonant frequency of the resonant circuit 250, the less the drive signal is attenuated. Similarly, as the frequency of the drive signal is moved away from the resonant frequency of the circuit 250, the more the drive signal is attenuated and so the power supplied to the load reduces. In this embodiment, the frequency of the switching signals generated by the FET gate drive circuitry 245 is controlled by a controller 281 based on a desired power to be delivered to the load 259 and measurements of the load voltage ($V_L$) and of the load current ($I_L$) obtained by conventional voltage sensing circuitry 283 and current sensing circuitry 285. The way that the controller 281 operates will be described in more detail below.

In one embodiment, the voltage sensing circuitry 283 and the current sensing circuitry 285 may be implemented with high bandwidth, high speed rail-to-rail amplifiers (e.g., LMH6643 by National Semiconductor). Such amplifiers, however, consume a relatively high current when they are operational. Accordingly, a power save circuit may be provided to reduce the supply voltage of the amplifiers when they are not being used in the voltage sensing circuitry 283 and the current sensing circuitry 285. In one-embodiment, a step-down regulator (e.g., LT1502 by Linear Technologies) may be employed by the power save circuit to reduce the supply voltage of the rail-to-rail amplifiers and thus extend the life of the battery 237.

Figure 8C:
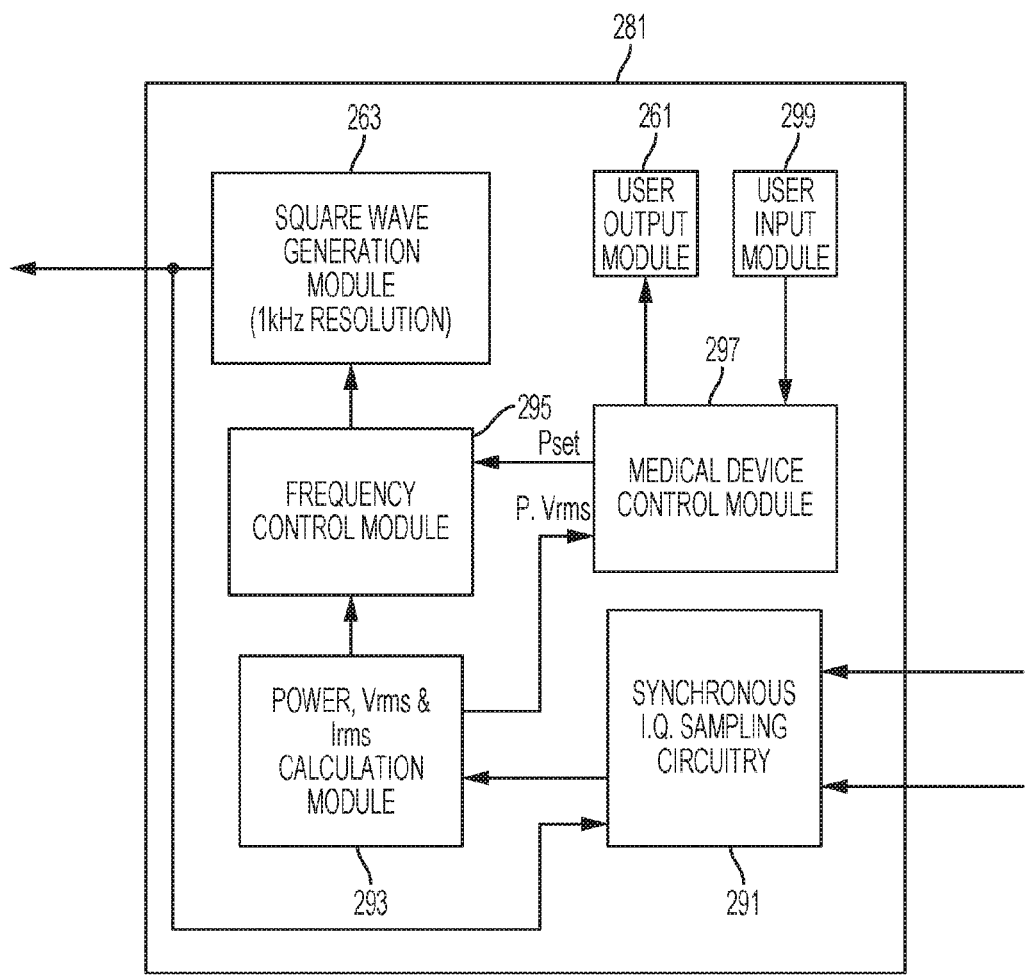
FIG. 8C illustrates one embodiment of the main components of a control circuit.

FIG. 8C illustrates the main components of the controller 281, according to one embodiment. In the embodiment illustrated in FIG. 8C, the controller 281 is a microprocessor based controller and so most of the components illustrated in FIG. 8C are software based components. Nevertheless, a hardware based controller 281 may be used instead. As shown, the controller 281 includes synchronous I,Q sampling circuitry 291 that receives the sensed voltage and current signals from the sensing circuitry 283 and 285 and obtains corresponding samples which are passed to a power, $V_{rms}$ and $I_{rms}$ calculation module 293. The calculation module 293 uses the received samples to calculate the RMS voltage and RMS current applied to the load 259 (FIG. 8B; end effector 126 and tissue/vessel gripped thereby) and from them the power that is presently being supplied to the load 259. The determined values are then passed to a frequency control module 295 and a medical device control module 297. The medical device control module 297 uses the values to determine the present impedance of the load 259 and based on this determined impedance and a pre-defined algorithm, determines what set point power ($P_{set}$) should be applied to the frequency control module 295. The medical device control module 297 is in turn controlled by signals received from a user input module 299 that receives inputs from the user (for example pressing buttons or activating the control levers 114, 110 on the handle 104) and also controls output devices (lights, a display, speaker or the like) on the handle 104 via a user output module 261.

The frequency control module 295 uses the values obtained from the calculation module 293 and the power set point ($P_{set}$) obtained from the medical device control module 297 and predefined system limits (to be explained below), to determine whether or not to increase or decrease the applied frequency. The result of this decision is then passed to a square wave generation module 263 which, in this embodiment, increments or decrements the frequency of a square wave signal that it generates by 1 kHz, depending on the received decision. As those skilled in the art will appreciate, in an alternative embodiment, the frequency control module 295 may determine not only whether to increase or decrease the frequency, but also the amount of frequency change required. In this case, the square wave generation module 263 would generate the corresponding square wave signal with the desired frequency shift. In this embodiment, the square wave signal generated by the square wave generation module 263 is output to the FET gate drive circuitry 245, which amplifies the signal and then applies it to the FET 243-1. The FET gate drive circuitry 245 also inverts the signal applied to the FET 243-1 and applies the inverted signal to the FET 243-2.

The electrosurgical instrument 210 may comprise additional features as discussed with respect to the electrosurgical system 100 illustrated in FIGS. 1-6. Those skilled in the art will recognize that electrosurgical instrument 210 may include a rotation knob 148, an elongated shaft 114, and an end effector 126. These elements function in a substantially similar manner to that discussed above with respect to the electrosurgical system 100 illustrated in FIGS. 1-6. In one example embodiment, the cordless electrosurgical instrument 210 may include visual indicators 235. The visual indicators 235 may provide a visual indication signal to an operator. In one example embodiment, the visual indication signal may alert an operator that the device is on, or that the device is applying energy to the end effector. Those skilled in the art will recognize that the visual indicators 235 may be configured to provide information on multiple states of the device.

Figure 9:
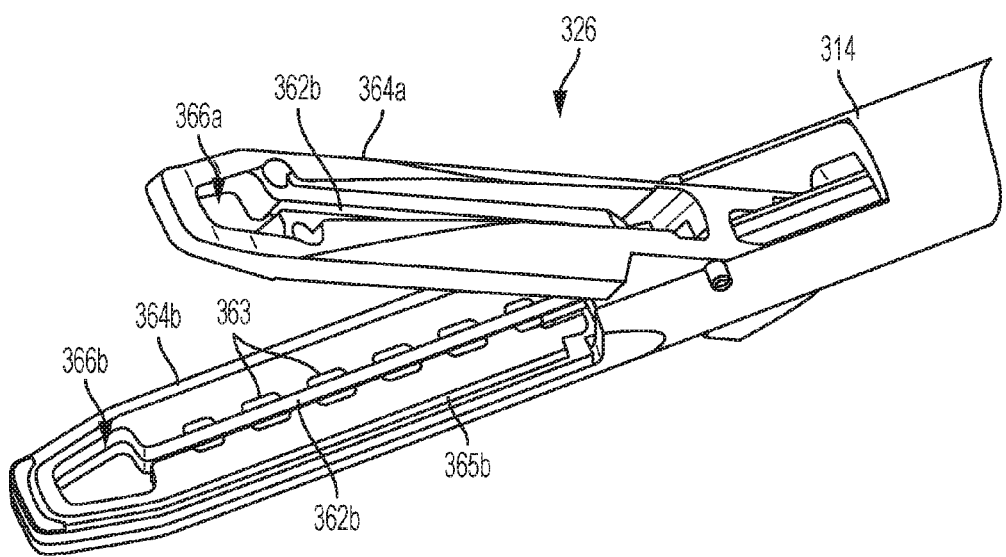
FIG. 9 illustrates one embodiment of an end effector comprising an aperture.

FIG. 9 illustrates one embodiment of an end effector 326 comprising an aperture. The end effector 326 is configured for use with an electrosurgical instrument, such as, for example, the electrosurgical instruments 110, 210 illustrated in FIGS. 1-8C. The end effector 326 comprises a first jaw member 364a and a second jaw member 364b. The first jaw member 364a comprises a first aperture 366a defined by the distal portion of the first jaw member 364a. The second jaw member 364b comprises a second aperture 366b defined by the distal portion of the second jaw member 364b. The end effector 326 is similar to the end effector 126 illustrated in FIGS. 3-5. For example, the end effector 326 may comprise one or more staples 363, I-beam channels 362a, 362b formed on both the first and second jaws 364a, 364b, and/or a cutting instrument (see FIG. 11) deployable within the channels 362a, 362b.

Figure 10:
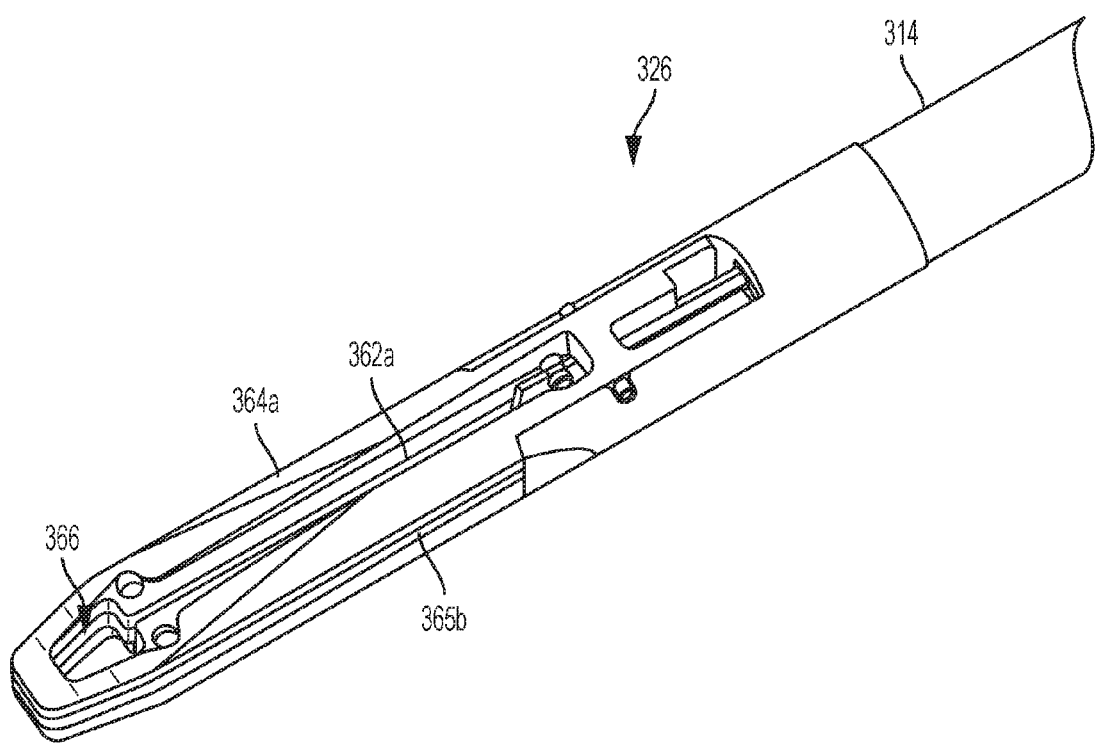
FIG. 10 illustrates a perspective view of the end effector of FIG. 9.
Figure 11:
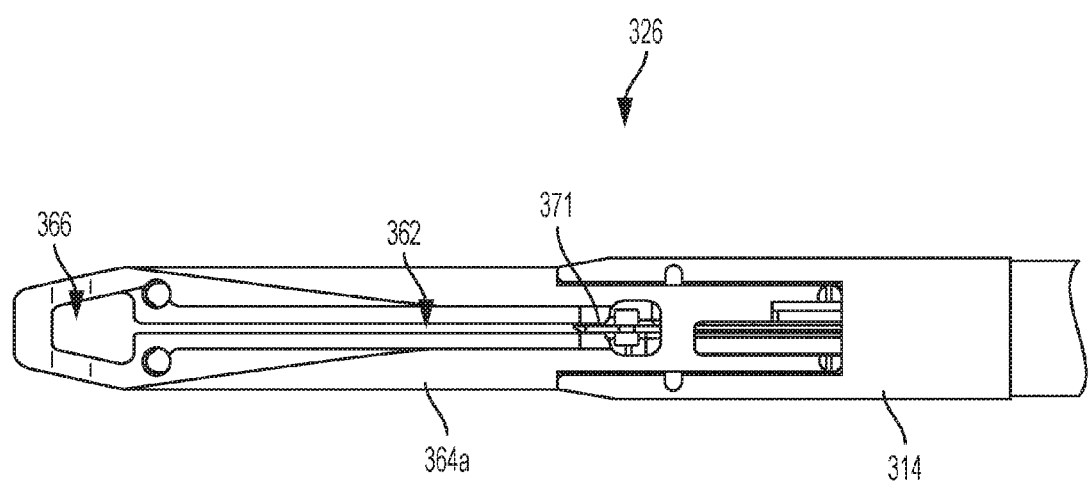
FIG. 11 illustrates a top view of the end effector of FIG. 9.

FIG. 10 illustrates the end effector 326 in a closed position. The end effector 326 is transitioned from an open position, as shown in FIG. 9, to the closed position shown in FIG. 10 by, for example, actuating one or more levers on the handle 112. When the end effector 326 is in a closed position, the first aperture 366a and the second aperture 366b align to define a single aperture 366. The aperture 366 provides improved tip grasping to the end effector 326. FIG. 11 illustrates a top-down view of the end effector 326. The distal end of the end effector 326 defining the aperture 366 is configured to grasp a material, such as, for example, tissue, before, during, and after application of energy, such as, for example, electrosurgical and/or ultrasonic energy. The end effector 326 may be referred to as a fenestrated end effector.

FIG. 11 illustrates a top view of the end effector 326 of FIG. 9. The first channel 362a and the second channel 362b align to define a longitudinal channel 362. A cutting member 371 is slideably receivable within the longitudinal channel 362. The cutting member 371 is deployable to cut tissue and/or other materials located between the first jaw member 364a and the second jaw member 364b. In some embodiments, the cutting member 371 comprises an I-Beam. FIG. 11 illustrates the alignment of the first aperture 366a and the second aperture 366b to define a single aperture 366. In some embodiments, the end effector 326 comprises a width suitable for insertion through a trocar. For example, the end effector may comprise a width of about 4.50 millimeters.

Figure 12:
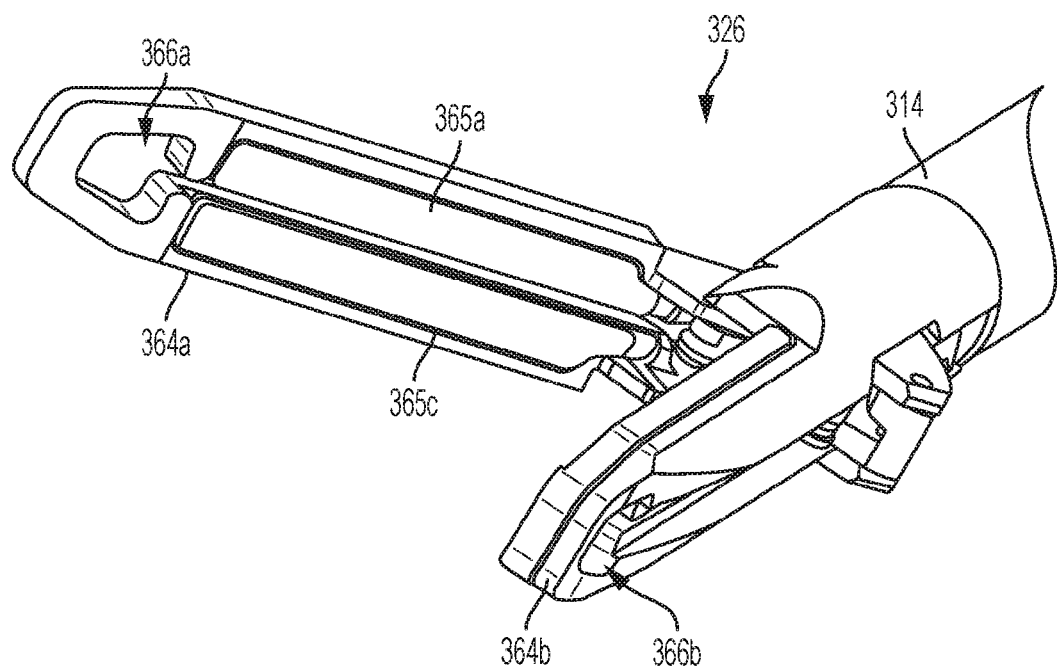
FIG. 12 illustrates one embodiment of the end effector of FIG. 9 comprising a plurality of electrodes.

FIG. 12 illustrates one embodiment of the end effector 326 comprising energy deliver surfaces, such as, for example, a first electrode 365a and a second electrode 365b. The electrodes 365a, 365b are configured to deliver energy to a tissue section grasped between the first jaw member 364a and the second jaw member 364b. The electrodes 365a, 365b may be configured to provide monopolar RF energy, bipolar RF energy, ultrasonic energy, or any combination thereof to a tissue section. In some embodiments, the electrodes 365a, 365b are configured as source electrodes and are coupled to a generator 120, for example, through a supply conductor 131. The second jaw member 364b and/or a second contact surface 365c in the second jaw member 364b may be configured as a return electrode coupled to the generator 120 through a return conductor 133. In some embodiments, the energy contact surfaces 365a-365c comprise a positive temperature coefficient (PTC) material. The PTC material may limit the energy delivered by the energy contact surfaces 365a-365c as the temperature of the energy contact surfaces 365a-365c increases during treatment. The energy contact surfaces 365a-365c may be configured to provide therapeutic RF energy, subtherapeutic RF energy, ultrasonic energy, or any combination thereof.

Figure 13A:
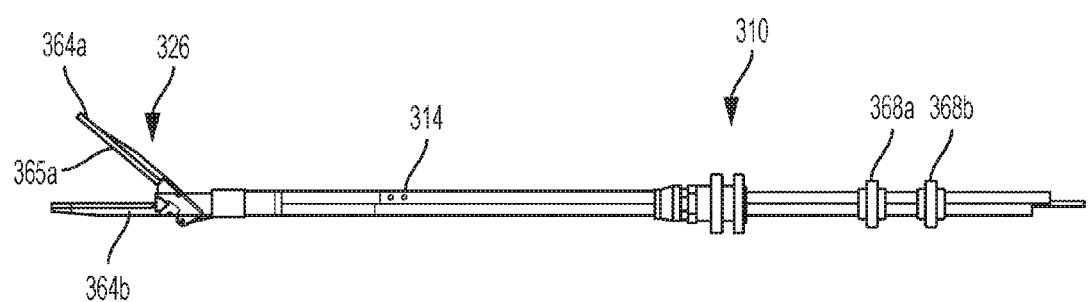
FIG. 13a illustrates one embodiment of the end effector of FIG. 9 coupled to an elongate shaft and in an open position.
Figure 13B:
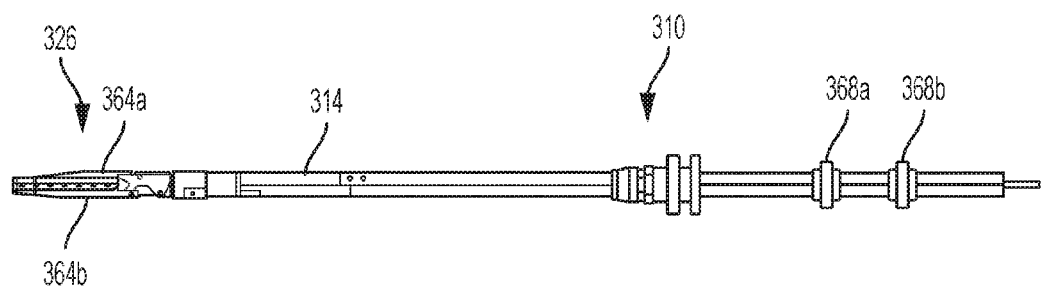
FIG. 13b illustrates one embodiment of the end effector of FIG. 13a in a closed position.

FIG. 13A illustrates one embodiment of the end effector 326 coupled to an elongate shaft 314. The end effector 326 is shown in an open position. An actuator within the elongate shaft 314 is configured to transition the end effector 326 from an open position, shown in FIG. 13a, to a closed position, as shown in FIG. 13B. In one embodiment, one or more actuators extend through the shaft 314. The one or more actuators are configured to transition the first and second jaws 364a, 364b of the end effector 326 from an open position to a closed position. In one embodiment, the one or more actuators are coupled to one or more actuation handles 368a, 368b. A first actuation handle 368a is moved from a first position, shown in FIG. 13A, to a second position, shown in FIG. 13B. The movement of the first actuation handle 368a causes the first jaw member 364a to transition to a closed position. A second actuator handle 368b may be configured, for example, to advance a cutting instrument 371 into the longitudinal channel 362.

In operation, the end effector 326 is positioned by a surgeon at a surgical site. The end effector 326 is positioned through, for example, endoscopic, laparoscopic, or open surgery techniques. A surgeon positions a tissue section between the first jaw member 364a and the second jaw member 364b. The surgeon operates an actuator, such as, for example, a trigger coupled to handle or a first actuation ring 368a coupled to the elongate shaft 314, to cause the first jaw member 364a to rotate or transition to a closed position to grasp the tissue section between the first jaw member 364a and the second jaw member 364b. In some embodiments, the end effector 326 comprises an energy delivery surface, such as, for example, one or more electrodes 365a, 365b configured to deliver energy. The surgeon may activate delivery of energy to the electrodes 365a, 365b. The electrodes 365a, 365b deliver the energy to the tissue section grasped between the first jaw member 364a and the second jaw member 364b. The delivered energy may weld, cauterize, dissect, and/or otherwise treat the tissue section. In some embodiments, the first jaw member 364a defines a first channel 362a and the second jaw member 364b defines a second channel 362b. The first and second channels 362a, 362b define a longitudinal channel 362. A cutting member 371 is slideably receivable within the longitudinal channel 362. The cutting member 371 is deployable to cut the tissue section before, during, or after treatment of the tissue.

Figure 14:
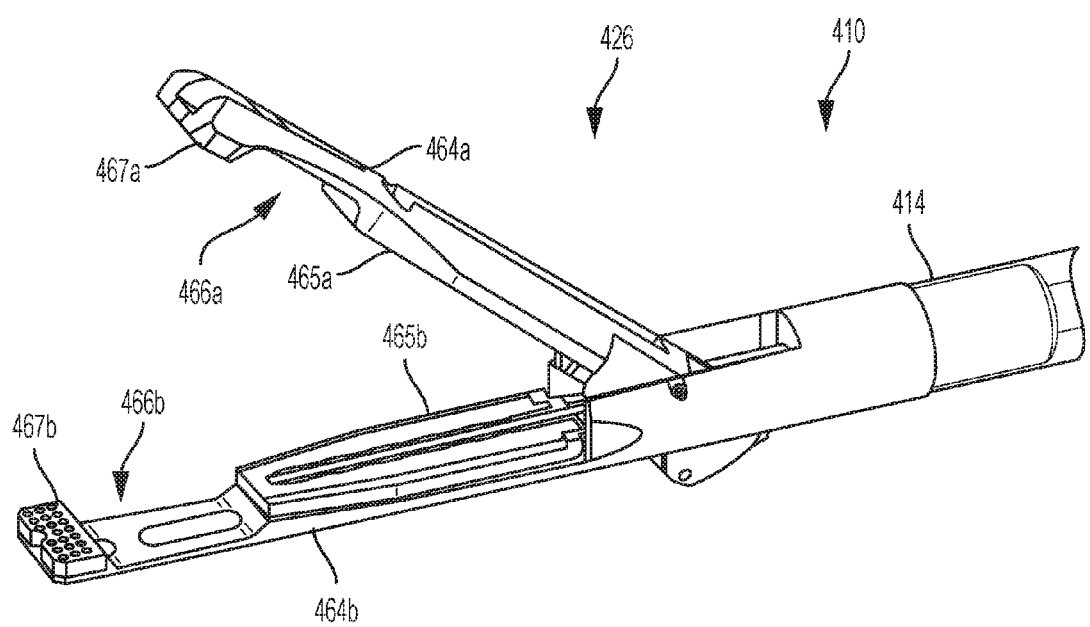
FIG. 14 illustrates one embodiment of an end effector comprising a proximal grasping area and a distal grasping area and defining an aperture therebetween.
Figure 15:
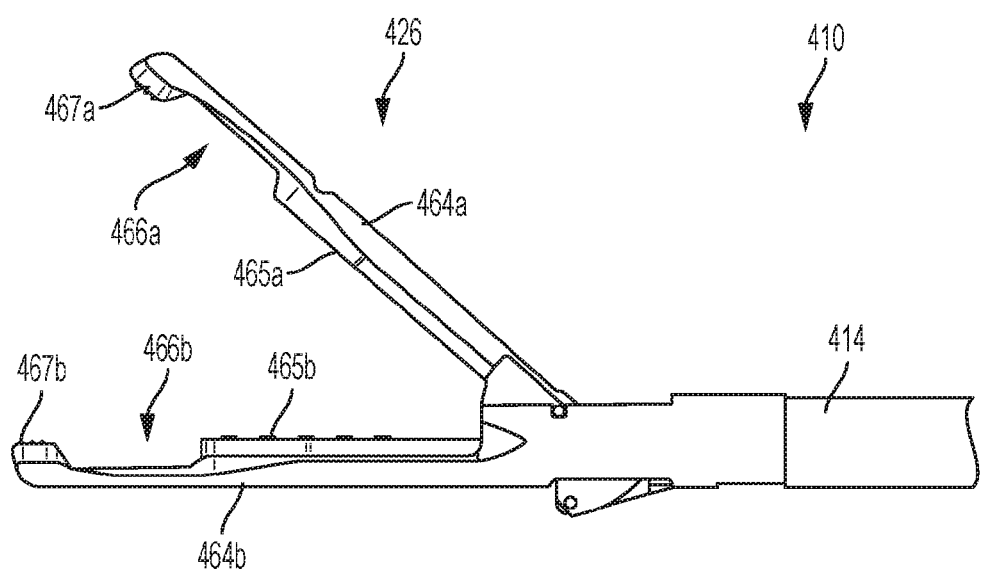
FIG. 15 illustrates a side view of the end effector of FIG. 14 in an open position.

FIG. 14 illustrates one embodiment of an end effector 426 comprising a proximal grasping area and a distal grasping area. The end effector 426 comprises a first jaw member 464a and a second jaw member 464b. The first and second jaw members 464a, 464b are operable to grasp tissue and/or other materials therebetween. The end effector 426 is configured to provide atraumatic grasping. The first jaw member 464a comprises a first proximal contact surface 465a and a first distal contact surface 467a. The first proximal contact surface 465a and the first distal contact surface 467a define a first opening 466a therebetween. The second jaw member 464b comprises a second proximal contact surface 465b and a second distal contact surface 467b. The second proximal contact surface 465b and the second distal contact surface 467b define a second opening 466b therebetween. When the first and second jaw members 464a, 464b are in a closed position, the first and second openings 466a, 466b define an aperture 466. The aperture 466 is configured to receive tissue therein. The aperture 466 provides atraumatic grasping. The end effector 426 may be referred to as a Babcock end effector.

The proximal contact surfaces 465a, 465b are located in the proximal portions of respective first and second jaw members 464a, 464b and define a proximal grasping area 469. In some embodiments, the proximal contact surfaces 465a, 465b comprise an energy delivery surface configured to deliver energy. The proximal contact surfaces 465a, 465b may be configured to provide monopolar RF energy, bipolar RF energy, ultrasonic energy, or any combination thereof to a tissue section grasped between the first jaw member 464a and the second jaw member 464b. The proximal contact surfaces 465a, 465b define a longitudinal channel 462. A cutting member 471 (see FIG. 18) is slideably received within the channel 462. The cutting member 471 is deployable within the longitudinal channel 462 to cut tissue grasped between the proximal contact surfaces 465a, 465b.

Figure 16:
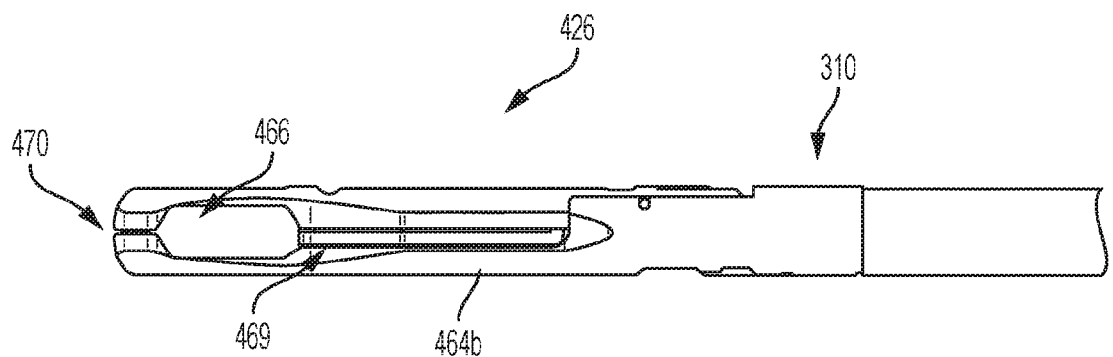
FIG. 16 illustrates a side view of the end effector of FIG. 14 in a closed position.
Figure 17:
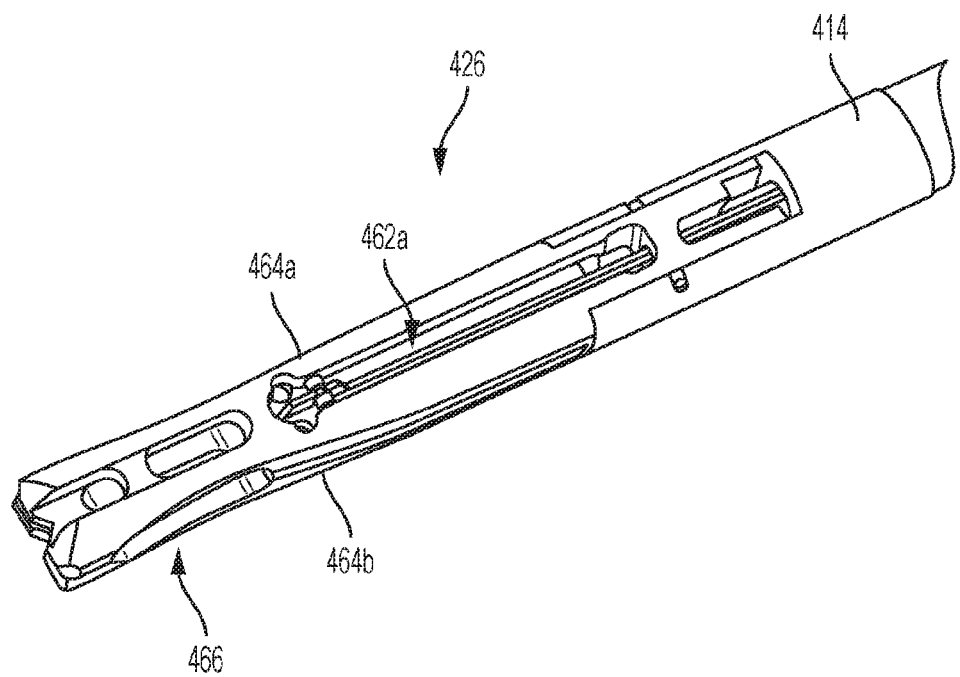
FIG. 17 illustrates a perspective view of the end effector of FIG. 14 in a closed position.
Figure 18:
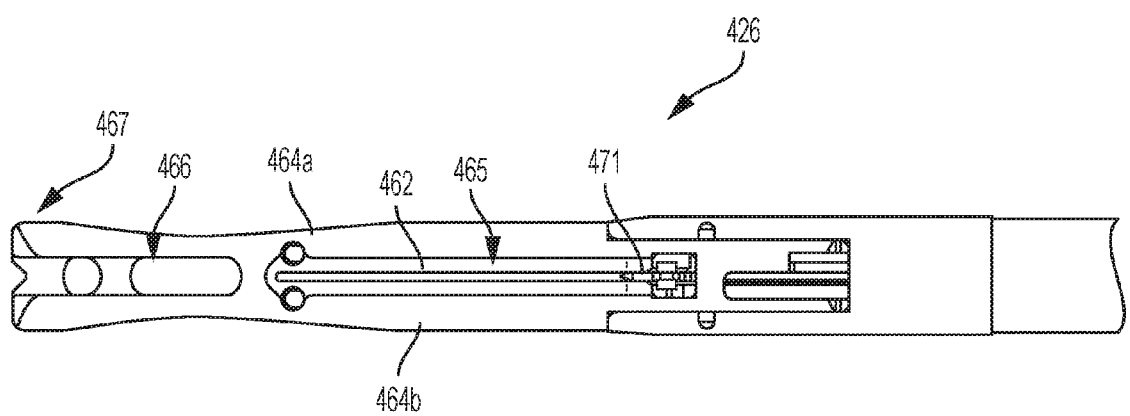
FIG. 18 illustrates a top view of the end effector of FIG. 14.

FIGS. 15-18 illustrate various views of the end effector 426 comprising a proximal grasping area 469 and a distal grasping area 470. FIG. 16 illustrates the end effector 426 in a closed position. The first opening 466a and the second opening 466b align when the end effector 426 is in a closed position to define the aperture 466. The proximal grasping area 469 is located proximally of the aperture 466 and the distal grasping area 470 is located distally of the aperture 466. Grasping tissue with the distal grasping area 470 reduces the surface area of tissue that is grasped and provides for atruamatic grasping. FIGS. 17 and 18 illustrate a top view of the end effector 426. A longitudinal channel 462 is configured to slideably receive a cutting member 471 therein. In the illustrated embodiment, the longitudinal channel 462 extends along the proximal grasping area 469 and does not extend into the aperture 466 or the distal grasping area 470. Cutting of tissue is therefore limited to tissue grasped within the proximal grasping area.

In some embodiments, the first proximal contact surface 465a and/or the second proximal contact surface 465b comprise energy delivery surfaces. The energy deliver surfaces 465a, 465b are configured to deliver energy. The energy delivery surfaces 465a, 465b comprise, for example, one or more electrodes. The energy deliver surfaces 465a, 465b may be configured to deliver monopolar RF energy, bipolar RF energy, ultrasonic energy, or any combination thereof to a tissue section grasped between the first and second jaw members 464a, 464b. The delivered energy may comprise a therapeutic signal configured to seal or weld the tissue section and/or a subtherapeutic signal. In some embodiments, the first proximal contact surface 465a and/or the second proximal contact surface 465b comprise a PTC material configured to limit the delivered energy as the temperature of the treated tissue increases. In some embodiments, the first proximal contact surface 465a and/or the second proximal contact surface 465b may comprise a metal contact electrode and/or an insulative layer.

In various embodiments, the distal contact surfaces 467a, 467b define a distal grasping area 470. The distal grasping area 470 is configured to provide atraumatic grasping. An aperture 466 is defined between the proximal grasping area 469 and the distal grasping area 470. The distal grasping area 470 and the aperture 466 enable the grasping of a tissue section atraumatically. In some embodiments, the distal grasping area 470 is configured to deliver electrosurgical energy to a tissue section grasped therein. In other embodiments, the distal grasping area 470 is electrically inactive.

Figure 19A:
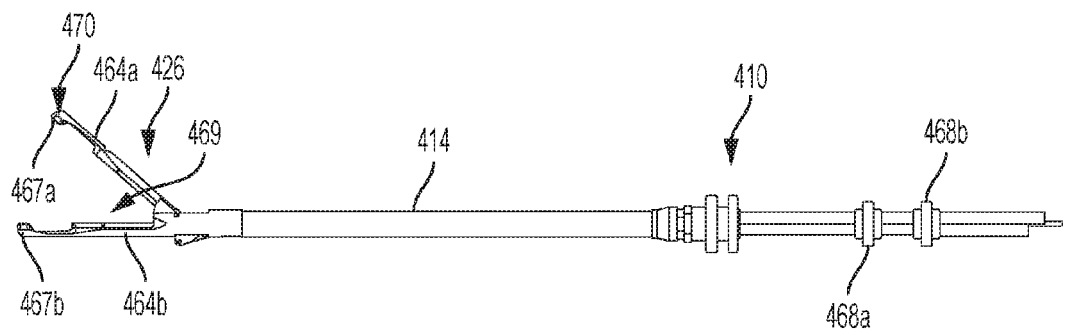
FIG. 19A illustrates one embodiment of an end effector comprising a proximal grasping area and a distal grasping area, defining an aperture therebetween, in an open position.
Figure 19B:
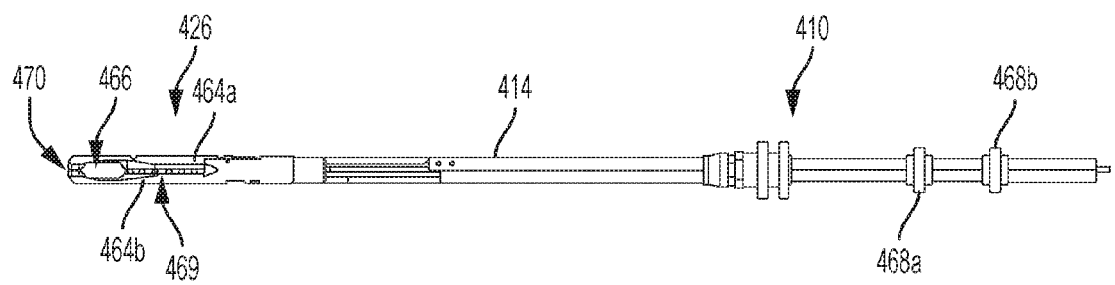
FIG. 19B illustrates one embodiment of the end effector of FIG. 19A in a closed position.
Figure 19C:
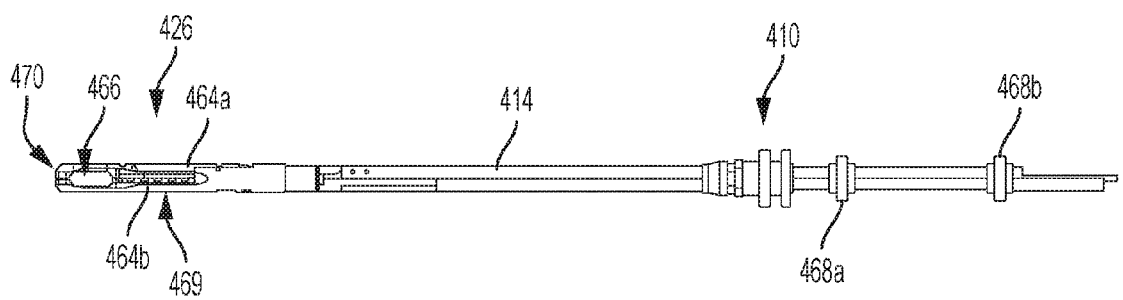
FIG. 19C illustrates one embodiment of the end effector of FIG. 19A in a fired position.

FIG. 19A illustrates one embodiment of the end effector 426 comprising a proximal grasping area and a distal grasping area coupled to an elongate shaft 414. In operation, the end effector 426 is positioned with a tissue section, or other material, located between the first jaw member 464a and the second jaw member 464b. The first jaw member 464a is pivoted to a closed position, as shown in FIG. 19B, to grasp tissue between the first jaw member 464a and the second jaw member 464b. The first jaw member 464a may be pivoted by, for example, actuating a trigger on a handle coupled to the elongate shaft 414 or an actuation ring 468a coupled to the elongate shaft 414. Tissue may be grasped by the proximal grasping area 469, the distal grasping area 470, or both the proximal grasping area 469 and the distal grasping area 470. In some embodiments, the proximal grasping area 469 is configured to treat tissue grasped within the proximal grasping area 469, for example, by delivering energy, stapling, and/or cutting a tissue section grasped in the proximal grasping area. FIG. 19C illustrates the end effector 426 in a fired position. In some embodiments, a cutting instrument 471 is slideably receivable within the longitudinal channel 462 defined by the first and second jaw members 464a, 464b. The cutting instrument 471 is deployable by, for example, advancing a second actuation ring 468b. The second actuation ring 468b causes the cutting instrument 471 to traverse the longitudinal channel 462 and to cut tissue grasped therein.

Figure 20:
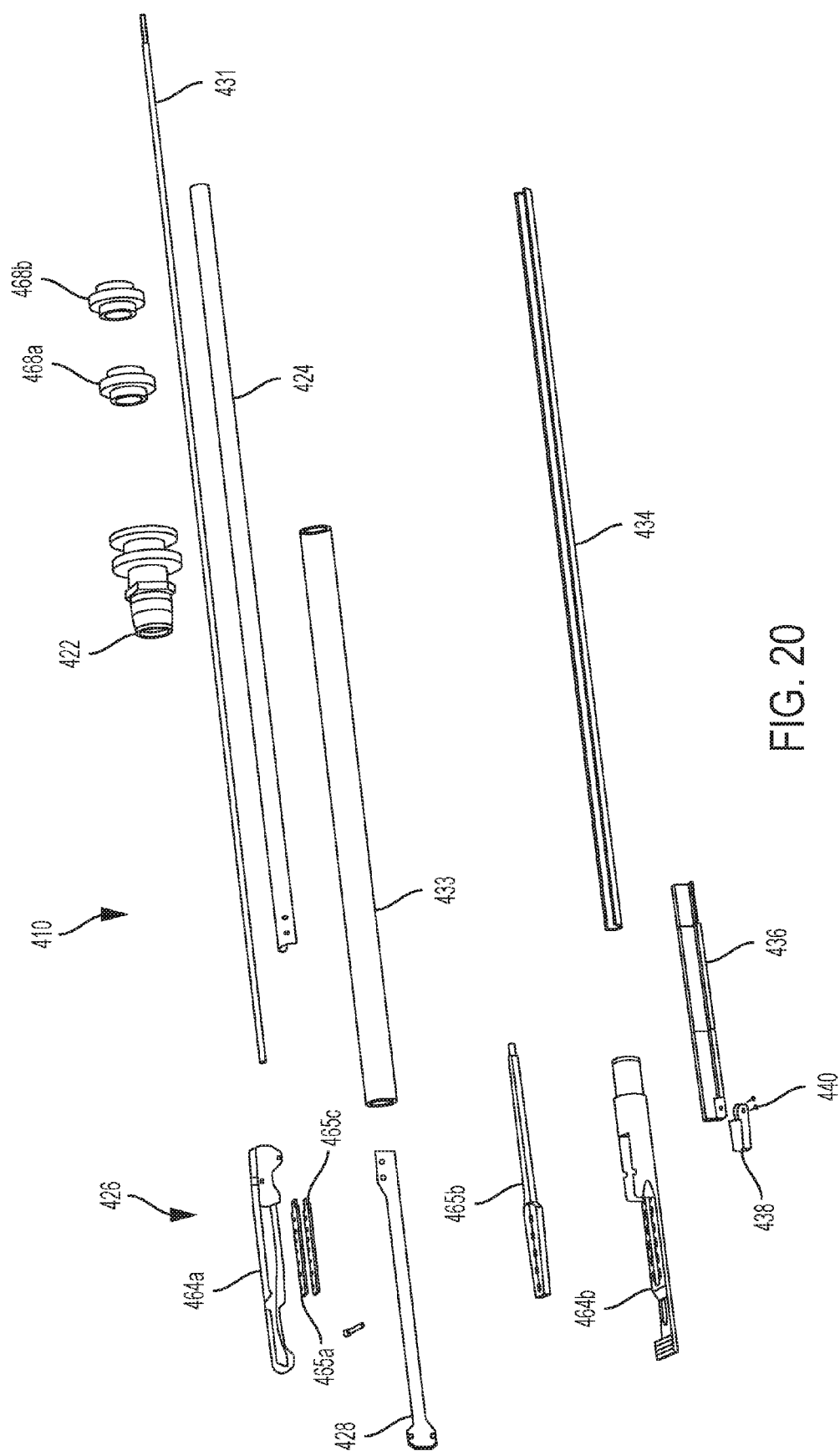
FIG. 20 illustrates an exploded view of the end effector of FIG. 19A.
Figure 21:
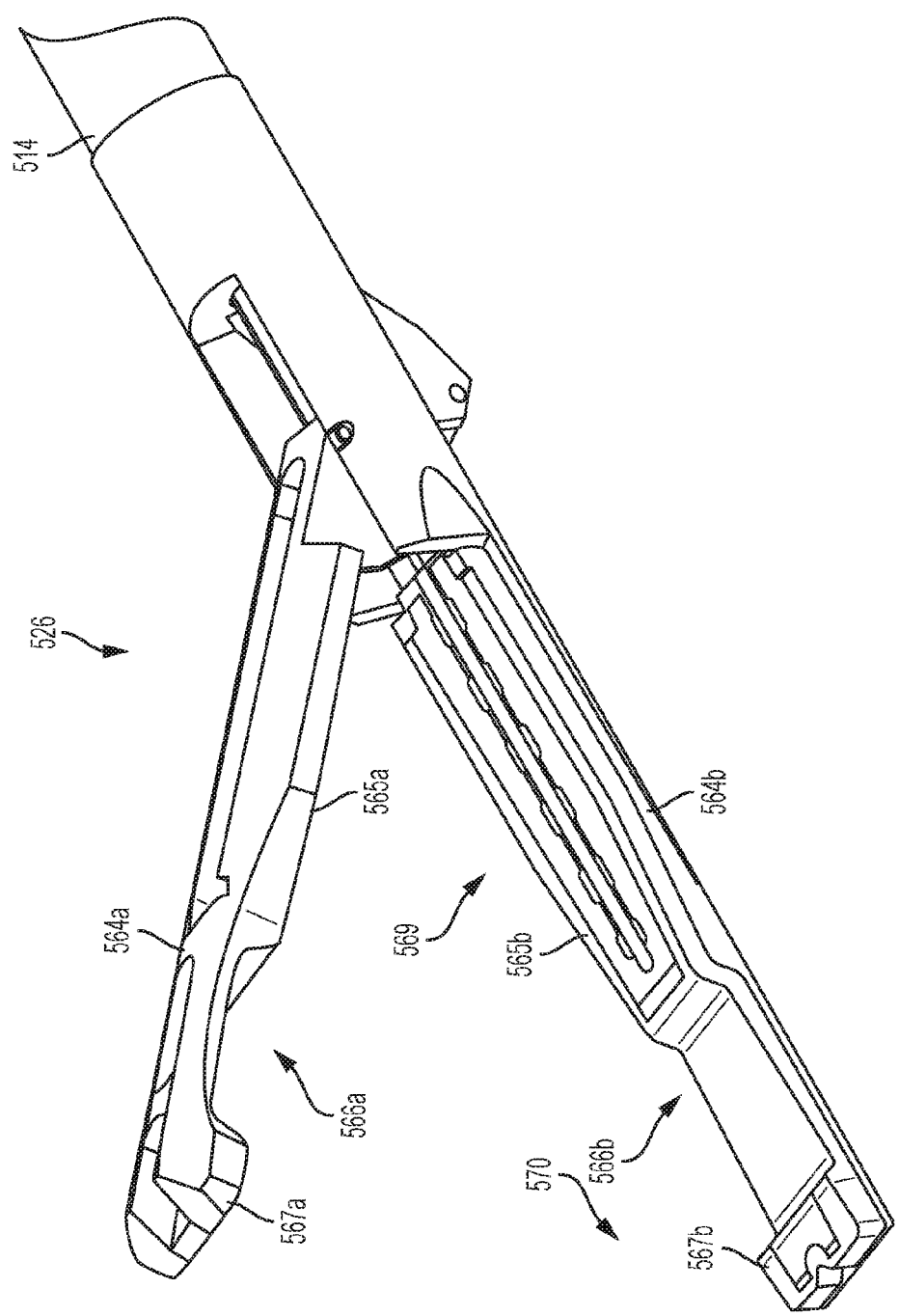
FIG. 21 illustrates one embodiment of an end effector comprising a proximal grasping area including a proximal electrode and a distal grasping area including a distal electrode.

FIG. 20 illustrates an exploded view of the end effector 426 and elongate shaft 414. As illustrated in FIG. 20, the end effector 426 comprises a first jaw member 464a and a second jaw member 464b. A plurality of electrodes 465a, 465c are coupled to the first jaw member 464a to define a proximal energy delivery surface. A source conductor 431 couples the plurality of electrode 465a, 465c to a generator (not shown). A return electrode 465b is coupled to the second jaw member 464b. A return conductor 433 couples the return electrode 465b to the generator. An actuator 424 is coupled to first jaw member 464a to pivot the first jaw member 464a from an open position to a closed position.

FIGS. 21-24 illustrate one embodiment of an end effector 526 comprising a proximal grasping area configured to deliver energy and a distal grasping area configured to deliver energy. A first jaw member 564a comprises a first proximal contact area 565a and a first distal contact area 567a. The first proximal contact area 565a and the first distal contact area 567a define a first opening 566a therebetween. A second jaw member 564b comprises a second proximal contact area 565b and a second distal contact area 567b. The second proximal contact area 565b and the second distal contact area 567b define a second opening 566b therebetween. The first and second openings 566a, 566b define an aperture 566 when the first jaw member 564a and the second jaw member 564b are in a closed position. The first and second proximal contact areas 565a, 565b define a proximal grasping area 569 and the first and second distal contact areas 567a, 567b define a distal grasping area 570.

In some embodiments, the first proximal contact surface 565a and/or the second proximal contact surface 565b comprise energy deliver surfaces. The energy delivery surfaces 565a, 565b are configured to deliver energy. The energy delivery surfaces 565a, 565b may be configured to deliver monopolar RF energy, bipolar RF energy, ultrasonic energy, or any combination thereof to a tissue section grasped between the first and second jaw members 564a, 564b. The delivered energy may comprise a therapeutic signal configured to seal or weld the tissue section and/or a sub-therapeutic signal. In some embodiments, the first proximal contact surface 565a and/or the second proximal contact surface 565b comprise a PTC material configured to limit the delivered energy as the temperature of the treated tissue increases. In some embodiments, the first proximal contact surface 565a and/or the second proximal contact surface 565b may comprise a metal contact electrode and/or an insulative layer. In some embodiments, the first proximal contact surface 565a and/or the second proximal contact surface 565b may comprise a return electrode.

In various embodiments, the distal contact surfaces 567a, 567b define a distal grasping area 570. The distal grasping area 570 is configured to provide atraumatic grasping. An aperture 566 is defined between the proximal grasping area 569 and the distal grasping area 570. The distal grasping area 570 and the aperture 566 enable the grasping of a tissue section atraumatically. In some embodiments, the distal grasping area 570 is configured to deliver electrosurgical energy to a tissue section grasped therein. In other embodiments, the distal grasping area 570 is electrically inactive.

In some embodiments, the first distal contact surface 567a and/or the second distal contact surface 567b comprise energy delivery surfaces, such as, for example, one or more electrodes. The distal energy delivery surfaces 567a, 567b are configured to deliver energy. Energy is delivered to a tissue section grasped within distal grasping area 570. The distal energy delivery surfaces 567a, 567b may be configured to deliver monopolar RF energy, bipolar RF energy, ultrasonic energy, or any combination thereof. The distal energy delivery surfaces 667a, 667b may be configured to provide a therapeutic signal configured to weld or seal a tissue section and/or a sub-therapeutic signal. In some embodiments, the distal grasping area 570 enables an operator to spot weld and/or perform touch-up cauterization after general treatment by the proximal grasping area 569.

In some embodiments, the proximal grasping area 569 and the distal grasping area 570 comprise energy delivery surfaces. The proximal energy deliver surfaces 565a, 565b are operable independently of the distal energy delivery surfaces 567a, 567b. For example, in some embodiments, a handle, such as the handle 112 shown in FIG. 1, comprises a first button for controlling delivery of energy to the proximal grasping area 569 and a second button for controlling delivery of energy to the distal grasping area 570. In other embodiments, a single button is configured to control delivery of energy to both the proximal grasping area 569 and the distal grasping area 570.

Figure 22:
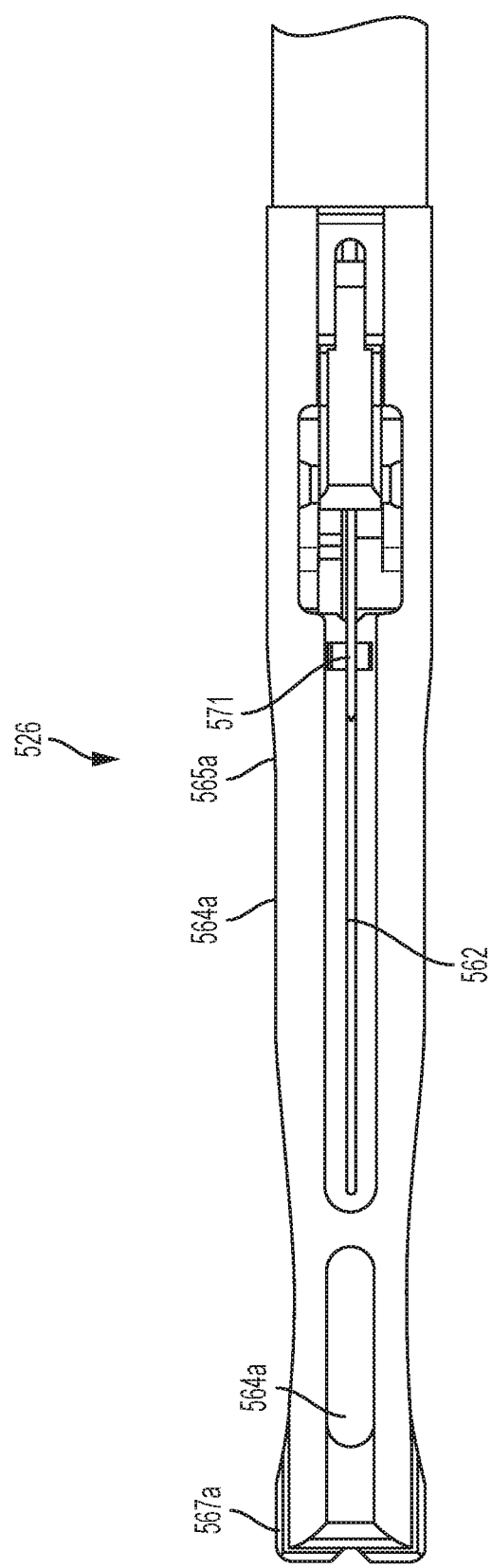
FIG. 22 illustrates a top view of the end effector of FIG. 21.

With reference now to FIG. 22, in some embodiments, the first jaw member 564a and the second jaw member 564b define a longitudinal channel 562. A cutting instrument 571 is slideably receivable within the longitudinal channel 562. The cutting instrument 571 is deployable to cut tissue grasped within the proximal grasping area 569. In the illustrated embodiment, the longitudinal channel 562 extends along the length of the proximal grasping area 569, but does not extend into the aperture 566. Therefore, cutting of tissue is limited to tissue grasped in the proximal grasping area 569.

Figure 23:
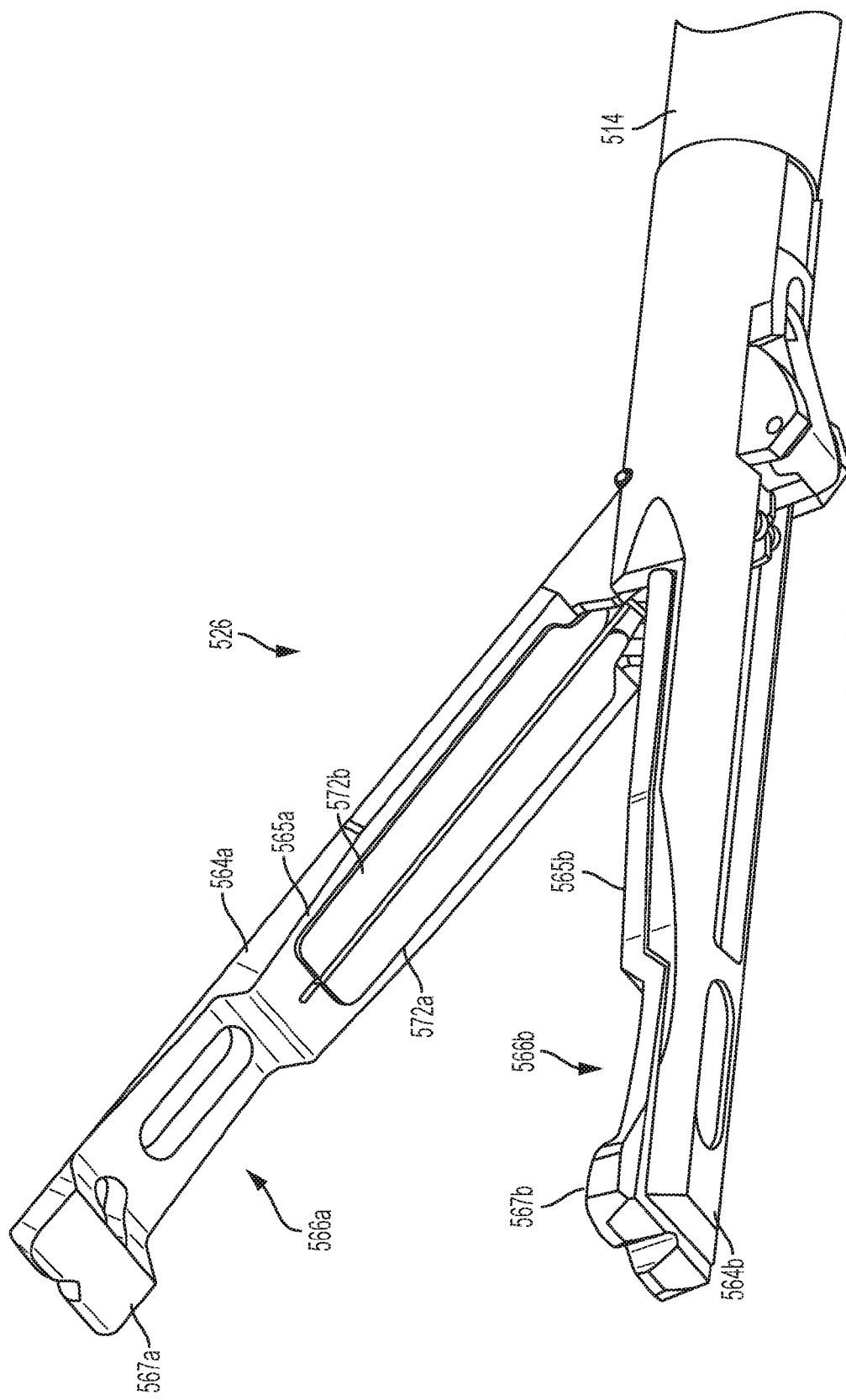
FIG. 23 illustrates a perspective view of the end effector of FIG. 21.

As shown in FIG. 23, in some embodiments, the first proximal contact area 565a comprises a first electrode 572a and a second electrode 572b. The first and second electrodes 572a, 572b are configured to deliver energy. The first and second electrodes 572a, 572b are configured to deliver energy to, for example, a tissue section grasped within the proximal grasping area 569. In one embodiment, the first electrode 572a comprises a source electrode and the second electrode 572b comprises a return electrode. In other embodiments, the first and second electrodes 572a, 572b both comprise source electrodes. The second proximal contact area 565b is configured as a return electrode. In some embodiments, the first and second electrodes 572a, 572b comprise a PTC material.

Figure 24:
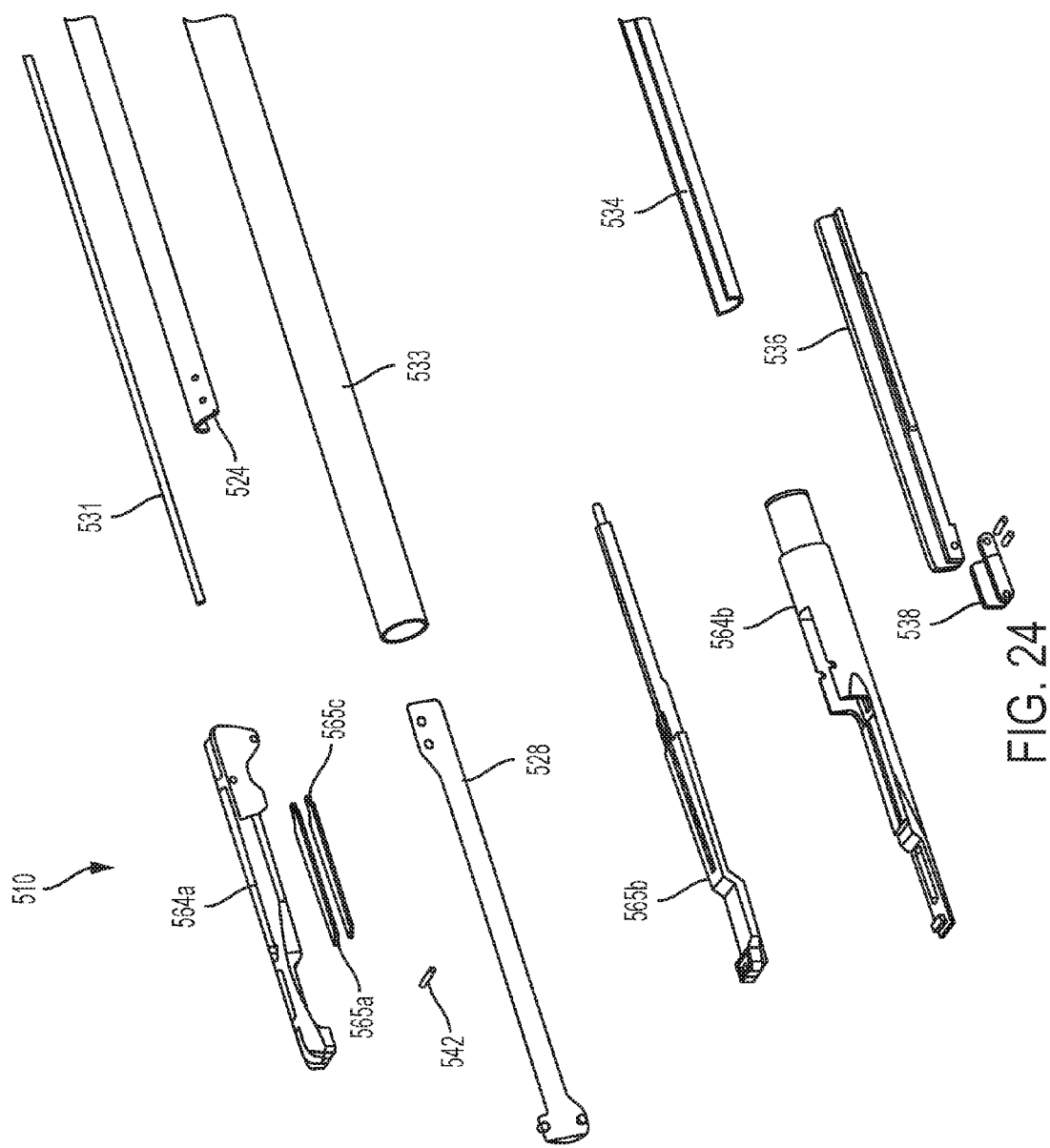
FIG. 24 illustrates an exploded view of the end effector of FIG. 21.
Figure 25:
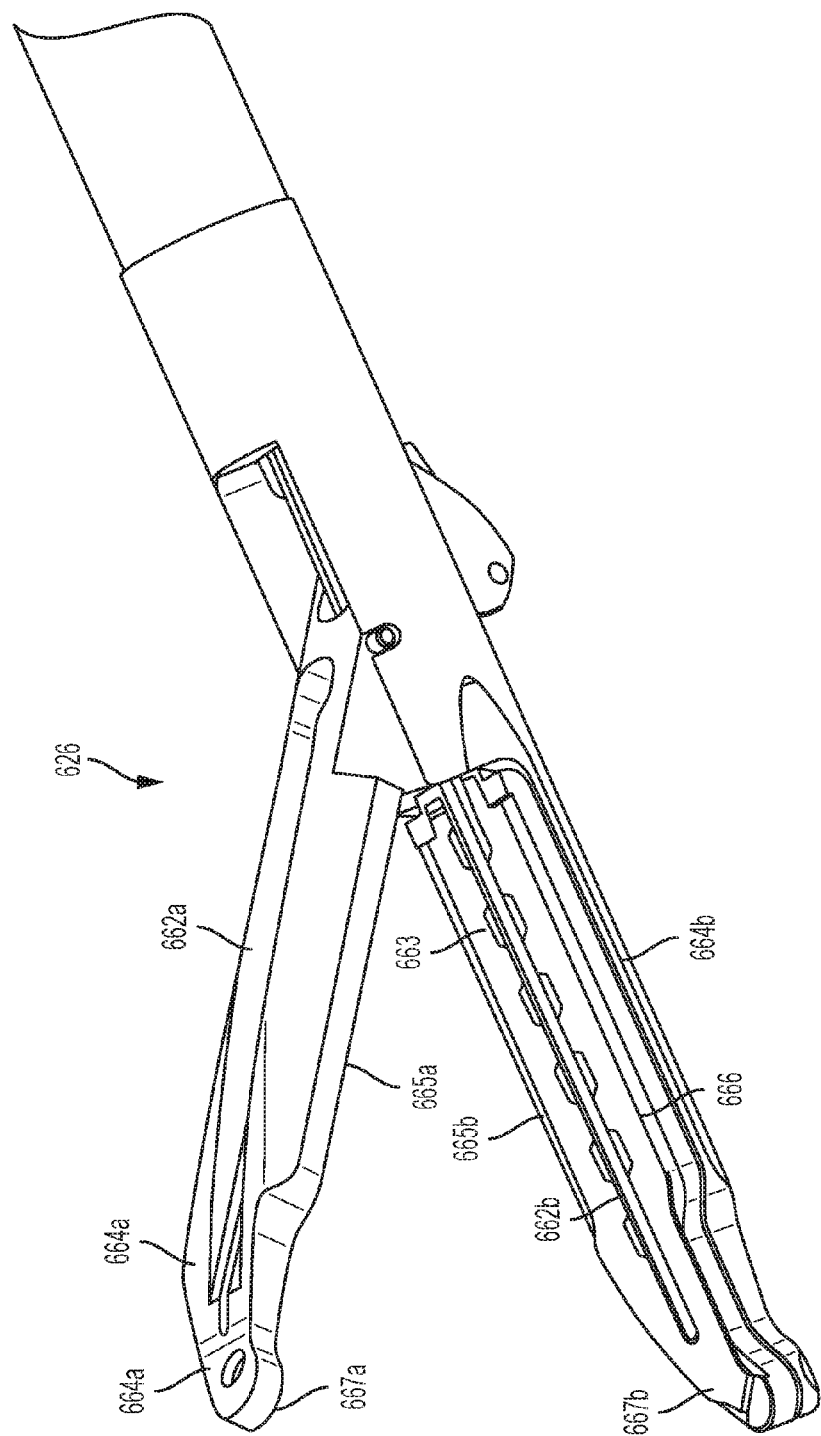
FIG. 25 illustrates one embodiment of an end effector comprising a proximal contact region and a distal contact region.

FIG. 24 illustrates an exploded view of the end effector 526 and elongate shaft 514. As illustrated in FIG. 24, the end effector 526 comprises a first jaw member 564a and a second jaw member 564b. A plurality of electrodes 565a, 565c are coupled to the first jaw member 564a to define a proximal energy delivery surface. A source conductor 531 couples the plurality of electrode 565a, 565c to a generator (not shown). A return electrode 565b is coupled to the second jaw member 564b. A return conductor 533 couples the return electrode 565b to the generator. An actuator 524 is coupled to first jaw member 564a to pivot the first jaw member 564a from an open position to a closed position.

FIGS. 25-28 illustrate one embodiment of an end effector 626 comprising a proximal contact region and a distal contact region. The end effector 626 comprises a first jaw member 664a and a second jaw member 664b. The first jaw member 664a comprises a first proximal contact region 665a and a first distal contact region 667a. The second jaw member 664b comprises a second proximal contact region 665b and a second distal contact region 667b. The first and second proximal contact regions 665a, 665b comprise a first width. The first and second distal contact regions 667a, 667b comprise a second width. The first width is greater than the second width. The proximal contact regions 665a, 665b of the first and second jaw members 664a, 664b provide a contact region for grasping large sections of tissue. The distal contact regions 667a, 667b of the first and second jaw members 664a, 664b provide a contact region for grasping and treating smaller sections of tissue. In some embodiments, the distal contact regions 667a, 667b may comprise a hook shape. The smaller width of the distal contact regions 667a, 667b allows a surgeon to manipulate the end effector 626 to treat difficult to reach tissue sections and/or to apply energy to a smaller tissue section as compared to the proximal contact regions 665a, 665b. For example, in one embodiment, the first width is about 5.0 mm and the second width is about 3.0 mm, allowing a surgeon to access smaller areas not easily accessible by a 5.0 mm surgical instrument.

Figure 26:
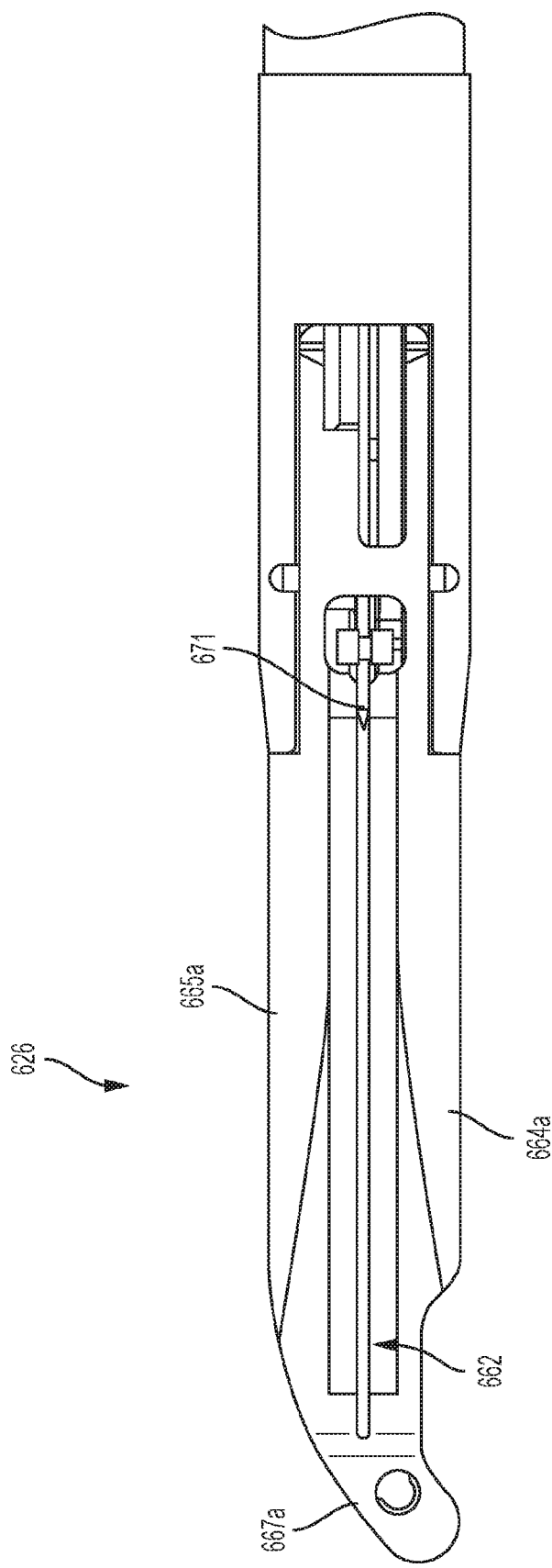
FIG. 26 illustrates a top view of the end effector of FIG. 25.
Figure 27:
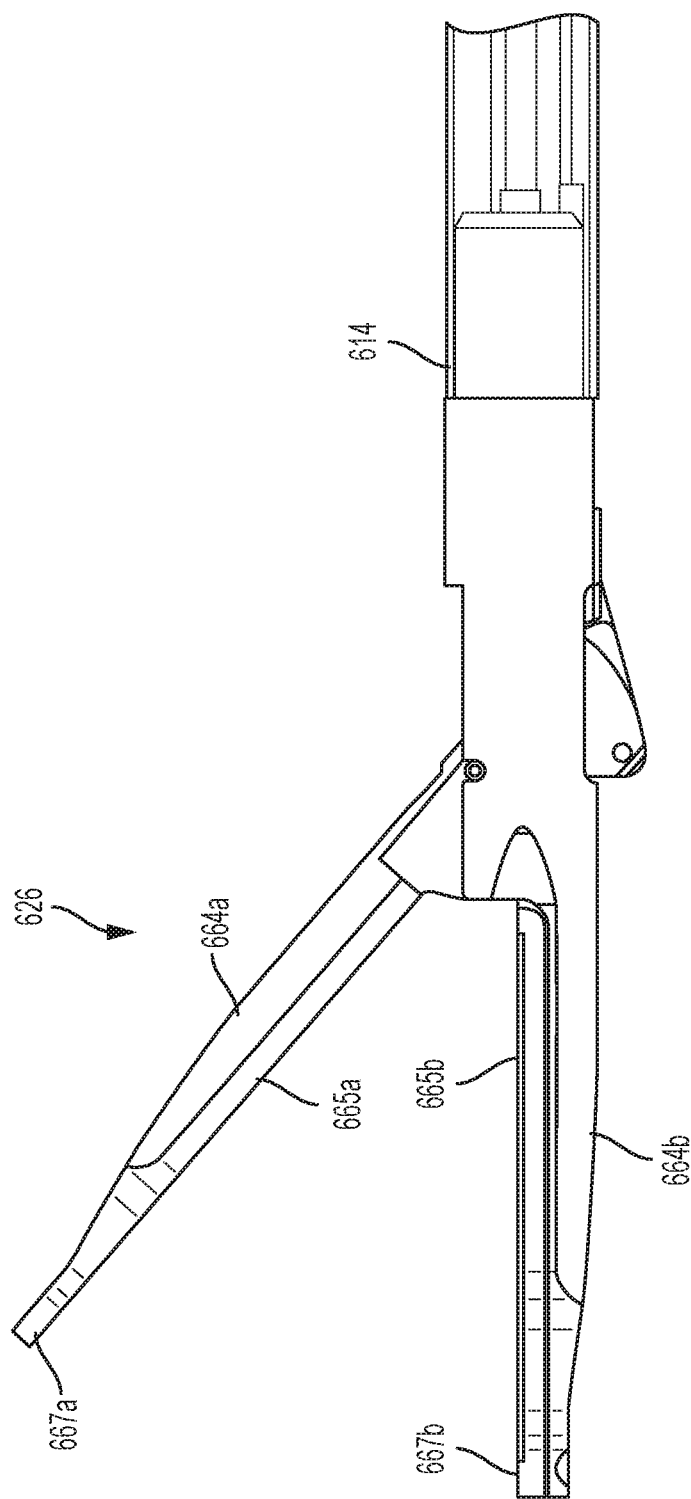
FIG. 27 illustrates a side view of the end effector of FIG. 25 in an open position.
Figure 28:
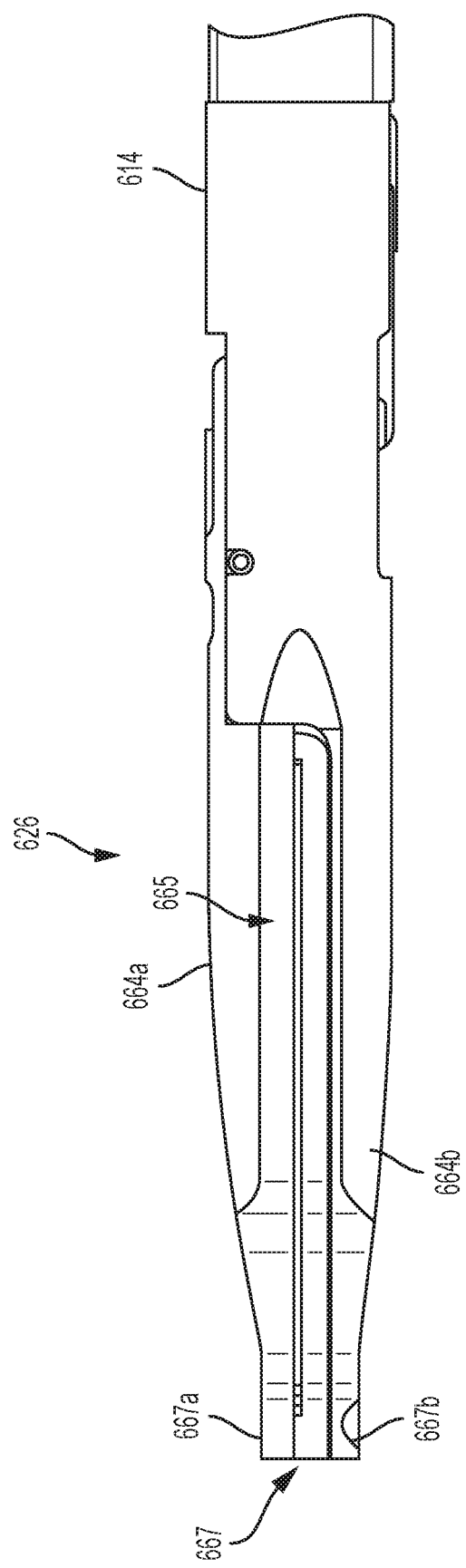
FIG. 28 illustrates a side view of the end effector of FIG. 25 in a closed position.

FIG. 26 illustrates a top view of the end effector 626. The first jaw member 646a and the second jaw member 664b define a longitudinal channel 662. A cutting member 671 is slideably receivable within the longitudinal channel 662. The cutting member 671 may comprise, for example, an I-beam. The cutting member 671 is deployable to cut tissue grasped between the first and second jaw members 664a, 664b. In some embodiments, the cutting member 671 comprises an ultrasonic blade. In the illustrated embodiment, the longitudinal channel 662 extends through both the proximal grasping area 669 and the distal grasping area 670, enabling the cutting member 671 to cut tissue grasped in both the proximal grasping area 669 and the distal grasping area 670.

Figure 29:
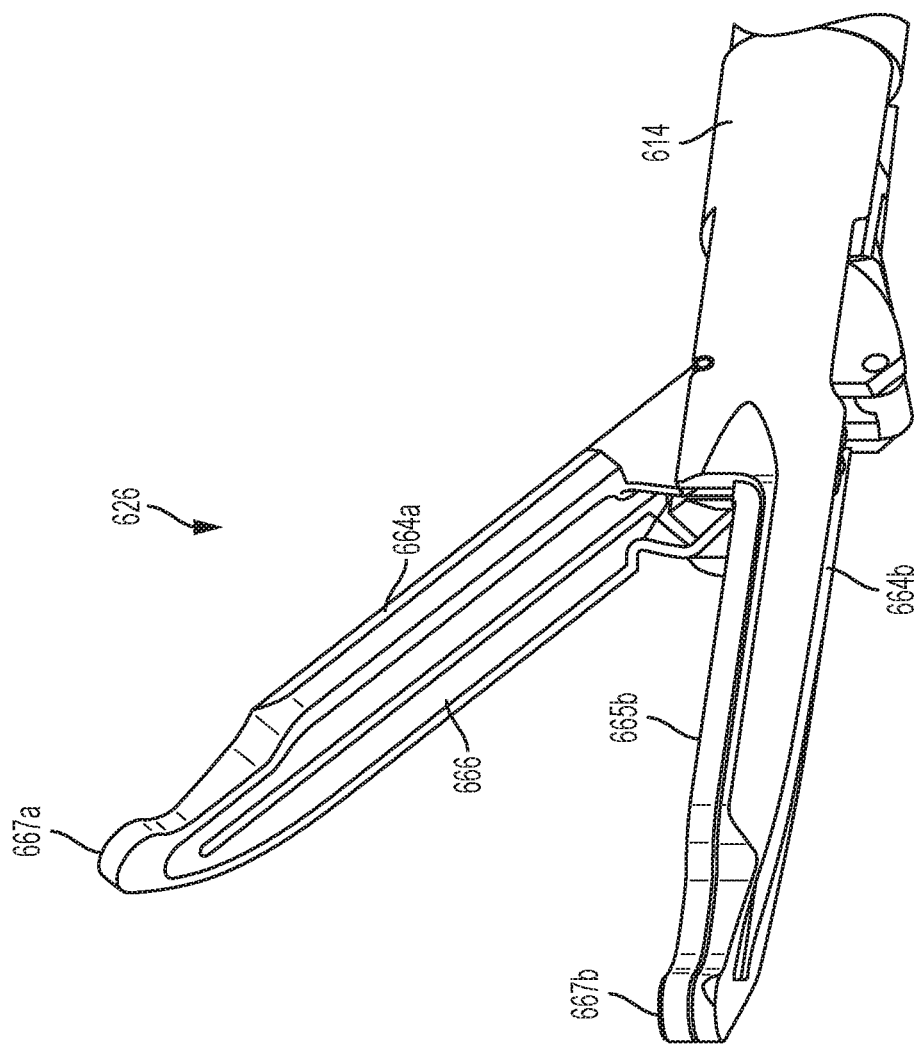
FIG. 29 illustrates one embodiment of an end effector comprising a proximal contact region and a distal contact region, the proximal and distal contact regions comprising a continuous electrode.

FIG. 29 illustrates a perspective view of the end effector 626. In some embodiments, the end effector 626 comprises one or more continuous electrodes 666. The continuous electrode 666 is configured to provide energy to a tissue section grasped between the first jaw member 664a and the second jaw member 664b. The continuous electrode 666 extends over the first proximal contact area 665a and the first distal contact area 667a. The continuous electrode 666 is configured to provide energy to tissue grasped between any section of the first and second jaw members 664a, 664b. In some embodiments, the continuous electrode 666 comprises a monopolar electrode. In other embodiments, the continuous electrode 666 comprises a bi-polar electrode. The second jaw member 664b may comprise a return electrode (not shown). The continuous electrode 666 may be configured to deliver therapeutic RF energy, subtherapeutic RF energy, ultrasonic energy, or any combination thereof.

Figure 30A:
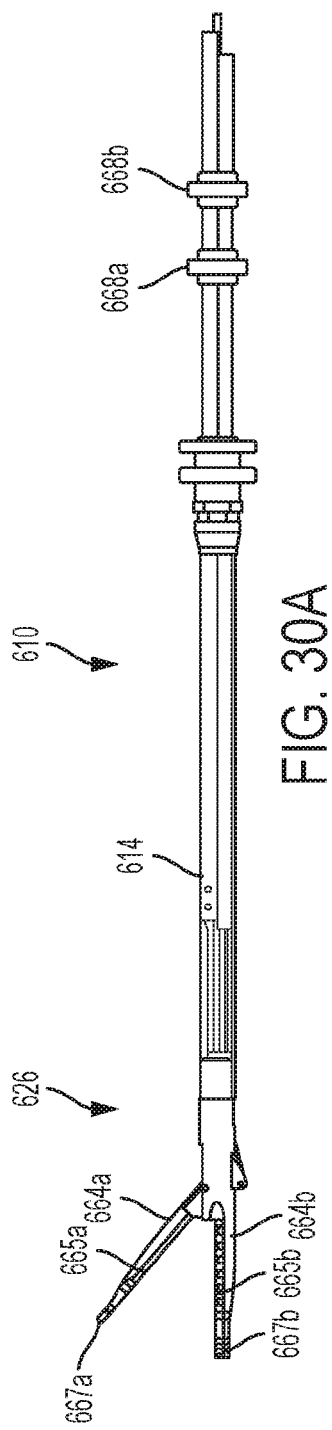
FIG. 30A illustrates one embodiment of an end effector comprising a proximal contact region and a distal contact region in an open position.
Figure 30B:
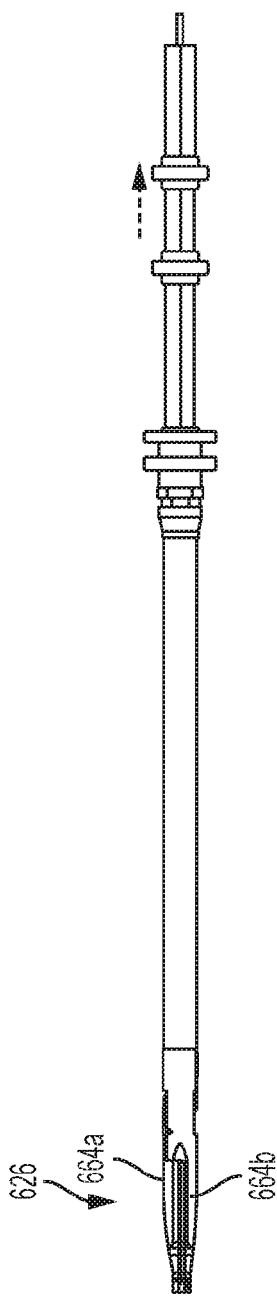
FIG. 30B illustrates the end effector of FIG. 30A in a closed position.
Figure 30C:
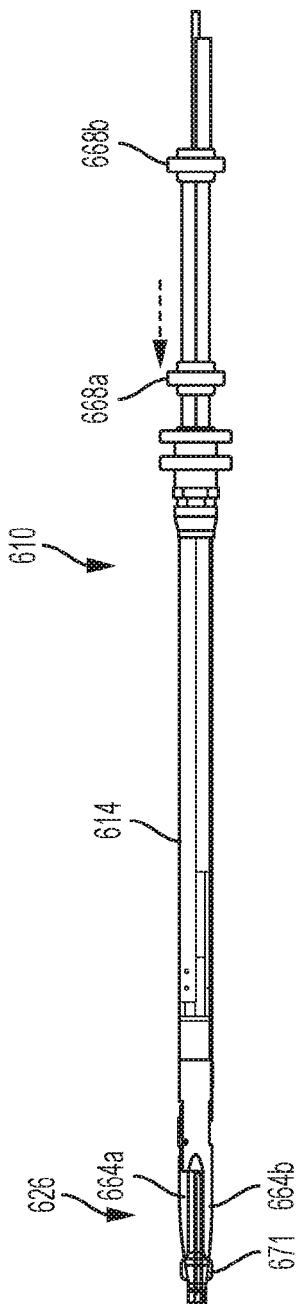
FIG. 30C illustrates the end effector of FIG. 30A in a fired position.

FIGS. 30A-30C illustrate operation of the end effector 626. The end effector 626 is coupled to an elongate shaft 614. FIG. 30A illustrates the first jaw member 664a and the second jaw member 664b in an open position. In operation, the end effector 626 is positioned by a surgeon at a surgical site. The end effector 626 is positioned through, for example, endoscopic, laparoscopic, or open surgery techniques. A surgeon positions a tissue section between the first jaw member 664a and the second jaw member 664b. The surgeon operates a second actuation handle 668b to cause the first jaw member 664a to rotate or transition to a closed position to grasp the tissue section between the first jaw member 664a and the second jaw member 664b, as illustrated in FIG. 30B. Tissue may be grasped between the proximal contact areas 665a, 665b, the distal contact areas 667a, 667b, or both. In some embodiments, the end effector 626 comprises one or more continuous electrodes 666 configured to deliver energy. The surgeon may activate delivery of energy to the electrodes 666. The continuous electrode 666 delivers the energy to the tissue section grasped between the first jaw member 664a and the second jaw member 664b. The delivered energy may weld, cauterize, dissect, and/or otherwise treat the tissue section. In some embodiments, the first jaw member 664a and the second jaw member 664b define a longitudinal channel 662. A cutting member 671 is slideably receivable within the longitudinal channel 662. The cutting member 671 is deployable to cut the tissue section. The cutting member 671 may be deployed, for example, by sliding a first actuation handle 668a distally, causing the cutting member 671 to slideably, distally advance into the longitudinal channel 662. FIG. 30C illustrates the end effector 626 in a fired position, in which the cutting member 671 has been advanced to the distal end of the longitudinal channel 662.

Figure 31:
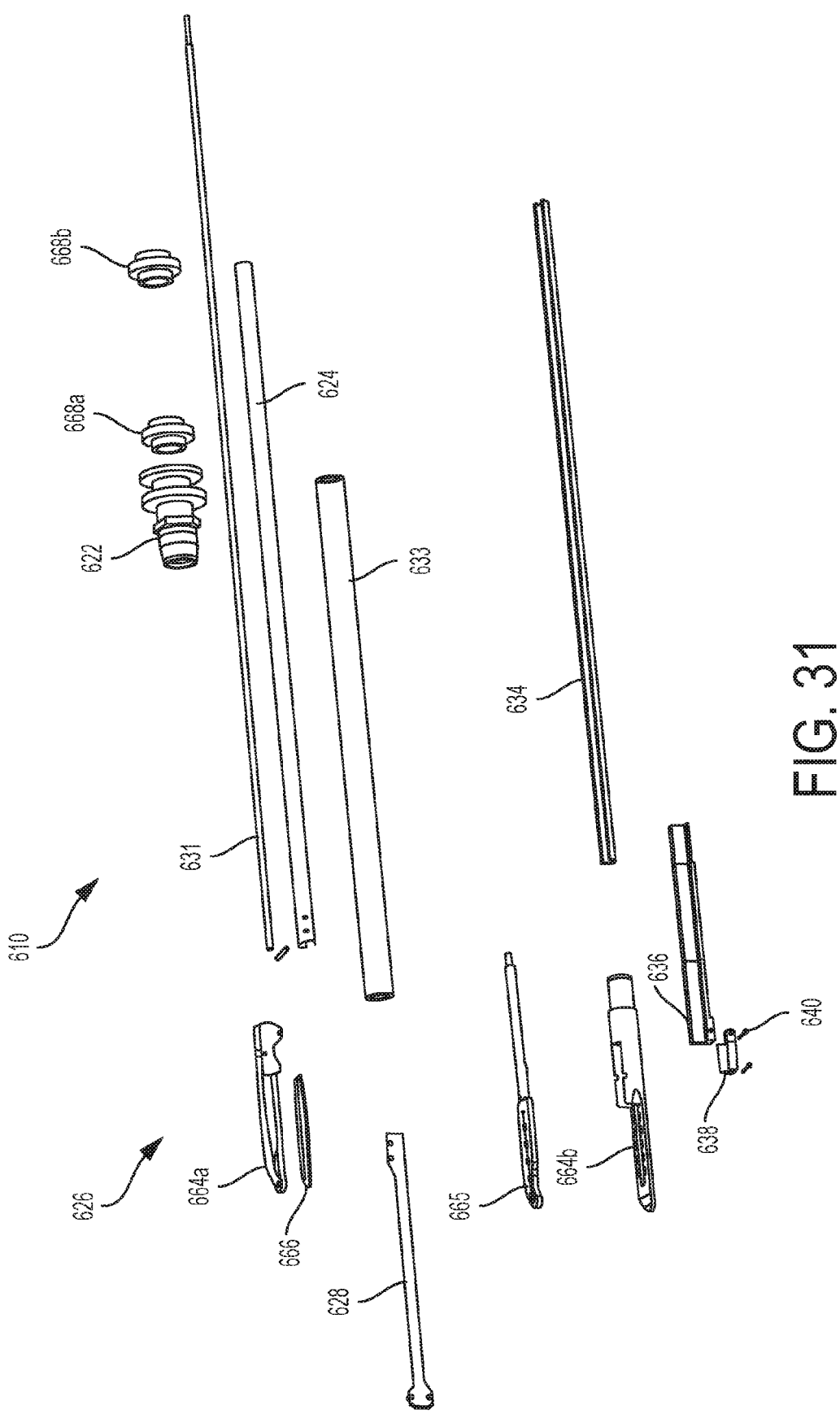
FIG. 31 illustrates an exploded view of the end effector of FIG. 30A.

FIG. 31 illustrates an exploded view of the end effector 626 and elongate shaft 614. As illustrated in FIG. 31, the end effector 626 comprises a first jaw member 664a and a second jaw member 664b. A continuous electrode 666 is coupled to the first jaw member 664a to define a proximal energy delivery surface. A source conductor 631 couples the continuous electrode 666 to a generator (not shown). A return electrode 665 is coupled to the second jaw member 664b. A return conductor 633 couples the return electrode 665 to the generator. An actuator 624 is coupled to first jaw member 664a to pivot the first jaw member 664a from an open position to a closed position.

Figure 32:
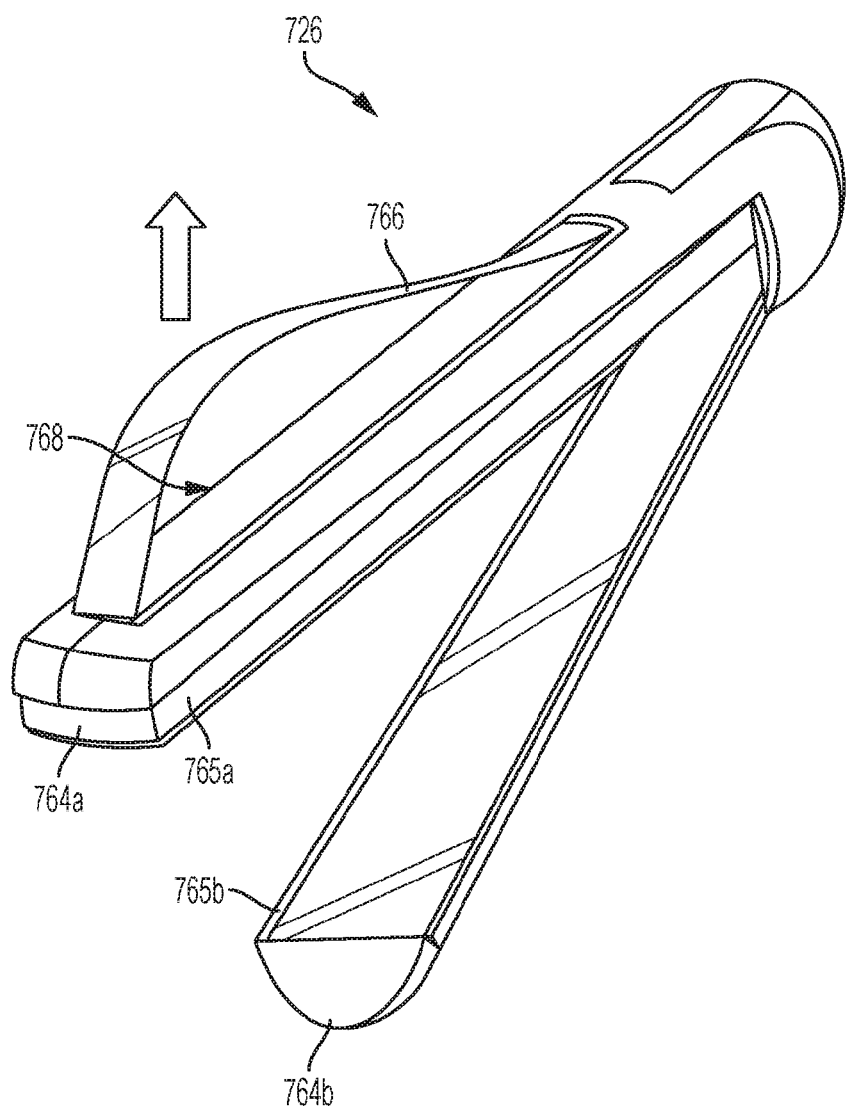
FIG. 32 illustrates one embodiment of an end effector comprising a band electrode in a deployed position.
Figure 33:
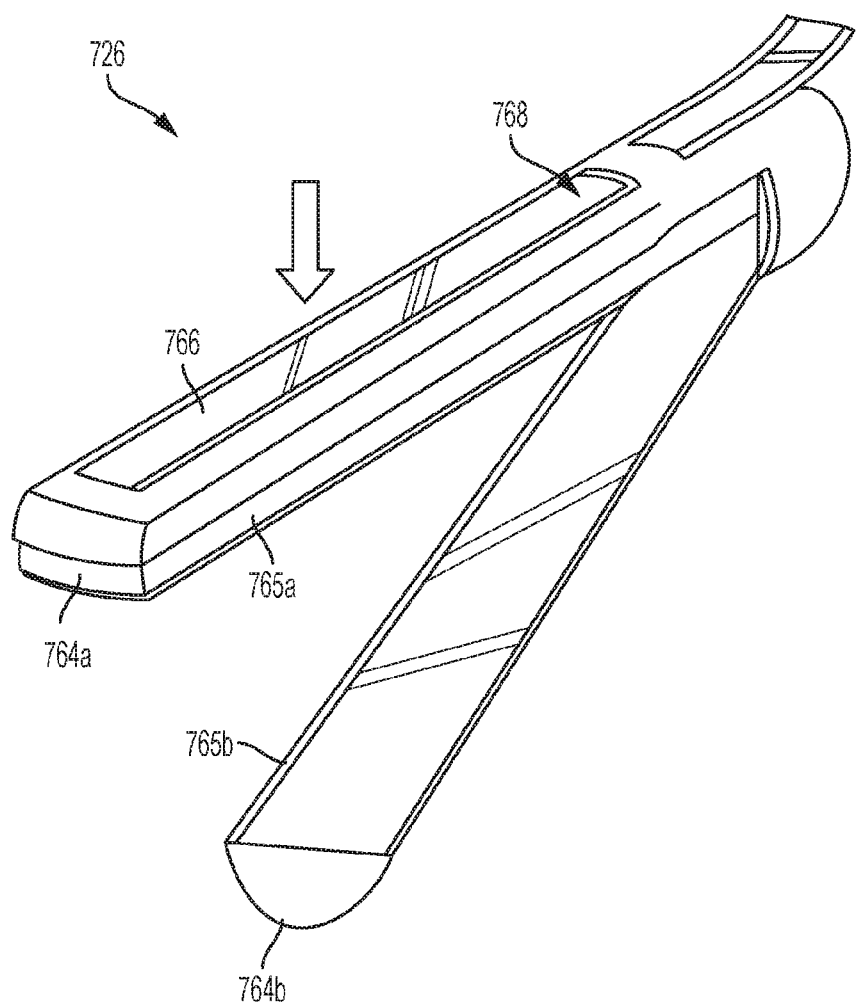
FIG. 33 illustrates the end effector of FIG. 32 in a retracted position.

FIG. 32 illustrates one embodiment of an end effector 726 comprising band electrode 766. The end effector 726 comprises a first jaw member 764a and a second jaw member 764b. A band electrode 766 is coupled to an outer surface of the first jaw member 764a. The band electrode 766 may be coupled, for example, to a top portion of the first jaw member 764a. The band electrode 766 is deployable to deliver energy. The band electrode 766 is configured to deliver energy, for example, to a tissue section in contact with the band electrode 766. FIG. 33 illustrates the band electrode 766 in a retracted position. In some embodiments, the band electrode 766 is configured to lay flush with the first jaw member 764a in a first, or retracted, position. The band electrode 766 is configured to flex outwardly from the first jaw member 764a in a second, or deployed, position, as illustrated in FIG. 32.

The first jaw member 764a comprises a first contact area 765a and the second jaw member 764b comprises a second contact area 765b. The first and second jaw members 764a, 764b are configured to grasp tissue therebetween. In some embodiments, the first contact area 765a and/or the second contact area 765b comprise energy delivery surfaces configured to deliver energy. The energy delivery surfaces 765a, 765b may deliver, for example, therapeutic RF energy, sub-therapeutic RF energy, ultrasonic energy, or any combination thereof. The first and second contact areas 765a, 765b may be configured to provide energy to a tissue section grasped between the first jaw member 764a and the second jaw member 764b. In some embodiments, the first contact area 765a and/or the second contact area 765b comprises a return electrode for energy delivered to a tissue section by the band electrode 766.

In some embodiments, a distal end of the band electrode 766 is fixedly connected to a distal end of the first jaw member 764a. The band electrode 766 is slideably moveable longitudinally relative to the fixed distal end. When the band electrode 766 is slideably moved in a distal direction, the fixed distal end of the band electrode 766 causes the band electrode 766 to flex away from the first jaw member 764a. When the band electrode is slideably moved in a proximal direction, the fixed distal end causes the band electrode 766 to lay flush with the first jaw member 764a.

In some embodiments, the first jaw member 764a comprises a band channel 768. The band electrode 766 is receivable within the band channel 768 in a retracted state. For example, if the band electrode 766 is moved in a proximal direction with respect to the fixed distal end, the band electrode 766 will lay flush against the first jaw member 764a. The band channel 768 receives the band electrode 766. When the band electrode 766 is in a retracted state, the band electrode 766 is flush with or below the outer surface of the first jaw member 764a. In various embodiments, the band channel 768 comprises a longitudinal channel defined by the outer surface of the first jaw member 764a.

It will be appreciated that the terms "proximal" and "distal" are used throughout the specification with reference to a clinician manipulating one end of an instrument used to treat a patient. The term "proximal" refers to the portion of the instrument closest to the clinician and the term "distal" refers to the portion located furthest from the clinician. It will further be appreciated that for conciseness and clarity, spatial terms such as "vertical," "horizontal," "up," or "down" may be used herein with respect to the illustrated embodiments. However, surgical instruments may be used in many orientations and positions, and these terms are not intended to be limiting or absolute.

Various embodiments of surgical instruments and robotic surgical systems are described herein. It will be understood by those skilled in the art that the various embodiments described herein may be used with the described surgical instruments and robotic surgical systems. The descriptions are provided for example only, and those skilled in the art will understand that the disclosed embodiments are not limited to only the devices disclosed herein, but may be used with any compatible surgical instrument or robotic surgical system.

Reference throughout the specification to "various embodiments," "some embodiments," "one example embodiment," or "an embodiment" means that a particular feature, structure, or characteristic described in connection with the embodiment is included in at least one example embodiment. Thus, appearances of the phrases "in various embodiments," "in some embodiments," "in one example embodiment," or "in an embodiment" in places throughout the specification are not necessarily all referring to the same embodiment. Furthermore, the particular features, structures, or characteristics illustrated or described in connection with one example embodiment may be combined, in whole or in part, with features, structures, or characteristics of one or more other embodiments without limitation.

While various embodiments herein have been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art. For example, it is generally accepted that endoscopic procedures are more common than laparoscopic procedures. Accordingly, the present invention has been discussed in terms of endoscopic procedures and apparatus. However, use herein of terms such as "endoscopic", should not be construed to limit the present invention to an instrument for use only in conjunction with an endoscopic tube (e.g., trocar). On the contrary, it is believed that the present invention may find use in any procedure where access is limited to a small incision, including but not limited to laparoscopic procedures, as well as open procedures.

It is to be understood that at least some of the figures and descriptions herein have been simplified to illustrate elements that are relevant for a clear understanding of the disclosure, while eliminating, for purposes of clarity, other elements. Those of ordinary skill in the art will recognize, however, that these and other elements may be desirable. However, because such elements are well known in the art, and because they do not facilitate a better understanding of the disclosure, a discussion of such elements is not provided herein.

While several embodiments have been described, it should be apparent, however, that various modifications, alterations and adaptations to those embodiments may occur to persons skilled in the art with the attainment of some or all of the advantages of the disclosure. For example, according to various embodiments, a single component may be replaced by multiple components, and multiple components may be replaced by a single component, to perform a given function or functions. This application is therefore intended to cover all such modifications, alterations and adaptations without departing from the scope and spirit of the disclosure as defined by the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Various aspects of the subject matter described herein are set out in the following numbered clauses:

1. An end effector comprising: a first jaw member defining a first aperture at a distal end, the first jaw member comprising a first electrode located proximally of the first aperture, wherein the first electrode comprises a positive temperature coefficient (PTC) material; and a second jaw member defining a second aperture at a distal end, the second jaw member comprising a second electrode located proximally of the second aperture, wherein the second jaw member is operatively coupled to the first jaw member, wherein the first and second apertures are configured to define a single aperture when the first and second jaw members are in a closed position, wherein the second electrode comprises a PTC material, and wherein the first and second electrodes are configured to deliver energy.

2. The end effector of clause 1, wherein the first and second jaw members define a longitudinal channel, the end effector comprising a cutting member slideably receivable within the longitudinal channel, wherein the cutting member is deployable along the longitudinal channel, and wherein the longitudinal channel is located proximally of the first and second apertures.

3. The end effector of clause 2, wherein the first electrode comprises a first PTC (positive temperature coefficient) electrode and a second a PTC electrode, wherein the first PTC electrode is located on a first side of the channel and the second PTC electrode is located on a second side of the channel, and wherein the first and second PTC electrodes define a treatment region.

4. The end effector of clause 2, wherein the cutting member comprises an I-beam.

5. The end effector of clause 1, wherein the energy delivered by the first electrode comprises at least one of monopolar electrosurgical energy, bipolar electrosurgical energy, ultrasonic energy, or any combination thereof.

6. An end effector comprising: a first jaw member comprising a first proximal contact surface and a first distal contact surface, wherein the first proximal contact surface and the first distal contact surface define a first opening therebetween; a second jaw member comprising a second proximal contact surface and a second distal contact surface, wherein the second jaw member is operatively coupled to the first jaw member, wherein the second proximal contact surface and the second distal contact surface define a second opening therebetween, and wherein when the first and second jaw members are in a closed position the first and second openings define an aperture; and a first proximal electrode coupled to the first proximal contact surface, wherein the first proximal electrode is configured to deliver energy.

7. The end effector of clause 6, wherein when the first and second jaw members are in a closed position, the proximal contact surfaces define a proximal grasping region and the distal contact surfaces define a distal grasping region.

8. The end effector of clause 6, wherein the energy delivered to the first end effector comprises at least one of monopolar electrosurgical energy, bipolar electrosurgical energy, ultrasonic energy, or any combination thereof.

9. The end effector of clause 8, comprising a second proximal electrode coupled to the second proximal contact surface, wherein the second proximal electrode is configured as a return electrode for electrosurgical energy delivered by the first proximal electrode.

10. The end effector of clause 8, comprising a first distal electrode coupled to the first distal contact surface, wherein the first distal electrode is configured to deliver energy, wherein the energy delivered to the first distal electrode comprises at least one of monopolar electrosurgical energy, bipolar electrosurgical energy, ultrasonic energy, or any combination thereof.

11. The end effector of clause 10, comprising a second distal electrode coupled to the second distal contact surface, wherein the second distal electrode is configured as a return electrode for electrosurgical signal delivered by the first distal electrode.

12. The end effector of clause 6, wherein the first and second jaw members define a longitudinal channel, the end effector comprising a cutting member slideably receivable within the longitudinal channel, wherein the cutting member is deployable along the longitudinal channel.

13. An end effector comprising: a first jaw member operatively coupled to a second jaw member, the first and second jaw members each comprising a proximal contact region defined by a first width and a distal contact region defined by a second width, wherein the first width is greater than the second width, and wherein the distal contact region comprises a hook shape; a first electrode coupled to the first jaw member, the first electrode configured to deliver energy; and a cutting member slideably receivable within a longitudinal channel defined by the first and second jaw members, wherein the cutting member is deployable along the longitudinal channel.

14. The end effector of clause 13, wherein the cutting member comprises an I-beam.

15. The end effector of clause 13, wherein the first electrode comprises a continuous electrode coupled to the proximal contact region and the distal contact region of the first jaw member.

16. The end effector of clause 15, wherein the energy delivered by the first electrode comprises one of monopolar electrosurgical energy, bipolar electrosurgical energy, ultrasonic energy, or any combination thereof.

17. The end effector of clause 16, wherein the second electrode comprises a continuous electrode coupled to the proximal contact region and the distal contact region of the second jaw member.

18. The end effector of clause 16, comprising a second electrode coupled to the second jaw member, wherein the first electrode comprises a source electrode configured to deliver bipolar electrosurgical energy, and wherein the second electrode comprises a return electrode.

19. The end effector of clause 11, wherein the first width is about three millimeters, and wherein the second width is about five millimeters.

20. An end effector comprising: a first jaw member comprising a band electrode coupled to an outer surface of the first jaw member, wherein the band electrode is configured to lay flush with the first jaw member in a first position, and wherein the band electrode is configured to flex outwardly from the first jaw member in a second position, and wherein the band electrode is configured to deliver energy; and a second jaw member operatively coupled to the first jaw member.

21. The end effector of clause 20, wherein the energy delivered by the band electrode comprises monopolar electrosurgical energy, bipolar electrosurgical energy, ultrasonic energy, or any combination thereof.

22. The end effector of clause 20, comprising: a first electrode disposed on an inner surface of the first jaw member; and a second electrode disposed on an inner surface of the second jaw member, wherein the first and second electrodes are configured to deliver energy.

23. The end effector of clause 20, wherein a distal end of the band electrode is fixedly connected to a distal end of the first jaw member, wherein the band electrode is slideably moveable longitudinally relative to the fixed distal end.

24. The end effector of clause 23, wherein the longitudinal movement of the band electrode relative to the fixed distal end causes the band electrode to flex outwardly from the first jaw member.

25. The end effector of clause 24, wherein the first jaw member defines a channel on the outer surface, and wherein the band electrode is positioned within the channel in the first position.

What is claimed is:

1. An end effector comprising:
a first jaw member comprising a first proximal contact surface and a first distal contact surface,
wherein the first proximal contact surface and the first distal contact surface define a first opening therebetween;
a second jaw member comprising a second proximal contact surface and a second distal contact surface,
wherein the second jaw member is operatively coupled to the first jaw member, wherein the second proximal contact surface and the second distal contact surface define a second opening therebetween, and
wherein when the first and second jaw members are in a closed position the first and second openings define an aperture, and the proximal contact surfaces define a proximal grasping region, and
wherein the first and second jaw members define a longitudinal channel, and the longitudinal channel extends along the proximal grasping region and terminates in a closed end proximal to the aperture; and
a first proximal electrode coupled to the first proximal contact surface,
wherein the first proximal electrode is configured to deliver energy, and the energy delivered to the first proximal electrode comprises at least one of monopolar electrosurgical energy, ultrasonic energy, or combination thereof.

2. The end effector of claim 1, wherein when the first and second jaw members are in a closed position, the proximal contact surfaces define a proximal grasping region and the distal contact surfaces define a distal grasping region.

3. The end effector of claim 1, comprising a first distal electrode coupled to the first distal contact surface, wherein the first distal electrode is configured to deliver energy, wherein the energy delivered to the first distal electrode comprises at least one of monopolar electrosurgical energy, ultrasonic energy, or combination thereof.

4. The end effector of claim 1, further comprising a cutting member slideably receivable within the longitudinal channel, wherein the cutting member is deployable along the longitudinal channel.

5. The end effector of claim 1, wherein at least one of the first proximal contact surface or the second proximal contact surface comprises a PTC material.

6. An end effector comprising:
a first jaw member comprising a first proximal contact surface and a first distal contact surface,
wherein the first proximal contact surface and the first distal contact surface define a first opening therebetween;
a second jaw member comprising a second proximal contact surface and a second distal contact surface,
wherein the second jaw member is operatively coupled to the first jaw member, wherein the second proximal contact surface and the second distal contact surface define a second opening therebetween,
wherein when the first and second jaw members are in a closed position, the first and second openings define an aperture, the proximal contact surfaces define a proximal grasping region, and the distal contact surfaces define a distal grasping region, and
wherein the first and second jaw members define a longitudinal channel, and the longitudinal channel extends along the proximal grasping region and terminates in a closed end proximal to the aperture; and
a first proximal electrode coupled to the first proximal contact surface,
wherein the first proximal electrode is configured to deliver energy.

7. The end effector of claim 6, wherein the energy delivered to the first proximal electrode comprises at least one of monopolar electrosurgical energy, bipolar electrosurgical energy, ultrasonic energy, or any combination thereof.

8. The end effector of claim 6, further comprising a second proximal electrode coupled to the second proximal contact surface, wherein the second proximal electrode is configured as a return electrode for electrosurgical energy delivered by the first proximal electrode.

9. The end effector of claim 6, further comprising a first distal electrode coupled to the first distal contact surface, wherein the first distal electrode is configured to deliver energy, wherein the energy delivered to the first distal electrode comprises at least one of monopolar electrosurgical energy, bipolar electrosurgical energy, ultrasonic energy, or any combination thereof.

10. The end effector of claim 9, further comprising a second distal electrode coupled to the second distal contact surface, wherein the second distal electrode is configured as a return electrode for electrosurgical signal delivered by the first distal electrode.

11. The end effector of claim 6, further comprising a cutting member slideably receivable within the longitudinal channel, wherein the cutting member is deployable along the longitudinal channel.

12. The end effector of claim 6, wherein at least one of the first proximal contact surface or the second proximal contact surface comprises a PTC material.

* * * * *